US006686166B2

(12) United States Patent
Behr et al.

(10) Patent No.: US 6,686,166 B2
(45) Date of Patent: Feb. 3, 2004

(54) **MOLECULAR DIFFERENCES BETWEEN SPECIES OF THE *M. TUBERCULOSIS* COMPLEX**

(75) Inventors: Marcel Behr, Montreal (CA); Peter Small, Stanford, CA (US); Gary Schoolnik, Stanford, CA (US); Michael A. Wilson, Stanford, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

(21) Appl. No.: 09/894,844

(22) Filed: Jun. 27, 2001

(65) Prior Publication Data

US 2002/0176873 A1 Nov. 28, 2002

Related U.S. Application Data

(63) Continuation of application No. 09/318,191, filed on May 25, 1999, now Pat. No. 6,291,190.

(60) Provisional application No. 60/097,936, filed on Aug. 25, 1998.

(51) Int. Cl.[7] ........................ G01N 33/53; A61K 39/00; A61K 39/02; C12Q 1/68; C07H 21/04

(52) U.S. Cl. ............................... 435/7.1; 435/4; 435/6; 424/190.1; 424/9; 424/184.1; 436/501; 436/517; 436/518; 436/536; 530/300; 530/350; 536/23.1

(58) Field of Search ............... 435/7.1, 6, 4; 424/190.1, 424/9, 184.1; 436/501, 517, 518, 536; 530/300, 350; 536/23.1

(56) References Cited

U.S. PATENT DOCUMENTS 5,686,597 A 11/1997 Coleman et al.
5,776,465 A 7/1998 O'Donnell et al.
5,955,356 A 9/1999 Content et al.
6,291,190 B1 * 9/2001 Behr et al. .................... 435/7.1

FOREIGN PATENT DOCUMENTS

WO WO 96/27129 2/1996
WO WO 96/25519 8/1996
WO WO 01/04151 * 1/2001

OTHER PUBLICATIONS

Brosch et al. Infection and Immunity, May 1998, vol. 66, No. 5, pp. 2221–2229.*
Mahairas et al. Journal of Bacteriology, Mar. 1996, vol. 178, No. 5, pp. 1274–1282*
Cole, et al. Nature, Jun. 1998, vol. 393, pp. 537–544.*
Cole, et al. Nature, Nov. 1998, vol. 396, Errata, pp. 190–198.*
Gordon et al. Molecular Microbiology, Apr. 1999, vol. 32, No. 3, pp. 643–655.*
Behr et al. Science, May 1999, vol. 284, pp. 1520–1523.*
Aldovini, et al., (1993) *Journal of Bacteriology*, vol. 175:7282–7289.
Converse, et al., (1996) *Infection and Immunity*, vol. 64, No. (11):4776–4787.
Delahunty, et al., (1996) *American Journal of Human Genetics*, vol. 58:1239–1246.
DeRisi, et al., (1996) *Nature Genetics*, vol. 14:457–460.
Ganjam, et al., (1991), *P.N.A.S.*, vol. 88:5433–5437.
Hacia, et al., (1996) *Nature Genetics*, vol. 14:441–447.
Jost, et al., (1994) *Journal of Biochemistry*, vol. 269:26267–73.
Lockhart, et al., (1996) *Nature Biotechnology*, vol. 14:1675–1680.
Norman, et al., (1995) *Molecular Microbiology*, vol. 16:755–760.
Paul, et al., (1996) *journal of Infectious Diseases*, vol. 174, No. (1):105–112.
Philip, W. et al., (1996) *Microbiology*, vol. 142:3135–3145.
Ramsay, et al., (1998) *Nature Biotechnology*, vol. 16:40–44.
Riley, et al., (1990) *Nucleic Acids Research*, vol. 18:2887–2890.
Saiki, et al., (1985) *Science*, vol. 239:487–491.
Sambrook, et al., *Molecular Cloning: A Laboratory Manual, CSH Press* (1989), pp:14.2–14.33.
Shalon, et al., (1996) *Genome Research*, vol. 6:639–645.
Silver, et al., (1998) *Infection and Immunology*, vol. 66, No. (3):1190–1199.
Talbot, et al., (1997) *Journal of Clinical Microbiology*, vol. 35:566–569.

* cited by examiner

*Primary Examiner*—Gerald G. Leffers, Jr.
(74) *Attorney, Agent, or Firm*—Pamela J. Sherwood; Bozicevic, Field & Francis LLP

(57) ABSTRACT

Specific genetic deletions are identified in mycobacteria isolates, including variations in the *M. tuberculosis* genome sequence between isolates, and numerous deletion present in BCG as compared to *M. tb*. These deletions are used as markers to distinguish between pathogenic and avirulent strains, and as a marker for particular *M. tb* isolates. Deletions specific to vaccine strains of BCG are useful in determining whether a positive tuberculin skin test is indicative of actual tuberculosis infection. The deleted sequences may be re-introduced into BCG to improve the efficacy of vaccination. Alternatively, the genetic sequence that corresponds to the deletion(s) are deleted from *M. bovis* or *M. tuberculosis* to attenuate the pathogenic bacteria.

8 Claims, No Drawings

SEQUENCE LISTING

<160> NUMBER OF SEQ ID NOS: 137

<210> SEQ ID NO 1
<211> LENGTH: 1773
<212> TYPE: DNA
<213> ORGANISM: Mycobacteria tuberculosis

<400> SEQUENCE: 1

```
atgactgctg aaccggaagt acggacgctg cgcgaggttg tgctggacca gctcggcact     60
gctgaatcgc gtgcgtacaa gatgtggctg ccgccgttga ccaatccggt cccgctcaac    120
gagctcatcg cccgtgatcg gcgacaaccc ctgcgatttg ccctggggat catggatgaa    180
ccgcgccgcc atctacagga tgtgtggggc gtagacgttt ccggggccgg cggcaacatc    240
ggtattgggg gcgcacctca aaccgggaag tcgacgctac tgcagacgat ggtgatgtcg    300
gccgccgcca cacactcacc gcgcaacgtt cagttctatt gcatcgacct aggtggcggc    360
gggctgatct atctcgaaaa ccttccacac gtcggtgggg tagccaatcg gtccgagccc    420
gacaaggtca accgggtggt cgcagagatg caagccgtca tgcggcaacg ggaaaccacc    480
ttcaaggaac accgagtggg ctcgatcggg atgtaccggc agctgcgtga cgatccaagt    540
caacccgttg cgtccgatcc atacggcgac gtctttctga tcatcgacgg atggcccggt    600
tttgtcggcg agttccccga ccttgagggg caggttcaag atctggccgc ccaggggctg    660
gcgttcggcg tccacgtcat catctccacg ccacgctgga cagagctgaa gtcgcgtgtt    720
cgcgactacc tcggcaccaa gatcgagttc cggcttggtg acgtcaatga aacccagatc    780
gaccggatta cccgcgagat cccggcgaat cgtccgggtc gggcagtgtc gatggaaaag    840
caccatctga tgatcggcgt gcccaggttc gacggcgtgc acagcgccga taacctggtg    900
```

-continued

```
gaggcgatca ccgcgggggt gacgcagatc gcttcccagc acaccgaaca ggcacctccg    960

gtgcgggtcc tgccggagcg tatccacctg cacgaactcg acccgaaccc gccgggacca   1020

gagtccgact accgcactcg ctgggagatt ccgatcggct tgcgcgagac ggacctgacg   1080

ccggctcact gccacatgca cacgaacccg cacctactga tcttcggtgc ggccaaatcg   1140

ggcaagacga ccattgccca cgcgatcgcg cgcgccattt gtgcccgaaa cagtccccag   1200

caggtgcggt tcatgctcgc ggactaccgc tcgggcctgc tggacgcggt gccggacacc   1260

catctgctgg gcgccggcgc gatcaaccgc aacagcgcgt cgctagacga ggccgttcaa   1320

gcactggcgg tcaacctgaa gaagcggttg ccgccgaccg acctgacgac ggcgcagcta   1380

cgctcgcgtt cgtggtggag cggatttgac gtcgtgcttc tggtcgacga ttggcacatg   1440

atcgtgggtg ccgccggggg gatgccgccg atggcaccgc tggccccgtt attgccggcg   1500

gcggcagata tcgggttgca catcattgtc acctgtcaga tgagccaggc ttacaaggca   1560

accatggaca agttcgtcgg cgccgcattc gggtcgggcg ctccgacaat gttcctttcg   1620

ggcgagaagc aggaattccc atccagtgag ttcaaggtca agcggcgccc ccctggccag   1680

gcatttctcg tctcgccaga cggcaaagag gtcatccagg cccccctacat cgagcctcca   1740

gaagaagtgt tcgcagcacc cccaagcgcc ggt                                1773
```

```
<210> SEQ ID NO 2
<211> LENGTH: 297
<212> TYPE: DNA
<213> ORGANISM: Mycobacteria tuberculosis

<400> SEQUENCE: 2

atggaaaaaa tgtcacatga tccgatcgct gccgacattg gcacgcaagt gagcgacaac     60

gctctgcacg gcgtgacggc cggctcgacg gcgctgacgt cggtgaccgg gctggttccc    120

gcgggggccg atgaggtctc cgcccaagcg gcgacggcgt tcacatcgga gggcatccaa    180

ttgctggctt ccaatgcatc ggcccaagac cagctccacc gtgcgggcga agcggtccag    240

gacgtcgccc gcacctattc gcaaatcgac gacggcgccg ccggcgtctt cgccgaa       297
```

```
<210> SEQ ID NO 3
<211> LENGTH: 1104
<212> TYPE: DNA
<213> ORGANISM: Mycobacteria tuberculosis

<400> SEQUENCE: 3

atgctgtggc acgcaatgcc accggagcta aataccgcac ggctgatggc cggcgcgggt     60

ccggctccaa tgcttgcggc ggccgcggga tggcagacgc tttcggcggc tctggacgct    120

caggccgtcg agttgaccgc gcgcctgaac tctctgggag aagcctggac tggaggtggc    180

agcgacaagg cgcttgcggc tgcaacgccg atggtggtct ggctacaaac cgcgtcaaca    240

caggccaaga cccgtgcgat gcaggcgacg gcgcaagccg cggcatacac ccaggccatg    300

gccacgacgc cgtcgctgcc ggagatcgcc gccaaccaca tcacccaggc cgtccttacg    360

gccaccaact tcttcggtat caacacgatc ccgatcgcgt tgaccgagat ggattatttc    420

atccgtatgt ggaaccaggc agccctggca atggaggtct accaggccga gaccgcggtt    480

aacacgcttt tcgagaagct cgagccgatg gcgtcgatcc ttgatcccgg cgcgagccag    540

agcacgacga acccgatctt cggaatgccc tcccctggca gctcaacacc ggttggccag    600

ttgccgccgg cggctaccca gaccctcggc caactgggtg agatgagcgg cccgatgcag    660

cagctgaccc agccgctgca gcaggtgacg tcgttgttca gccaggtggg cggcaccggc    720
```

-continued ggcggcaacc cagccgacga ggaagccgcg cagatgggcc tgctcggcac cagtccgctg 780
tcgaaccatc cgctggctgg tggatcaggc cccagcgcgg gcgcgggcct gctgcgcgcg 840
gagtcgctac ctggcgcagg tgggtcgttg acccgcacgc cgctgatgtc tcagctgatc 900
gaaaagccgg ttgccccctc ggtgatgccg gcggctgctg ccggatcgtc ggcgacgggt 960
ggcgccgctc cggtgggtgc gggagcgatg ggccagggtg cgcaatccgg cggctccacc 1020
aggccgggtc tggtcgcgcc ggcaccgctc gcgcaggagc gtgaagaaga cgacgaggac 1080
gactgggacg aagaggacga ctgg 1104

<210> SEQ ID NO 4
<211> LENGTH: 300
<212> TYPE: DNA
<213> ORGANISM: Mycobacteria tuberculosis

<400> SEQUENCE: 4
atggcagaga tgaagaccga tgccgctacc ctcgcgcagg aggcaggtaa tttcgagcgg 60
atctccggcg acctgaaaac ccagatcgac caggtggagt cgacggcagg ttcgttgcag 120
ggccagtggc gcggcgcggc ggggacggcc gcccaggccg cggtggtgcg cttccaagaa 180
gcagccaata agcagaagca ggaactcgac gagatctcga cgaatattcg tcaggccggc 240
gtccaatact cgagggccga cgaggagcag cagcaggcgc tgtcctcgca aatgggcttc 300

<210> SEQ ID NO 5
<211> LENGTH: 285
<212> TYPE: DNA
<213> ORGANISM: M. tuberculosis

<400> SEQUENCE: 5
atgacagagc agcagtggaa tttcgcgggt atcgaggccg cggcaagcgc aatccaggga 60
aatgtcacgt ccattcattc cctccttgac gaggggaagc agtccctgac caagctcgca 120
gcggcctggg gcggtagcgg ttcggaggcg taccagggtg tccagcaaaa atgggacgcc 180
acggctaccg agctgaacaa cgcgctgcag aacctggcgc ggacgatcag cgaagccggt 240
caggcaatgg cttcgaccga aggcaacgtc actgggatgt tcgca 285

<210> SEQ ID NO 6
<211> LENGTH: 1998
<212> TYPE: DNA
<213> ORGANISM: Mycobacteria tuberculosis

<400> SEQUENCE: 6
atggcggccg actacgacaa gctcttccgg ccgcacgaag gtatggaagc tccggacgat 60
atggcagcgc agccgttctt cgaccccagt gcttcgtttc cgccggcgcc cgcatcggca 120
aacctaccga agcccaacgg ccagactccg cccccgacgt ccgacgacct gtcggagcgg 180
ttcgtgtcgg ccccgccgcc gccacccccca cccccacctc cgcctccgcc aactccgatg 240
ccgatcgccg caggagagcc gccctcgccg gaaccggccg catctaaacc acccacaccc 300
cccatgccca tcgccggacc cgaaccggcc ccacccaaac cacccacacc ccccatgccc 360
atcgccggac ccgaaccggc cccacccaaa ccacccacac ctccgatgcc catcgccgga 420
cctgcaccca ccccaaccga atcccagttg gcgcccccca gaccaccgac accacaaacg 480
ccaaccggag cgccgcagca accggaatca ccggcgcccc acgtaccctc gcacgggcca 540
catcaacccc ggcgcaccgc accagcaccg ccctgggcaa agatgccaat cggcgaaccc 600

-continued

```
ccgcccgctc cgtccagacc gtctgcgtcc ccggccgaac caccgacccg gcctgccccc    660

caacactccc gacgtgcgcg ccggggtcac cgctatcgca cagacaccga acgaaacgtc    720

gggaaggtag caactggtcc atccatccag gcgcggctgc gggcagagga agcatccggc    780

gcgcagctcg cccccggaac ggagccctcg ccagcgccgt tgggccaacc gagatcgtat    840

ctggctccgc ccacccgccc cgcgccgaca gaacctcccc ccagcccctc gccgcagcgc    900

aactccggtc ggcgtgccga gcgacgcgtc caccccgatt tagccgccca acatgccgcg    960

gcgcaacctg attcaattac ggccgcaacc actggcggtc gtcgccgcaa gcgtgcagcg   1020

ccggatctcg acgcgacaca gaaatcctta aggccggcgg ccaaggggcc gaaggtgaag   1080

aaggtgaagc cccagaaacc gaaggccacg aagccgccca aagtggtgtc gcagcgcggc   1140

tggcgacatt gggtgcatgc gttgacgcga atcaacctgg gcctgtcacc cgacgagaag   1200

tacgagctgg acctgcacgc tcgagtccgc cgcaatcccc gcgggtcgta tcagatcgcc   1260

gtcgtcggtc tcaaaggtgg ggctggcaaa accacgctga cagcagcgtt ggggtcgacg   1320

ttggctcagg tgcgggccga ccggatcctg gctctagacg cggatccagg cgccggaaac   1380

ctcgccgatc gggtagggcg acaatcgggc gcgaccatcg ctgatgtgct tgcagaaaaa   1440

gagctgtcgc actacaacga catccgcgca cacactagcg tcaatgcggt caatctggaa   1500

gtgctgccgg caccggaata cagctcggcg cagcgcgcgc tcagcgacgc cgactggcat   1560

ttcatcgccg atcctgcgtc gaggttttac aacctcgtct tggctgattg tggggccggc   1620

ttcttcgacc cgctgacccg cggcgtgctg tccacggtgt ccggtgtcgt ggtcgtggca   1680

agtgtctcaa tcgacggcgc acaacaggcg tcggtcgcgt tggactggtt gcgcaacaac   1740

ggttaccaag atttggcgag ccgcgcatgc gtggtcatca atcacatcat gccgggagaa   1800

cccaatgtcg cagttaaaga cctggtgcgg catttcgaac agcaagttca acccggccgg   1860

gtcgtggtca tgccgtggga caggcacatt gcggccggaa ccgagatttc actcgacttg   1920

ctcgacccta tctacaagcg caaggtcctc gaattggccg cagcgctatc cgacgatttc   1980

gagagggctg gacgtcgt                                                 1998
```

<210> SEQ ID NO 7
<211> LENGTH: 1533
<212> TYPE: DNA
<213> ORGANISM: Mycobacteria tuberculosis

<400> SEQUENCE: 7

```
ttgagcgcac ctgctgttgc tgctggtcct accgccgcgg gggcaaccgc tgcgcggcct     60

gccaccaccc gggtgacgat cctgaccggc agacggatga ccgatttggt actgccagcg    120

gcggtgccga tggaaactta tattgacgac accgtcgcgg tgctttccga ggtgttggaa    180

gacacgccgg ctgatgtact cggcggcttc gactttaccg cgcaaggcgt gtgggcgttc    240

gctcgtcccg gatcgccgcc gctgaagctc gaccagtcac tcgatgacgc cggggtggtc    300

gacgggtcac tgctgactct ggtgtcagtc agtcgcaccg agcgctaccg accgttggtc    360

gaggatgtca tcgacgcgat cgccgtgctt gacgagtcac ctgagttcga ccgcacggca    420

ttgaatcgct ttgtgggggc ggcgatcccg cttttgaccg cgcccgtcat cgggatggcg    480

atgcgggcgt ggtgggaaac tgggcgtagc ttgtggtggc cgttggcgat tggcatcctg    540

gggatcgctg tgctggtagg cagcttcgtc gcgaacaggt tctaccagag cggccacctg    600

gccgagtgcc tactggtcac gacgtatctg ctgatcgcaa ccgccgcagc gctggccgtg    660

ccgttgccgc gcggggtcaa ctcgttgggg gcgccacaag ttgccggcgc cgctacggcc    720
```

-continued

```
gtgctgtttt tgaccttgat gacgcggggc ggccctcgga agcgtcatga gttggcgtcg     780

tttgccgtga tcaccgctat cgcggtcatc gcggccgccg ctgccttcgg ctatggatac     840

caggactggg tccccgcggg ggggatcgca ttcgggctgt tcattgtgac gaatgcggcc     900

aagctgaccg tcgcggtcgc gcggatcgcg ctgccgccga ttccggtacc cggcgaaacc     960

gtggacaacg aggagttgct cgatcccgtc gcgaccccgg aggctaccag cgaagaaacc    1020

ccgacctggc aggccatcat cgcgtcggtg cccgcgtccg cggtccggct caccgagcgc    1080

agcaaactgg ccaagcaact tctgatcgga tacgtcacgt cgggcaccct gattctggct    1140

gccggtgcca tcgcggtcgt ggtgcgcggg cacttctttg tacacagcct ggtggtcgcg    1200

ggtttgatca cgaccgtctg cggatttcgc tcgcggcttt acgccgagcg ctggtgtgcg    1260

tgggcgttgc tggcggcgac ggtcgcgatt ccgacgggtc tgacggccaa actcatcatc    1320

tggtacccgc actatgcctg gctgttgttg agcgtctacc tcacggtagc cctggttgcg    1380

ctcgtggtgg tcgggtcgat ggctcacgtc cggcgcgttt caccggtcgt aaaacgaact    1440

ctggaattga tcgacggcgc catgatcgct gccatcattc ccatgctgct gtggatcacc    1500

ggggtgtacg acacggtccg caatatccgg ttc                                 1533
```

<210> SEQ ID NO 8
<211> LENGTH: 840
<212> TYPE: DNA
<213> ORGANISM: Mycobacteria tuberculosis

<400> SEQUENCE: 8

```
atggctgaac cgttggccgt cgatcccacc ggcttgagcg cagcggccgc gaaattggcc      60

ggcctcgttt ttccgcagcc tccggcgccg atcgcggtca gcggaacgga ttcggtggta     120

gcagcaatca acgagaccat gccaagcatc gaatcgctgg tcagtgacgg gctgcccggc     180

gtgaaagccg ccctgactcg aacagcatcc aacatgaacg cggcggcgga cgtctatgcg     240

aagaccgatc agtcactggg aaccagtttg agccagtatg cattcggctc gtcgggcgaa     300

ggcctggctg gcgtcgcctc ggtcggtggt cagccaagtc aggctaccca gctgctgagc     360

acacccgtgt cacaggtcac gacccagctc ggcgagacgg ccgctgagct ggcaccccgt     420

gttgttgcga cggtgccgca actcgttcag ctggctccgc acgccgttca gatgtcgcaa     480

aacgcatccc ccatcgctca gacgatcagt caaaccgccc aacaggccgc ccagagcgcg     540

cagggcggca gcggcccaat gcccgcacag cttgccagcg ctgaaaaacc ggccaccgag     600

caagcggagc cggtccacga agtgacaaac gacgatcagg gcgaccaggg cgacgtgcag     660

ccggccgagg tcgttgccgc ggcacgtgac gaaggcgccg gcgcatcacc gggccagcag     720

cccggcgggg gcgttcccgc gcaagccatg gataccggag ccggtgcccg cccagcggcg     780

agtccgctgg cggcccccgt cgatccgtcg actccggcac cctcaacaac cacaacgttg     840
```

<210> SEQ ID NO 9
<211> LENGTH: 2187
<212> TYPE: DNA
<213> ORGANISM: Mycobacteria tuberculosis

<400> SEQUENCE: 9

```
atgagtatta ccaggccgac gggcagctat gccagacaga tgctggatcc gggcggctgg      60

gtggaagccg atgaagacac tttctatgac cgggcccagg aatatagcca ggttttgcaa     120

agggtcaccg atgtattgga cacctgccgc cagcagaaag gccacgtctt cgaaggcggc     180
```

-continued

```
ctatggtccg gcggcgccgc caatgctgcc aacggcgccc tgggtgcaaa catcaatcaa    240

ttgatgacgc tgcaggatta tctcgccacg gtgattacct ggcacaggca tattgccggg    300

ttgattgagc aagctaaatc cgatatcggc aataatgtgg atggcgctca acgggagatc    360

gatatcctgg agaatgaccc tagcctggat gctgatgagc gccataccgc catcaattca    420

ttggtcacgg cgacgcatgg ggccaatgtc agtctggtcg ccgagaccgc tgagcgggtg    480

ctggaatcca agaattggaa acctccgaag aacgcactcg aggatttgct tcagcagaag    540

tcgccgccac ccccagacgt gcctaccctg gtcgtgccat ccccgggcac accgggcaca    600

ccgggaaccc cgatcacccc gggaaccccg atcaccccgg gaaccccaat cacacccatc    660

ccgggagcgc cggtaactcc gatcacacca acgcccggca ctcccgtcac gccggtgacc    720

ccgggcaagc cggtcacccc ggtgaccccg gtcaaaccgg gcacaccagg cgagccaacc    780

ccgatcacgc cggtcacccc cccggtcgcc ccggccacac cggcaacccc ggccacgccc    840

gttaccccag ctcccgctcc acacccgcag ccggctccgg caccggcgcc atcgcctggg    900

ccccagccgg ttacaccggc cactcccggt ccgtctggtc cagcaacacc gggcacccca    960

gggggcgagc cggcgccgca cgtcaaaccc gcggcgttgg cggagcaacc tggtgtgccg   1020

ggccagcatg cgggcggggg gacgcagtcg gggcctgccc atgcggacga atccgccgcg   1080

tcggtgacgc cggctgcggc gtccggtgtc ccgggcgcac gggcggcggc cgccgcgccg   1140

agcggtaccg ccgtgggagc gggcgcgcgt tcgagcgtgg gtacggccgc ggcctcgggc   1200

gcggggtcgc atgctgccac tggcgggcg ccggtggcta cctcggacaa ggcggcggca   1260

ccgagcacgc gggcggcctc ggcgcggacg gcacctcctg cccgcccgcc gtcgaccgat   1320

cacatcgaca aacccgatcg cagcgagtct gcagatgacg gtacgccggt gtcgatgatc   1380

ccggtgtcgg cggctcgggc ggcacgcgac gccgccactg cagctgccag cgcccgccag   1440

cgtggccgcg gtgatgcgct gcggttggcg cgacgcatcg cggcggcgct caacgcgtcc   1500

gacaacaacg cgggcgacta cgggttcttc tggatcaccg cggtgaccac cgacggttcc   1560

atcgtcgtgg ccaacagcta tgggctggcc tacatacccg acgggatgga attgccgaat   1620

aaggtgtact tggccagcgc ggatcacgca atcccggttg acgaaattgc acgctgtgcc   1680

acctacccgg ttttggccgt gcaagcctgg gcggctttcc acgacatgac gctgcgggcg   1740

gtgatcggta ccgcggagca gttggccagt tcggatcccg gtgtggccaa gattgtgctg   1800

gagccagatg acattccgga gagcggcaaa atgacgggcc ggtcgcggct ggaggtcgtc   1860

gacccctcgg cggcggctca gctggccgac actaccgatc agcgtttgct cgacttgttg   1920

ccgccggcgc cggtggatgt caatccaccg ggcgatgagc ggcacatgct gtggttcgag   1980

ctgatgaagc ccatgaccag caccgctacc ggccgcgagg ccgctcatct gcgggcgttc   2040

cgggcctacg ctgcccactc acaggagatt gccctgcacc aagcgcacac tgcgactgac   2100

gcggccgtcc agcgtgtggc cgtcgcggac tggctgtact ggcaatacgt caccgggttg   2160

ctcgaccggg ccctggccgc cgcatgc                                      2187
```

<210> SEQ ID NO 10
<211> LENGTH: 426
<212> TYPE: DNA
<213> ORGANISM: Mycobacteria tuberculosis

<400> SEQUENCE: 10

```
atggccggac tgaacattta cgtgaggcgc tggcggacag cgcttcacgc aaccgtgtcg     60

gcattgatag ttgccatcct cggactcgcc atcaccccgg tcgctagtgc ggcgacggcc    120
```

-continued agggcgacgt tgtcggtgac atcgacgtgg cagaccggtt tcatcgcccg cttcaccatc 180
acaaactcga gcacggcgcc gctaaccgat tggaagcttg aattcgactt gccggcagga 240
gaatccgtct tgcacacatg gaatagcacc gttgcacgat ctggcacgca ctacgttctc 300
agcccagcga attggaatcg catcattgcc cccggtggtt cagccacggg cggcctaaga 360
ggcgggctga ccggttctta ctcgccgccg tcgagttgtc tgctcaacgg gcaatatcct 420
tgcacc 426

<210> SEQ ID NO 11
<211> LENGTH: 597
<212> TYPE: DNA
<213> ORGANISM: Mycobacteria tuberculosis

<400> SEQUENCE: 11
gtgaactcac cactggtcgt cggcttcctg gcctgcttca cgctgatcgc cgcgattggc 60
gcgcagaacg cattcgtgct gcggcaggga atccagcgtg agcacgtgct gccggtggtg 120
gcgctgtgca cggtgtccga catcgtgctg atcgccgccg gtatcgcggg gttcggcgca 180
ttgatcggcg cacatccgcg tgcgctcaat gtcgtcaagt ttggcggcgc cgccttccta 240
atcggctacg ggctacttgc ggcccggcgg gcgtggcgac ctgttgcgct gatcccatct 300
ggcgccacgc cggttcgctt agccgaggtc ctggtgacct gtgcggcatt cacgttcctc 360
aacccacacg tctacctcga caccgtcgtg ttgctaggcg cgctggccaa cgagcacagc 420
gaccagcgct ggctgttcgg cctcggcgcg gtcacagcca gtgcggtatg gttcgccacc 480
ctcgggttcg gagccggccg gttgcgcggg ctgttcacca accccggctc gtggagaatc 540
ctcgacggcc tgatcgcggt catgatggtt gcgctgggaa tctcgctgac cgtgacc 597

<210> SEQ ID NO 12
<211> LENGTH: 909
<212> TYPE: DNA
<213> ORGANISM: Mycobacteria tuberculosis

<400> SEQUENCE: 12
atggtggatc cgcagcttga cggtccacag ctggccgcat tggctgccgt ggtcgaactg 60
ggcagcttcg atgcggccgc ggagcgccta catgtcaccc cgtcggctgt cagtcagcgc 120
atcaagtcgt tggagcagca ggtcggccag gtgctggtgg tcagggaaaa gccatgtcgg 180
gcgacgaccg caggtatccc gctgttgcgg ttggccgcgc aaacagcgtt gctcgagtcc 240
gaggcgctcg ctgaaatggg tggcaacgcg tcgctgaaac gcacgcggat caccattgcg 300
gtaaacgccg attccatggc gacatggttt tcggccgtgt tcgacggtct cggcgacgtc 360
ctgctcgacg ttcggatcga ggaccaggac cattccgcgc ggctgctacg ggagggtgtg 420
gcgatgggcg cggtgaccac cgagcggaac ccggtgccgg gctgccgggt gcacccgctg 480
ggtgaaatgc gctacctacc agtggccagc aggccattcg tccagcgcca tctatccgac 540
gggttcactg ccgccgcggc ggctaaagct ccgtcactgg cgtggaatcg tgacgatggg 600
ctgcaggaca tgttggtgcg taaggccttt cgtcgcgcca tcaccagacc gacgcacttt 660
gtcccgacca cagagggctt caccgccgca gcgcgcgccg ggctgggatg ggcatgttc 720 cccgagaagc tggcagcatc tccgcttgcc gatggatcgt tcgtacgggt ctgcgacata 780
cacctcgacg tccctctcta ttggcaatgc tggaaactgg acagtccgat catcgcgcga 840
attaccgaca cggtgagggc ggcggcaagc ggtctgtacc ggggccagca acgccgccgc 900

-continued

```
cgaccgggt                                                          909

<210> SEQ ID NO 13
<211> LENGTH: 651
<212> TYPE: DNA
<213> ORGANISM: Mycobacteria tuberculosis

<400> SEQUENCE: 13

atgactccac gcagccttgt tcgcatcgtt ggtgtcgtgg ttgcgacgac cttggcgctg    60

gtgagcgcac ccgccggcgg tcgtgccgcg catgcggatc cgtgttcgga catcgcggtc   120

gttttcgctc gcggcacgca tcaggcttct ggtcttggcg acgtcggtga ggcgttcgtc   180

gactcgctta cctcgcaagt tggcgggcgg tcgattgggg tctacgcggt gaactaccca   240

gcaagcgacg actaccgcgc gagcgcgtca aacggttccg atgatgcgag cgcccacatc   300

cagcgcaccg tcgccagctg cccgaacacc aggattgtgc ttggtggcta ttcgcagggt   360

gcgacggtca tcgatttgtc cacctcggcg atgccgcccg cggtggcaga tcatgtcgcc   420

gctgtcgccc ttttcggcga gccatccagt ggtttctcca gcatgttgtg gggcggcggg   480

tcgttgccga caatcggtcc gctgtatagc tctaagacca taaacttgtg tgctcccgac   540

gatccaatat gcaccggagg cggcaatatt atggcgcatg tttcgtatgt tcagtcgggg   600

atgacaagcc aggcggcgac attcgcggcg aacaggctcg atcacgccgg a            651

<210> SEQ ID NO 14
<211> LENGTH: 1674
<212> TYPE: DNA
<213> ORGANISM: Mycobacteria tuberculosis

<400> SEQUENCE: 14

gtgtcatttc tggtcgtggt tcccgagttc ttgacgtccg cggcagcgga tgtggagaac    60

ataggttcca cactgcgcgc ggcgaatgcc gcggctgccg cctcgaccac cgcgcttgcg   120

gccgctggcg ctgatgaggt atcggcggcg gtggcagcgc tgtttgccag gttcggtcag   180

gaatatcaag cggtcagcgc gcaggcgagc gctttccatc aacagttcgt gcagacgctg   240

aactcggcgt caggatcgta tgcggccgcg gaggccacca tcgcgtcaca gttgcagacc   300

gcgcagcacg atctgctggg cgcggtcaat gcaccaaccg aaacgttgtt ggggcgtccg   360

ctaatcggcg acggagcacc cgggacggca acgagtccga atggcggggc gggtgggctg   420

ctgtacggca acggcggcaa cggttattcc gcgacggcgt cgggggtcgg cggcggggcc   480

ggcggttccg cggggttgat cggcaatggc ggcgccgggg gagccggcgg acccaacgcc   540

cccgggggag ccggcggcaa cggtggctgg ctgctcggca acggcgggat cggcgggccc   600

gggggcgcgt cgagcatccc cggcatgagt ggtggagccg gcggaaccgg cggtgccgca   660

ggacttttgg gctggggagc gaacggcgga gccggcggcc tcggtgatgg agtcggtgtc   720

gatcgtggca cgggcggcgc cggaggccgc ggcggcctgt tgtatggcgg atacggcgtc   780

agtgggccag gcggcgacgg cagaaccgtc ccgctggaga taattcatgt cacagagccg   840

acggtacatg ccaacgtcaa cggcggaccg acgtcaacca ttctggtcga caccggatcc   900

gctggtcttg ttgtctcgcc tgaggatgtc gggggaatcc tgggagtgct tcacatgggc   960

ctcccaaccg gattgagcat cagcggttac agcgggggggc tgtactacat cttcgccacg  1020

tataccacga cggtggactt cgggaatggc atcgtcaccg cgccgaccgc cgttaatgtc  1080

gtcctcttgt ccatcccaac gtccccctttc gccatttcga cctacttcag cgccttgctg  1140

gccgatccga caacaactcc gttcgaagcc tatttcggtg ccgtcggcgt ggacggcgtt  1200
```

-continued

```
ctgggagttg ggcccaatgc ggtgggacca ggccccagca ttccgacgat ggcgttaccg   1260

ggtgacctca accagggagt gctcatcgac gcacccgcag gtgagctcgt gttcggtccc   1320

aacccgctac ctgcgcccaa cgtcgaggtc gtcggatcgc cgatcaccac cctgtacgta   1380

aagatcgatg gtgggactcc catacccgtc ccctcgatca tcgattccgg tggggtaacg   1440

ggaaccatcc cgtcatatgt catcggatcc ggaaccctgc cggcgaacac aaacattgag   1500

gtctacacca gccccggcgg tgatcggctc tacgcgttca acacaaacga ttaccgcccg   1560

accgtcattt catccggcct gatgaatacc gggttcttgc ccttcagatt ccagccggtg   1620

tacatcgact acagccccag cggtataggg acaacagtct ttgatcatcc ggcg         1674
```

```
<210> SEQ ID NO 15
<211> LENGTH: 1674
<212> TYPE: DNA
<213> ORGANISM: M. tuberculosis

<400> SEQUENCE: 15

gtgtcatttc tggtcgtggt tcccgagttc ttgacgtccg cggcagcgga tgtggagaac     60

ataggttcca cactgcgcgc ggcgaatgcc gcggctgccg cctcgaccac cgcgcttgcg    120

gccgctggcg ctgatgaggt atcggcggcg gtggcagcgc tgtttgccag gttcggtcag    180

gaatatcaag cggtcagcgc gcaggcgagc gctttccatc aacagttcgt gcagacgctg    240

aactcggcgt caggatcgta tgcggccgcg gaggccacca tcgcgtcaca gttgcagacc    300

gcgcagcacg atctgctggg cgcggtcaat gcaccaaccg aaacgttgtt ggggcgtccg    360

ctaatcggcg acggagcacc cgggacggca acgagtccga atggcggggc gggtgggctg    420

ctgtacggca acggcggcaa cggttattcc gcgacggcgt cgggggtcgg cggcggggcc    480

ggcggttccg cggggttgat cggcaatggc ggcgccgggg gagccggcgg acccaacgcc    540

cccgggggag ccggcggcaa cggtggctgg ctgctcggca acggcgggat cggcgggccc    600

gggggcgcgt cgagcatccc cggcatgagt ggtggagccg gcggaaccgg cggtgccgca    660

ggacttttgg gctggggagc gaacggcgga gccggcggcc tcggtgatgg agtcggtgtc    720

gatcgtggca cgggcggcgc cggaggccgc ggcggcctgt tgtatggcgg atacggcgtc    780

agtgggccag gcggcgacgg cagaaccgtc ccgctggaga taattcatgt cacagagccg    840

acggtacatg ccaacgtcaa cggcggaccg acgtcaacca ttctggtcga caccggatcc    900

gctggtcttg ttgtctcgcc tgaggatgtc gggggaatcc tgggagtgct tcacatgggc    960

ctcccaaccg gattgagcat cagcggttac agcgggggc tgtactacat cttcgccacg   1020

tataccacga cggtggactt cgggaatggc atcgtcaccg cgccgaccgc cgttaatgtc   1080

gtcctcttgt ccatcccaac gtccccttc gccatttcga cctacttcag cgccttgctg   1140

gccgatccga caacaactcc gttcgaagcc tatttcggtg ccgtcggcgt ggacggcgtt   1200

ctgggagttg ggcccaatgc ggtgggacca ggccccagca ttccgacgat ggcgttaccg   1260

ggtgacctca accagggagt gctcatcgac gcacccgcag gtgagctcgt gttcggtccc   1320

aacccgctac ctgcgcccaa cgtcgaggtc gtcggatcgc cgatcaccac cctgtacgta   1380

aagatcgatg gtgggactcc catacccgtc ccctcgatca tcgattccgg tggggtaacg   1440

ggaaccatcc cgtcatatgt catcggatcc ggaaccctgc cggcgaacac aaacattgag   1500

gtctacacca gccccggcgg tgatcggctc tacgcgttca acacaaacga ttaccgcccg   1560

accgtcattt catccggcct gatgaatacc gggttcttgc ccttcagatt ccagccggtg   1620
```

tacatcgact acagccccag cggtataggg acaacagtct ttgatcatcc ggcg 1674

<210> SEQ ID NO 16
<211> LENGTH: 417
<212> TYPE: DNA
<213> ORGANISM: Mycobacteria tuberculosis

<400> SEQUENCE: 16
atgatcgtgg acacaagcgc cgtggtggcc ctggttcaag gcgagcggcc gcacgccacc 60
ctggtcgcgg ccgccctggc cggcgcccat agccccgtca tgtctgcacc caccgtcgcc 120
gaatgcctga ttgtcttgac cgcccgtcac ggccccgttg cgcgcacgat cttcgaacga 180
cttcgcagcg aaatcggctt gagcgtgtca tctttcaccg ccgagcatgc cgctgccacg 240
caacgagcct ttctgcgata cggcaagggg cgccaccgcg cggctctcaa cttcggagac 300
tgtatgacgt acgcgaccgc ccagctgggc caccaaccac tgctggccgt cggcaacgac 360
ttcccgcaaa ccgaccttga gttccgcggc gtcgtcggct actggccagg cgtcgcg 417

<210> SEQ ID NO 17
<211> LENGTH: 684
<212> TYPE: DNA
<213> ORGANISM: M. tuberculosis

<400> SEQUENCE: 17
gtgcgcatca agatcttcat gctggtcacg gctgtcgttt tgctctgttg ttcgggtgtg 60
gccacggccg cgcccaagac ctactgcgag gagttgaaag gcaccgatac cggccaggcg 120
tgccagattc aaatgtccga cccggcctac aacatcaaca tcagcctgcc cagttactac 180
cccgaccaga agtcgctgga aaattacatc gcccagacgc gcgacaagtt cctcagcgcg 240
gccacatcgt ccactccacg cgaagccccc tacgaattga atatcacctc ggccacatac 300
cagtccgcga taccgccgcg tggtacgcag gccgtggtgc tcaaggtcta ccagaacgcc 360
ggcggcacgc acccaacgac cacgtacaag gccttcgatt gggaccaggc ctatcgcaag 420
ccaatcacct atgacacgct gtggcaggct gacaccgatc cgctgccagt cgtcttcccc 480
attgtgcaag gtgaactgag caagcagacc ggacaacagg tatcgatagc gccgaatgcc 540
ggcttggacc cggtgaatta tcagaacttc gcagtcacga acgacggggt gattttcttc 600
ttcaacccgg gggagttgct gcccgaagca gccggcccaa cccaggtatt ggtcccacgt 660
tccgcgatcg actcgatgct ggcc 684

<210> SEQ ID NO 18
<211> LENGTH: 684
<212> TYPE: DNA
<213> ORGANISM: M. tuberculosis

<400> SEQUENCE: 18
gtgcgcatca agatcttcat gctggtcacg gctgtcgttt tgctctgttg ttcgggtgtg 60
gccacggccg cgcccaagac ctactgcgag gagttgaaag gcaccgatac cggccaggcg 120
tgccagattc aaatgtccga cccggcctac aacatcaaca tcagcctgcc cagttactac 180
cccgaccaga agtcgctgga aaattacatc gcccagacgc gcgacaagtt cctcagcgcg 240
gccacatcgt ccactccacg cgaagccccc tacgaattga atatcacctc ggccacatac 300
cagtccgcga taccgccgcg tggtacgcag gccgtggtgc tcaaggtcta ccagaacgcc 360
ggcggcacgc acccaacgac cacgtacaag gccttcgatt gggaccaggc ctatcgcaag 420
ccaatcacct atgacacgct gtggcaggct gacaccgatc cgctgccagt cgtcttcccc 480

-continued

```
attgtgcaag gtgaactgag caagcagacc ggacaacagg tatcgatagc gccgaatgcc    540

ggcttggacc cggtgaatta tcagaacttc gcagtcacga acgacggggt gattttcttc    600

ttcaacccgg gggagttgct gcccgaagca gccggcccaa cccaggtatt ggtcccacgt    660

tccgcgatcg actcgatgct ggcc                                           684
```

<210> SEQ ID NO 19
<211> LENGTH: 1443
<212> TYPE: DNA
<213> ORGANISM: Mycobacteria tuberculosis

<400> SEQUENCE: 19

```
gtggtcggcc cgcggacgag aggatatgcg atccacaagc tgggtttctg cagcgtcgtc     60

atgctcggga tcaactcgat aatcggcgcc ggtatcttcc taactccagg tgaggtgatc    120

gggctcgcag gacccttcgc gccgatggcc tatgttttag ctggcatttt cgcgggtgtc    180

gtggcgatcg tcttcgcgac ggcggcaagg tacgtcagaa caaacggtgc ctcctacgcc    240

tacacaacgg ccgcatttgg gcgccggatc ggcatctatg tcggtgtcac ccacgccatt    300

accgcgtcca tcgcttgggg ggtgttggct tctttttcg tctcgacgct gttgcgagtg    360

gccttccccg acaaggcctg ggccgacgcc gagcaactgt tcagtgtgaa gacgctgacg    420

tttctcggct ttatcggcgt gctgttggcc atcaacctct tcggcaaccg ggcgatcaag    480

tgggccaacg gaacgtcaac ggtaggcaag gcattcgcgc tctcggcatt cattgtcggc    540

gggctgtgga tcatcaccac ccagcacgtg aacaactacg caacggcgtg gtcggcatac    600

agcgcgaccc cgtactcgtt gcttggcgtc gccgaaattg gcaagggcac gttctcgagt    660

atggcgctgg ccacgattgt cgcgttgtac gcattcaccg gtttcgaatc gatcgcgaac    720

gccgccgaag aaatggacgc gccggaccgg aacctgccga gagctatacc gatcgcgatc    780

ttctcggttg gcgcgatcta cttgctcacc ctaacggtag cgatgctgct cggatcgaac    840

aagatcgccg cgtcggacga caccgtgaaa ctggccgcgg ccatcggaaa cgctaccttc    900

cgaacgatca tcgtcgtcgg agccctgata tcgatgttcg gcatcaatgt cgcggcctcg    960

ttcggtgcac cgcggctttg gaccgcgtta gcggacagcg gggttctgcc gacacgcttg   1020

tcacgcaaga accaatacga cgtgccgatg gtctccttcg caattacggc gtcgttggcg   1080

ctcgcattcc cgttggcgct gcggttcgac aacctgcacc tgaccggcct ggcggtgatc   1140

gcccgattcg tccagttcat catcgtgccg atcgctctca tcgcattggc gaggtctcag   1200

gcagtagaac atgctgctgt gcggcgaaat gcgttcaccg acaaggtgtt accgcttgtt   1260

gcgatcgtgg tctcggttgg gctggcagtg tcctacgact accgctgcat ctttctagtg   1320

cggggtggtc cgaactactt ctcgattgct ttgatcgtga tcacgttcgt cgtggtaccg   1380

gcgatggctt atctgcacta ctaccgaatc attcgccggg ttggcgatcg gccgagcact   1440

cgc                                                                 1443
```

<210> SEQ ID NO 20
<211> LENGTH: 846
<212> TYPE: DNA
<213> ORGANISM: Mycobacteria tuberculosis

<400> SEQUENCE: 20

```
atgggtgagg cgaacatccg cgagcaggcg atcgccacga tgccacgggg tggccccgac     60

gcgtcttggc tggatcgtcg attccagacc gacgcactgg agtacctcga ccgcgacgat    120
```

-continued

```
gtgcccgatg aggtcaaaca gaagatcatc ggggtgctcg accgggtggg caccctgacc    180

aacctgcacg agaagtacgc ccggatagcc ctgaaacttg tttctgacat tcccaacccg    240

cgaatcctgg aacttggtgc gggccatggc aagctctcag cgaaaatcct cgagctacac    300

ccgacagcga cggtgacgat cagcgatcta gatcccacct cggtggccaa catcgccgcg    360

ggagagctgg gaacacatcc gcgagcacgc acccaagtga tcgacgccac cgcaatcgac    420

ggccacgacc acagctatga cctggcggtc ttcgcgctgg catttcacca cctgccgcct    480

acggtcgcct gcaaagcgat cgccgaggcc acccgggtgg ggaagcgctt tctgatcatc    540

gacctcaaac ggcagaaacc gctgtcgttc acgctctctt cggtgctgct actgccgctc    600

cacctactgc tgctgccatg gtcgtcgatg cgctcgagca tgcacgacgg ctttatcagc    660

gcactacgtg cctacagtcc ctcggcgttg cagacgcttg cccgcgccgc cgatccggga    720

atgcaggttg aaatcttgcc cgcaccgacc aggctattcc cgccatcgct cgccgttgtg    780

ttctcccgtt cgagctcagc gccaacggaa tctagcgagt gctcggccga tcgccaaccc    840

ggcgaa                                                               846
```

<210> SEQ ID NO 21
<211> LENGTH: 1407
<212> TYPE: DNA
<213> ORGANISM: Mycobacteria tuberculosis

<400> SEQUENCE: 21

```
gtgagataca ctacacctgt gcgtgctgct gtctacctcc gaatctcaga agaccgctcc     60

ggcgaacagc tcggcgtggc ccgccaacgc gaggactgcc taaagctgtg cgggcagcga    120

aaatgggtgc ccgtcgagta cctcgacaac gacgtcagcg catcaaccgg caagcgccgc    180

cccgcctacg agcagatgtt ggccgacatc accgccggca agatcgccgc cgtggtggcc    240

tgggacctgg accggctcca tcgccgtccc atcgagctgg aagccttcat gtcattagcc    300

gacgagaagc ggctggccct ggccaccgtc gccggcgacg ttgacctggc gacaccccag    360

ggccggctag tcgcccgcct gaaggggtcg gtggccgctc acgaaaccga gcacaagaag    420

gcacgacagc gccgcgccgc ccgccagaaa gctgaacgcg gccaccccaa ctggtcgaaa    480

gccttcggct acctgcccgg ccccaacggt cccgaacccg acccccggac agcgccgctg    540

gtcaaacagg cctacgccga catcctcgcc ggggcgtccc tgggcgacgt gtgccgccag    600

tggaacgacg ccggggcgtt caccatcacc ggccgcccgt ggacgactac aacgctgtcg    660

aaattcttgc gcaaaccccg caacgccgga ctacgcgcat ataagggtgc ccgctacggc    720

ccggtggacc gcgacgcgat tgtcggcaag gcccagtggt cgccgctggt ggacgaggcg    780

acgttctggg ccgcccaggc cgtgctggac gcccccggcc gcgcccccgg ccgcaaaagc    840

gtgcgccgcc acctgctgac cgggctggca ggctgcggca aatgcggcaa ccacctggcc    900

ggcagctacc gcaccgacgg ccaggtcgtc tacgtgtgca aggcgtgcca cggggtggcc    960

atcctggccg acaacatcga accgatcctg tatcacatcg tggccgagcg gctggccatg   1020

cccgacgccg ttgacttgtt gcgccgggag attcacgacg ccgccgaagc cgaaaccatc   1080

cgcctggaac tggaaaccct ctacggggag ctggacaggc tcgccgtcga acgcgccgaa   1140

gggctactga ccgcgcgcca ggtgaagatc agcaccgaca tcgtcaacgc caagataacg   1200

aaacttcagg cccgccaaca ggatcaggaa cggctccgag tgttcgacgg gataccgttg   1260

ggaacaccgc aagtcgccgg gatgatagcc gagctgtcgc cggaccggtt ccgcgccgtc   1320

ctcgacgtcc tcgctgaagt cgttgtccag ccggtcggca agagcggcag gatattcaat   1380
```

-continued cccgaacggg tgcaggtgaa ttggcga 1407

<210> SEQ ID NO 22
<211> LENGTH: 513
<212> TYPE: DNA
<213> ORGANISM: M. tuberculosis

<400> SEQUENCE: 22
atgagccggc accacaacat cgtgatcgtc tgtgaccacg gccgcaaagg cgatggccgc 60
atcgaacacg agcgctgcga tcttgtcgcg ccgatcattt gggtcgacga gacccagggc 120
tggttaccgc aggcgccagc ggtggcaaca ttactcgacg acgacaacca gccgcgagcc 180
gttattggct tgccgcccaa cgagtctcgc ctacgacctg aaatgcgccg cgacgggtgg 240
gtgcggctgc actgggaatt cgcctgcctg aggtacggcg ccgccggcgt gcgcacgtgc 300
gagcagcggc ccgtgcgggt tcgcaacggc gacctgcaaa cactgtgcga gaacgttccg 360
cggctactga ccggactggc cggcaacccc gactacgcac cgggttttgc ggtgcagtcg 420
gacgcggtgg tcgtcgccat gtggctgtgg cgcacgctct gcgaaagcga cacgccgaac 480
aaactacgcg ccaccccaac gcgtggtagc tgc 513

<210> SEQ ID NO 23
<211> LENGTH: 219
<212> TYPE: DNA
<213> ORGANISM: M. tuberculosis

<400> SEQUENCE: 23
gtgtcgacca tctaccatca tcgcggccgc gtagccgcac tgtctcgttc ccgcgcatcc 60
gacgatcccg agttcatcgc cgcgaaaacc gatctcgttg ccgcgaacat cgcggactac 120
ctcatccgca ccctcgccgc agcgccgccc ctgactgacg agcagcgcac ccggctggcc 180
gagctgctgc gccccgtgcg gcggtcaggc ggtgcccga 219

<210> SEQ ID NO 24
<211> LENGTH: 396
<212> TYPE: DNA
<213> ORGANISM: Mycobacteria tuberculosis

<400> SEQUENCE: 24
atgaccgccg gcgccggcgg gtcgccgccg acgcgacgat gcccggccac ggaggaccgg 60
gcacccgcga cagtcgccac accgtctagc gccgatccta ccgcgtcacg cgccgtgtcg 120
tggtggtcgg tgcacgagca tgtcgcgccg gtcctggatg ctgccgggtc gtggccgatg 180
gccggcacac cggcctggcg tcagctcgac gacgccgatc ctcgcaaatg ggccgcgatc 240
tgcgacgcag cccggcactg ggctctgagg gtagagacgt gccaggaggc gatggcgcag 300
gcgtcacgtg acgtatctgc ggccgccgac tggcccggca tcgcccgcga gatcgtccga 360
cggcgcggcg tgtacatccc gcgggcgggg gtggcg 396

<210> SEQ ID NO 25
<211> LENGTH: 1413
<212> TYPE: DNA
<213> ORGANISM: Mycobacteria tuberculosis

<400> SEQUENCE: 25
atggccgaca tcccctacgg caccgactat cccgacgccc cctggatcga ccgggacggg 60
cacgtgctca tcgacgacgg tggcaaaccg acgcaagttc atcgcggcca agcccgaatc 120

-continued

```
gcctaccggc tagccgaacg ttaccaggac aagctgctgc acgtggccgg gatcggctgg    180

cactcctggg acggcagacg ctgggcagcc gacgaccgcg gcgaagccaa acgtgcagtg    240

ctggcagagc tgcgccaagc gctctcagac agcctcaacg acaaggaatt acgcgccgac    300

gtccgaaaat gcgaatcggc gtccggcgtg gccggcgtgc tcgacctggc cgccgcactg    360

gtaccattcg ccgcgacggt agccgacctc gacagcgacc cgcacttgct caacgtcgcg    420

aatgggacgc tggacctgca cacgctcaaa ttgcggcccc acgcgcccgc tgaccgcatc    480

acaaagatat gccgcggtgc ctaccagtcc gacaccgaat cgcctctctg gcaagcgttc    540

ttgacccgcg ttctgcccga tgaaggtgtg cgcgggttcg tgcaacgcct ggccggcgtc    600

ggcctactag gcaccgtccg cgaacatgtc ctggcgattc ttatcggtgt aggtgccaac    660

ggaaaatctg tgttcgacaa ggcgattcgc tatgcccttg gcgattatgc ctgcaccgct    720

gagcctgacc ttttcatgca ccgggaaaac gctcacccaa caggcgaaat ggacctccgc    780

ggcgtgcgat gggtagcggt atccgagagc gaaaaagatc gccggctggc cgaatcaacg    840

ataaaacggc tgactggcgg cgacaccatc cgcgcccgaa agatgcggca agacttcgtg    900

gaattcacgc cgtcacatac cccactgctc atcaccaacc acctaccgag agtgcccggc    960

gatgatacgg ccatctggcg gcgaattcga gtggtgccgt ttgaagtagt gattcctgcc   1020

gacgagcagg accgggaact ggacgcacgg ttgcagttgg aggccgacag catcctgtcc   1080

tgggcggtgg ccggatggag cgactatcag cgaatcggac tatcccagcc ggacgcggtg   1140

ctcgcggcaa cgtcgaatta ccgcgaggac tccgacacga taaagaggtt catcgacgac   1200

gaatgcgtca ccagctcgcc ggtgctgaaa gccactacta cgcatctgtt cgaggcgtgg   1260

caaaggtggc gggtgcaaga aggcgtaccc gaaatctcgc gcaaagcgtt cggccagtcg   1320

ctcgacaccc acggataccc ggtcactgac aaggcccgtg atggtcgttg gcgggccgga   1380

atagcggtga gaggggccga tgatttcgat gat                                1413
```

<210> SEQ ID NO 26
<211> LENGTH: 393
<212> TYPE: DNA
<213> ORGANISM: Mycobacteria tuberculosis

<400> SEQUENCE: 26

```
atgaccgctg tcgcgatcac cccggcatcc ggcggtcggc acagcgtccg attcgcctac     60

gactctgcga tcgtgtcgtt gatcaagtcc acgatccccg cctatgcccg ctcctggtcc    120

gcgcacaccc gctgctggtt catcgacgct gactggaccc cactgctggc cgccgagctg    180

cgctaccacg gccacaccgt caccggaccc gccgacccgg cgcaacagca gtgcaccgac    240

tgggccaaag cgttgttccg ggcggtcgga ccccagcgga cacccgccgt gtacagggct    300

ttatccaaag tgctgcaccc cgacgcccca accggatgcc cgatactgca acagcagctc    360

aatgccgcca gaaccgcact taccaaccct gct                                 393
```

<210> SEQ ID NO 27
<211> LENGTH: 270
<212> TYPE: DNA
<213> ORGANISM: Mycobacteria tuberculosis

<400> SEQUENCE: 27

```
atggctgaaa cccccgacca cgccgaactg cggcgacgaa tcgccgacat ggctttcaac     60

gccgatgtcg gtatggcgac ctgcaaacgc tgtggtgacg ccgtgccgta catcatcctg    120

ccgaacctgc agaccggcga acccgtcatg ggtgtcgccg acaacaaatg gaagcgcgcg    180
```

```
aactgtcccg tcgacgtcgg taagccgtgc ccgttcctaa tcgccgaggg tgtcgccgac    240

agcaccgacg acaccataga ggtcgaccag                                     270
```

<210> SEQ ID NO 28
<211> LENGTH: 312
<212> TYPE: DNA
<213> ORGANISM: Mycobacteria tuberculosis

<400> SEQUENCE: 28

```
gtgaccccga tcaaccggcc cctgaccaac gacgaacgac aactgatgca cgagctggca     60

gtccaggttg tctgctcgca gacgggttgc tcacccgatg cggcggtcga agcactcgaa    120

tccttcgcga aagacggaac acttatcctc cgcggcgaca ccgagaacgc ctacctcgaa    180

gccggaggca atgttcttgt ccatgccgat cgtgactggc ttgccttcca cgcgtcgtat    240

cccggcaacg acccgctgcg agacgcccga cctatcgagc aggacgacga ccagggggcg    300

gggtcgccat cg                                                        312
```

<210> SEQ ID NO 29
<211> LENGTH: 468
<212> TYPE: DNA
<213> ORGANISM: Mycobacteria tuberculosis

<400> SEQUENCE: 29

```
atgccaagac caccgaaacc ggcccggctc aaactggttg agggccgctc cccggccgc     60

gattccggcg gccggaaagt ccccgagtcg ccgaagttta tccgtcaggc accggatgcc    120

ccggactggc tcgacgccga ggcgctggcc gaatggcggc gcgtcgcacc gactttggag    180

cggcttgacc tgctcaaacc tgaggatcgg gcgctcctgt ccgcgtactg cgagacctgg    240

tccgtctacg tcgcggcggt tcagcgggtc cgcgccgaag gcctcacaat tacctcaccg    300

aaatccggtg tcgtgcaccg gaacccggcg gtgacggttg cggagacggc gcgcatgcat    360

ctgctgcgct tggcctccga gtttggcctg accccggccg ccgagcagcg actggcggtg    420

gcgccgggcg acgacggcga cgggctcaac ccgtttgccc cggaccgg                 468
```

<210> SEQ ID NO 30
<211> LENGTH: 510
<212> TYPE: DNA
<213> ORGANISM: Mycobacteria tuberculosis

<400> SEQUENCE: 30

```
atggccgagc tgcggtctgg cgaaggccga accgtgcacg gcaccatcgt gccctacaac     60

gaggcgacca ccgtccgcga cttcgacggc gagttccagg aaatgttcgc tcctggcgct    120

tttcggcgct ccatcgccga gcgcggccac aaattgaagc tgctggtctc tcacgacgct    180

cgaacccgct acccggtggg ccgggccgtt gagttgcggg aggagcctca cggcttgttc    240

ggggcgttcg agattgcgga caccccggac ggcgacgagg ctttggcgaa cgtaaaagct    300

ggtgtcgtcg actcgttttc ggtgggtttc cgaccgatcc gggaccgtcg cgaaggggat    360

gtgctggtgc gcgtcgaagc ggcgctgtta gaggtttccc taaccggcgt tccggcctat    420

tcgggggcac aaatcgccgg ggtgcgcgcg gaatcgctta cagtcgtttc ccgttcgaca    480

gccgaagcct ggctgtccct actcgattgg                                     510
```

<210> SEQ ID NO 31
<211> LENGTH: 1419
<212> TYPE: DNA

-continued

<213> ORGANISM: Mycobacteria tuberculosis

<400> SEQUENCE: 31

```
atgaccgaat tcgacgacat caaaaacctc tctttacctg aaacccgtga cgcggcgaag     60
cagctcctcg acagtgtcgc cggcgacctg accggtgagg cggcgcagcg ttttcaggcg    120
ctgacgcgcc acgccgagga actgcgggcg gagcagcgcc gccgcggccg cgaagccgag    180
gaggcgctgc gccgctaccg ggccggtgag ctgagggtgg tgcccggcgc tcccaccggc    240
ggcgacgacg gcgacgcgcc gccgggcaac tcgttgcggg acaccgcgtt tcgcacactg    300
gattcttgtg tgcgagacgg cctgatgtcg tcgcgggcgg cggagaccgc ggaaaccttg    360
tgccgcaccg ggccgccgca gtccacctcg tgggcgcagc gctggctggc ggccaccggc    420
agccgcgact atttgggcgc gttcgtcaag cgggtttcca atcctgttgc ggggcacacg    480
gtttggaccg accgggaagc ggccgcgtgg cgtgaggctg ccgcggtggc cgccgagcag    540
cgagcgatgg gcctggtgga cacccaaggc gggtttctga tcccggcggc gctggacccg    600
gcgatcctgc tgtcgggtga tgggtcgacg aacccgattc ggcaggtggc gagggtggtg    660
caaacgacct ccgagatttg gcggggcgtg acttccgaag gcgccgaagc tcgttggtac    720
tccgaagccc aggaggtgtc cgacgattcg ccagcgttgg cccagccggc ggtgccgaac    780
taccgtggaa gctgctggat tccgttctcc atcgagctgg agggtgacgc ggcgagcttc    840
gttggcgaga tcggcaagat tctcgcggac agcgttgagc aactgcaggc cgcggcgttc    900
gtcaacggct ccggcaacgg cgagcccacc gggttcgtca gcgcgctaac cggcacctcc    960
gatcaggtgg tcgtcggcgc ggggtcagaa gcgattgtgg cggcggatgt ttacgcgttg   1020
cagtcggcgc tgccgccaag gttccaggcc agcgccgcgt tcgcggcgaa cttgtccacc   1080
atcaacacgt tgcggcaggc ggaaacttcg aatggcgcgc tgaaattccc atcgctgcac   1140
gacagtccgc cgatgctagc cgggaagtct gtcctggaag tctcccacat ggacaccgtt   1200
gattcggcgg tgacagcgac gaatcatcca ctggtgcttg gcgactggaa gcaattcctc   1260
atcggcgaca gagttgggtc catggtggag ttggtgcctc acctgttcgg gccgaatcgc   1320
cggccgaccg ggcagcgcgg attcttcgcc tggttcaggg tcggatcaga tgtgctggtg   1380
cgcaacgcgt ttcgagttct gaaggtggag actaccgcg                           1419
```

<210> SEQ ID NO 32
<211> LENGTH: 351
<212> TYPE: DNA
<213> ORGANISM: Mycobacteria tuberculosis

<400> SEQUENCE: 32

```
atggcgccgc tggccgccgg atcgccgagc tggaacggcc gaaagccaag cagcggcaac     60
aggaaggcgg cgaccatggc cgccaggctc gatattctgg cttggggccc atgggcccca    120
agccagaatc ggagcgtcgt tcgacgaaaa cagacactgc tatcggcgca gccctcggca    180
tctccgccgg cacctaccgg cggctcaaac gaatcgacaa cgcaacccgc agcgagttgg    240
cgcgtgggcg gcccggcacc cctaagcaga ggccgcccac gcctggccct atcctaccta    300
cgcggtagtc tccaccttca gaactcgaaa cgcgttgcgc accagcacat c             351
```

<210> SEQ ID NO 33
<211> LENGTH: 309
<212> TYPE: DNA
<213> ORGANISM: Mycobacteria tuburculosis

<400> SEQUENCE: 33

```
atgggctaca aaccagaatc agagcgtcat tcgacgaaaa cagacactgc tatcggcgca     60
gccctcggca tctccgccgg cacctaccgg cggctcaaac gaatcgacaa cgcaacccac    120
agcgacgaca aagaaatccg ccggttcgcg gagaaacaaa tggcgccgct ggtcgccgga    180
tcgccgagct ggaacgcccg aaagccaagg agcgccaacg cgagggtggt cgcctcggtg    240
catcgatcac caatgccggc tttggtccca tggaaccaaa gccgtctcag cgccacactg    300
acaaggagg                                                            309

<210> SEQ ID NO 34
<211> LENGTH: 408
<212> TYPE: DNA
<213> ORGANISM: Mycobacteria tuburculosis

<400> SEQUENCE: 34

atgaccacca caccagcacg tttcaaccac ttggtgacgg taaccgacct ggaaacgggt     60
gaccgcgccg tctgcgaccg cgaccaggtg gccgagacga tccgggcgtg gttcccggac    120
gcgcccttgg aggtgaggga agcgctcgtt cggctgcagg ccgcgttgaa tcggcacgag    180
cacaccggcg agctcgaagc gttcctgcgg atcagcgtcg agcacgccga cgccgccggc    240
ggcgacgagt gcggcccggc gatcctggcc ggccgctccg ggccggaaca agccgccatc    300
aaccggcaac tcggactcgc cggcgacgac gagcccgacg gcgacgacac cccgccgtgg    360
agccggatga tcgggcttgg cggcggaagc ccagcggaag acgagcgc                 408

<210> SEQ ID NO 35
<211> LENGTH: 1407
<212> TYPE: DNA
<213> ORGANISM: Mycobacteria tuburculosis

<400> SEQUENCE: 35

gtgaaacggc tcagcggctg ggacgcggta ctgctttaca gcgagacccc gaatgtgcac     60
atgcacacac tcaaggtcgc cgtgatcgaa ttggattcgg acagacagga attcggtgtc    120
gacgcgtttc gcgaggtgat cgctggccgg ctgcataagc ttgagccatt gggctatcag    180
ctggttgatg tcccgttgaa gttccatcac ccgatgtggc gggagcactg ccaggtcgat    240
ctcaactacc acatccggcc gtggcggttg cgcgccccgg ggggtcggcg cgaactcgac    300
gaggcggtcg gagaaatcgc cagcaccccg ctgaaccgcg accacccgct gtgggagatg    360
tacttcgttg aggggcttgc caaccaccgg atcgcggtgg ttgccaaaat tcaccatgcg    420
ttggctgacg gtgttgcctc ggcaaacatg atggcacggg ggatggatct gctgccggga    480
ccggaggtcg gccgctatgt gcctgacccc gctcctacca agcggcagtt gctgtccgcg    540
gcgttcatcg accacttgcg ccacctcggc cggattcctg caaccatccg gtacaccacg    600
cagggtctag gccgggtgcg acgtagctcg cgcaagctct cacccgcact gaccatgcca    660
tttaccccgc caccgacgtt catgaatcac cggctcaccc cggagcgcag gttcgccacc    720
gccaccctgg cgctgattga cgtgaaggcg acggccaagt tgctgggggc gacgatcaac    780
gacatggtgc tggccatgtc gaccggcgct ctgcgtaccc tgctattgcg ctatgacggc    840
aaggccgaac cgctgctggc gtcggtcccg gtgagttacg acttctcacc ggagcggatc    900
tccggtaacc gcttcaccgg aatgctggtg gcgctgcctg ccgactccga cgacccgttg    960
cagcgggtgc gcgtctgtca cgaaaacgcg gtctccgcca aggagagcca ccagcttttg   1020
ggaccggagt tgatcagccg ctgggcggct tactggccac ctgccggtgc ggaagccttg   1080
```

-continued

```
ttccggtggt tgtctgagcg cgacgggcag aacaaggtac tcaacttgaa tatctcgaat   1140

gttcccggtc cgcgcgaacg cggccgcgtg gggccgcgc tggtcaccga gatctattcg   1200

gtgggcccgt tgaccgccgg tagcggattg aatatcacgg tgtggagtta tgtcgatcag   1260

ctcaatatct cggtgttaac cgatggttcc accgtgcagg acccgcatga agtaaccgcg   1320

ggaatgatcg cggacttcat cgaaatacgc cgcgccgctg gtctttccgt ggagttgaca   1380

gtcgtcgagt ccgcgatggc gcaggca                                        1407
```

<210> SEQ ID NO 36
<211> LENGTH: 786
<212> TYPE: DNA
<213> ORGANISM: Mycobacteria tuburculosis

<400> SEQUENCE: 36

```
atgagcagcg aaagcgacgc agccaacacc gaacctgagg ttctggtaga acagcgggat     60

cggattttga tcatcacgat caaccgcccg aaagccaaga acgcggtcaa cgccgcagtc    120

agccggggct tggccgatgc gatggatcag cttgacggcg atgccggcct gtcggtggca    180

atcctgaccg gtgggggcgg ttcgttctgc gcgggcatgg acctcaaggc gttcgcccgg    240

ggcgagaatg tcgtcgtcga aggtcgcggc cttggcttta ccgaacgtcc gccgaccaag    300

ccgctcattg ctgcggtgga aggctacgcg ttggcgggtg gcaccgagct ggcgcttgct    360

gccgacctga tcgtggcggc cagggattcg gcgttcggga ttcctgaagt caagcggggt    420

ctggttgccg gcggcggggg attgctgcgg ttgccggagc gcatcccgta tgcgatagcc    480

atggagttgg cgctgaccgg tgacaaccta ccggccgaac gcgcgcacga gctggggctc    540

gtcaacgttt tggccgagcc ggggaccgcc ctcgatgctg cgatcgcgtt ggcggagaag    600

atcaccgcca atgggccgct ggcggtggtg gccaccaagc ggattatcac cgagtcgcgt    660

gggtggagtc ccgacactat gttcgctgag cagatgaaga tcctggtgcc ggtgttcacc    720

tccaacgacg cgaaggaagg tgcgatcgcg ttcgccgaga ggcgccggcc ccgttggacg    780

ggcacc                                                               786
```

<210> SEQ ID NO 37
<211> LENGTH: 1461
<212> TYPE: DNA
<213> ORGANISM: M. tuberculosis

<400> SEQUENCE: 37

```
atgtctgaca gtgccacgga atacgacaag cttttcatcg gcggcaagtg gaccaaaccg     60

tcgacctccg atgttatcga ggtacgctgc ccagccactg ggaatatgt cggcaaggtg    120

ccgatggcgg ccgccgccga cgtcgacgcc gcggtcgccg cagcacgtgc ggcgttcgac    180

aacggcccct ggccctcgac ccgccgcac gagcgtgcgg cggtgatcgc tgcggcggtc    240

aagatgctgg ctgagcgcaa ggacctgttc accaagctgc tcgcagccga aaccggccag    300

ccgccgacca tcatcgagac gatgcactgg atgggttcga tgggggcgat gaactacttt    360

gccggtgcag cggacaaggt cacctggacc gaaacccgca ccggctccta tggacagagc    420

attgtcagcc gtgagccggt cggtgtggtg ggcgcgatcg tggcctggaa cgtcccgctg    480

tttctggccg tcaacaagat tgcgccggcg ctgctggccg gctgcaccat cgtgctcaag    540

cccgccgccg aaacaccgct gaccgcaaac gctttggcgg aggtgttcgc cgaggtgggc    600

ctgcccgagg gggtgttgtc ggtagtgccg ggagggattg agaccggtca ggcgctgacg    660

tctaacccgg acatcgacat gtttaccttc accggcagct cggccgtcgg ccgagaggtc    720
```

```
ggcaggcgtg ccgctgagat gctcaagccg tgcaccttag aactcggcgg caagtcggcg    780

gccatcattc tcgaggacgt cgacctggcc gcagctattc cgatgatggt gttctccggc    840

gtcatgaacg ccggacaggg ctgcgtcaac cagacccgca ttctggctcc gcgctcccgg    900

tacgacgaaa tcgtggctgc ggtaactaat ttcgtaacgg ctctcccggt gggcccgccg    960

tcggacccgg cagctcagat cgggccgctg atctcggaga agcagcggac tcgcgttgaa   1020

ggctacatcg ccaagggcat cgaggagggc gctcggttgg tgtgcggcgg cggccgtccc   1080

gagggcttgg acaacggctt ctttatccaa cccaccgtat tcgccgatgt cgacaacaag   1140

atgaccatcg cacaggagga gatcttcggg ccggtgctgg ccatcattcc ttatgacacc   1200

gaggaggacg cgatcgcgat cgccaacgat tcagtgtatg ggctggcggg cagcgtgtgg   1260

accaccgacg tgcccaaagg catcaagatc tcgcagcaga tccgcaccgg gacatacgga   1320

atcaactggt acgccttcga tcccggctca cccttcggcg gctacaagaa ctccggaatc   1380

ggccgcgaga acgggcccga gggtgtcgaa cacttcaccc agcaaaagag tgtcctgctg   1440

ccgatgggct acaccgtcgc g                                              1461
```

```
<210> SEQ ID NO 38
<211> LENGTH: 831
<212> TYPE: DNA
<213> ORGANISM: M. tuberculosis

<400> SEQUENCE: 38

atggcacgct gcgatgtcct ggtctccgcc gactgggctg agagcaatct gcacgcgccg     60

aaggtcgttt tcgtcgaagt ggacgaggac accagtgcat atgaccgtga ccatattgcc    120

ggcgcgatca agttggactg gcgcaccgac ctgcaggatc cggtcaaacg tgacttcgtc    180

gacgcccagc aattctccaa gctgctgtcc gagcgtggca tcgccaacga ggacacggtg    240

atcctgtacg gcggcaacaa caattggttc gccgcctacg cgtactggta tttcaagctc    300

tacggccatg agaaggtcaa gttgctcgac ggcggccgca agaagtggga gctcgacgga    360

cgcccgctgt ccagcgaccc ggtcagccgg ccggtgacct cctacaccgc ctccccgccg    420

gataacacga ttcgggcatt ccgcgacgag gtcctggcgg ccatcaacgt caagaacctc    480

atcgacgtgc gctctcccga cgagttctcc ggcaagatcc tggcccccgc gcacctgccg    540

caggaacaaa gccagcggcc cggacacatt cctggtgcca tcaacgtgcc gtggagcagg    600

gccgccaacg aggacggcac cttcaagtcc gatgaggagt tggccaagct ttacgccgac    660

gccggcctag acaacagcaa ggaaacgatt gcctactgcc gaatcgggga acggtcctcg    720

cacacctggt tcgtgttgcg ggaattactc ggacaccaaa acgtcaagaa ctacgacggc    780

agttggacag aatacggctc cctggtgggc gccccgatcg agttgggaag c             831
```

```
<210> SEQ ID NO 39
<211> LENGTH: 300
<212> TYPE: DNA
<213> ORGANISM: M. tuberculosis

<400> SEQUENCE: 39

atgtgctctg gacccaagca aggactgaca ttgccggcca gcgtcgacct ggaaaaagaa     60

acggtgatca ccggccgcgt agtggacggt gacggccagg ccgtgggcgg cgcgttcgtg    120

cggctgctgg actcctccga cgagttcacc gcggaggtcg tcgcgtcggc caccggcgat    180

ttccggttct tcgccgcgcc cggatcctgg acgctgcgcg cgctgtcggc ggccggcaac    240
```

-continued

```
ggcgacgcgg tggtgcagcc ctcgggcgcg ggcatccacg aggtagacgt caagatcacc    300

<210> SEQ ID NO 40
<211> LENGTH: 441
<212> TYPE: DNA
<213> ORGANISM: M. tuberculosis

<400> SEQUENCE: 40

atggccaatg tggtagctga aggtgcctac ccttactgtc ggctcactga tcagccgctg     60

agtgtggacg aagtgctagc cgccgtctcg ggccccgaac aaggcggcat tgtcatattt    120

gtgggaaacg tgcgtgacca caatgccggg catgatgtca cgcggttgtt ctacgaggcg    180

tatccgccga tggtgattcg gacattgatg tcgatcatcg gacggtgtga agacaaggcc    240

gagggtgtcc gcgttgctgt cgcgcaccgg accggtgaat tgcaaatcgg tgatgccgcg    300

gtcgttattg gcgcgtcagc tccccaccgt gcggaggcat ttgacgccgc gcgtatgtgt    360

atcgagttgc ttaagcagga agtgccgatt tggaagaagg aattcagctc gaccggtgct    420

gaatgggtcg gcgatagacc a                                              441

<210> SEQ ID NO 41
<211> LENGTH: 600
<212> TYPE: DNA
<213> ORGANISM: M. tuberculosis

<400> SEQUENCE: 41

atgagtccgt ctccatcggc cctgctcgcc gaccacccgg accgcattcg ttggaacgcg     60

aaatacgagt gcgctgaccc cacggaggcg gtatttgcgc ccatatcctg gctcggcgac    120

gtgctgcagt tcggggtgcc agaagggccg gttctggaac tggcgtgcgg tcggtccggc    180

accgcgctgg ggctagccgc ggcgggccgc tgcgtgactg cgatcgacgt ttccgatacc    240

gcgttggttc agctcgagct cgaagcgacc cgacgggaat tggccgatcg cctcacactg    300

gtgcacgccg atctctgctc ctggcagtcg ggggatggac gctttgctct ggtactttgc    360

cgactattct ggcatccgcc cacttttcgc caggcttgcg aggctgtggc gccgggcggt    420

gtagtggcgt gggaggcatg gcggcggccc atcgatgtcg ctcgggatac ccgtcgagcc    480

gaatggtgct tgaagccagg ccagcccgag tctgaacttc ccgccggctt cacggtgatt    540

cgggtggtcg acaccgatgg ttcagagccg tcgcggcgca tcatcgccca acggtcactg    600

<210> SEQ ID NO 42
<211> LENGTH: 1200
<212> TYPE: DNA
<213> ORGANISM: Mycobacteria tuburculosis

<400> SEQUENCE: 42

atgacaagca cctcgattcc gacgttcccg ttcgaccggc cggtcccgac ggagccgtcc     60

ccaatgctgt cggaactgag aaacagctgt ccggtagccc cgatagagtt gccctcgggg    120

cacacagcat ggctcgtcac tcgctttgac gatgtaaagg gagtgctgtc cgacaagcgt    180

ttcagctgca gggcggcagc gcacccgtcg tcgcccccgt tcgtgccgtt cgtgcagctt    240

tgccccagct tgttgagcat cgatgggccc caacacaccg cggcccgccg tctgctcgcg    300

cagggcctaa atcccggctt catcgcacgc atgcggcccg ttgtccaaca gatcgtcgac    360

aatgcgctcg acgatctggc agccgcggaa ccaccggtgg acttccagga aatagtaagt    420

gtccctatcg gagaacagct catggccaag ctactcgggg tcgagcccaa aaccgtgcac    480

gagctcgcgg cgcacgtgga tgcggcgatg tccgtgtgtg agatcggcga cgaggaggtg    540
```

-continued agccggcggt ggtcagcact gtgcacgatg gtcatcgaca tactgcaccg caagctcgcc 600
gaaccgggtg atgacctact tagcacgatc gcccaggcga accggcaaca gtccaccatg 660
accgacgagc aggttgtcgg catgctcctc accgtcgtga tcggaggagt cgacacaccg 720
atcgccgtga tcacaaacgg gctggcgagc ctgctgcacc accgcgatca atatgaacgg 780
ctcgttgaag acccaggccg tgtcgctcgt gcggttgaag aaatagtccg gtttaatccg 840
gcaactgaaa ttgagcactt gcgagttgtc accgaggatg tcgtcattgc cggaaccgcg 900
ctatcggcgg ggagcccagc atttacctct atcacttcgg ctaaccgcga ctccgaccaa 960
ttcctggacc ccgatgagtt tgatgtcgaa cgtaatccga acgaacacat agcatttgga 1020
tatggtccac atgcttgccc ggcctcagcg tattcacgca tgtgcttgac gacgttcttc 1080
acctcgctta cccagcgatt tccgcaactt caactcgcaa gaccgtttga ggatttggaa 1140
cgacggggta agggcctaca ttcggtgggg atcaaggaac tccttgttac ctggccgacg 1200

<210> SEQ ID NO 43
<211> LENGTH: 498
<212> TYPE: DNA
<213> ORGANISM: Mycobacteria tuburculosis

<400> SEQUENCE: 43
gtgcgcattg tcaatgcggc ggacccattt tcgatcaacg atctaggctg tggctatggg 60
gctctactgg actacctaga tgcgcgtggc ttcaaaactg attacaccgg catcgacgtc 120
tcccccgaaa tggtgcgcgc ggccgcacta cgtttcgaag gtcgggcgaa cgcagacttc 180
atctgcgcgg cgcgcataga tcgggaggcg gactatagcg tcgcgagtgg aatattcaat 240
gttcgtctga aatcgttgga cacggaatgg tgcgctcaca tcgaagcgac gctcgacatg 300
ctgaatgccg cgagtcgccg tggcttctct tttaattgcc tgacatctta ttccgatgca 360
tcaaagatgc gcgacgacct gtactatgct gacccatgcg ccctatttga tctctgcaag 420
cgcaggtact ccaagagtgt tgcgcttctg cacgactacg gcttgtatga attcacaatt 480
ctggttagga aggcgtca 498

<210> SEQ ID NO 44
<211> LENGTH: 693
<212> TYPE: DNA
<213> ORGANISM: Mycobacteria tuburculosis

<400> SEQUENCE: 44
ttgaagaaag tcgcgattgt tcaatcaaat tacatacctt ggcgaggata ttttgacctg 60
attgcattcg tcgatgaatt catcatctat gatgacatgc aatataccaa gcgtgattgg 120
cgaaacagaa atcggatcaa aacgagccag ggttacagt ggataactgt tcccgtccag 180
gtgaagggac gtttccatca aaagatacgt gagacgctga tcgacggcac cgattgggcg 240
aaagcgcact ggcgggcact agaattcaac tacagcgcgg ccgctcattt tgcggagatc 300
gctgactggc tcgcgccgat ttacctcgaa gaacagcaca cgaatctttc cttactcaac 360
aggcgtctat tgaatgcgat ttgcagttat ctcggtatca gcacgcgact ggcaaattcg 420
tgggactacg aattagccga cggcaagacc gagagactgg ccaacctctg ccaacaggcc 480
gcagcgaccg aatatgtctc tggcccctca gcccgttcgt atgtcgatga gcgcgtgttc 540
gacgaactta gcatccgggt aacttggttc gattatgacg gctaccgcga ttataagcaa 600
ttgtggggag ggttcgagcc cgccgtgtcg attctggatc tgctctttaa cgtcggagcc 660

-continued

```
gaggctccgg actatttgag gtactgtcgc cag                               693


<210> SEQ ID NO 45
<211> LENGTH: 395
<212> TYPE: DNA
<213> ORGANISM: Mycobacteria tuburculosis
<220> FEATURE:
<221> NAME/KEY: misc_feature
<222> LOCATION: (1)...(395)
<223> OTHER INFORMATION: n = A,T,C or G
<221> NAME/KEY: misc_feature
<222> LOCATION: 27, 44, 104, 119, 180, 224, 237, 245, 254, 301, 327,
      370, 385, 393
<223> OTHER INFORMATION: n = A,T,C or G

<400> SEQUENCE: 45

vvmsartgva rhgtsgrgcg dvgargndvs vatrkrsrgd rvgnhgarar rmkrvrgavt     60

asrrwagssr tmgtasvsaa tayaswyavd vstvvgdcwd wgmngrhcsd yamvaaagna    120

dysadytava awaaryagsh wgargcyvat mavsawaarg argrvvvtga aaawgvdrgn    180

stgvvaayva srrwgattva vvkvvgvvaa rwrwaggtgv vvsnaawrgg tashgknssg    240

grdrnvsgka dsknysgkgt grtgavvvvv avagrrvmvg vatatsadva yyvvaavard    300

nggagdaahg drrravgvcv savasvnvav gyvyggakgv vgttvttvtw awvtcvvvsy    360

arkarhdshn gtrsddtaas ttscnvssrg gcnyt                              395


<210> SEQ ID NO 46
<211> LENGTH: 879
<212> TYPE: DNA
<213> ORGANISM: Mycobacteria tuburculosis

<400> SEQUENCE: 46

gtgtttgcgt tgagtaataa tctgaaccgt gtgaacgcat gcatggatgg attccttgcc     60

cgtatccgct cacatgttga tgcgcacgcg ccagaattgc gttcactgtt cgatacgatg    120

gcggccgagg cccgatttgc acgcgactgg ctgtccgagg acctcgcgcg gttgcctgtc    180

ggtgcagcat tgctggaagt gggcgggggg gtacttctgc tcagctgtca actggcggcg    240

gagggatttg acatcaccgc catcgagccg acgggtgaag gttttggcaa gttcagacag    300

cttggcgaca tcgtgctgga attggctgca gcacgaccca ccatcgcgcc atgcaaggcg    360

gaagacttta tttccgagaa gcggttcgac ttcgccttct cgctgaatgt gatggagcac    420

atcgaccttc cggatgaggc agtcaggcgg gtatcggaag tgctgaaacc gggggccagt    480

taccacttcc tgtgcccgaa ttacgtattc ccgtacgaac cgcatttcaa tatcccaaca    540

ttcttcacca aagagctgac atgccgggtg atgcgacatc gcatcgaggg caatacgggc    600

atggatgacc cgaagggagt ctggcgttcg ctcaactgga ttacggttcc caaggtgaaa    660

cgctttgcgg cgaaggatgc gacgctgacc ttgcgcttcc accgtgcaat gttggtatgg    720

atgctggaac gcgcgctgac ggataaggaa ttcgctggtc gccgggcaca atggatggtc    780

gctgctattc gctcggcggt gaaattgcgt gtgcatcatc tggcaggcta tgttcccgct    840

acgctgcagc ccatcatgga tgtgcggcta acgaagagg                           879


<210> SEQ ID NO 47
<211> LENGTH: 1296
<212> TYPE: DNA
<213> ORGANISM: Mycobacteria tuburculosis

<400> SEQUENCE: 47

atgtacgaga gacggcatga gcgcggaatg tgcgaccgtg ccgtcgagat gaccgacgtc     60
```

-continued

```
ggcgctacgg cagcccccac cggacctatc gcgcggggca gcgtcgctcg ggtcggcgcg    120

gcgaccgcgt tggccgttgc ctgcgtctac acggtcatct atctggcggc ccgcgaccta    180

cccccggctt gtttttcgat attcgcggtg ttttgggggg cgctcggcat tgccaccggc    240

gccacccacg gcctcctgca agaaacgacc cgcgaggtcc gctgggtgcg ctccacccaa    300

atagttgcgg gccatcgtac ccatccgctg cgggtggccg ggatgattgg caccgtcgcg    360

gccgtcgtaa ttgcgggtag ctcaccgctg tggagccgac agctattcgt cgaggggcgc    420

tggctgtccg tggggctact cagcgttggg gtggccgggt tctgcgcgca ggcgaccctg    480

ctgggcgcgc tggccggcgt cgaccggtgg acacagtacg ggtcactgat ggtgaccgac    540

gcggtcatcc ggttggcggt cgccgcggca gcggttgtga tcggatgggg tctggccggg    600

tacttgtggg ccgccaccgc gggagcggtg gcgtggctgc tcatgctgat ggcctcgccc    660

accgcgcgca gcgcggccag cctgctgacg cccgggggaa tcgccacgtt cgtgcgcggt    720

gccgctcatt cgataaccgc cgcgggtgcc agcgcgattc tggtaatggg tttcccagtg    780

ttgctcaaag tgacctccga ccagttaggg gcaaagggcg gagcggtcat cctggctgtg    840

accttgacgc gtgcgccgct tctggtccca ctgagcgcga tgcaaggcaa cctgatcgcg    900

catttcgtcg accggcgcac ccaacggctt cgggcgctga tcgcaccggc gctggtcgtc    960

ggcggcatcg gtgcggtcgg gatgttggcc gcagggctta ccggtccctg gttgctgcgt   1020

gttggattcg gccccgacta ccaaactggc ggggcgttgc tggcctggtt gacggcagcg   1080

gcggtagcta tcgccatgct gacgctgacc ggcgccgccg cggtcgcggc cgcactgcac   1140

cgggcgtatt tgctgggctg ggtcagcgcg acggtggcgt cgacgctgtt gctgctgctg   1200

ccgatgccgc tggagacgcg caccgtgatc gcgctgttgt tcggtccaac ggtgggaatc   1260

gccatccatg tggccgcgtt ggcgcggcga cccgac                             1296
```

<210> SEQ ID NO 48
<211> LENGTH: 1020
<212> TYPE: DNA
<213> ORGANISM: M. tuberculosis

<400> SEQUENCE: 48

```
gtgaagcgag cgctcatcac cggaatcacc ggccaggacg gctcgtatct cgccgaactg     60

ctgctggcca aggggtatga ggttcacggg ctcatccggc gcgcttcgac gttcaacacc    120

tcgcggatcg atcacctcta cgtcgacccg caccaaccgg gcgcgcggct gtttctgcac    180

tatggtgacc tgatcgacgg aacccggttg gtgaccctgc tgagcaccat cgaacccgac    240

gaggtgtaca acctggcggc gcagtcacac gtgcgggtga gcttcgacga acccgtgcac    300

accggtgaca ccaccggcat gggatccatg cgactgctgg aagccgttcg gctctctcgg    360

gtgcactgcc gcttctatca ggcgtcctcg tcggagatgt tcggcgcctc gccgccaccg    420

cagaacgagc tgacgccgtt ctacccgcgg tcaccgtatg gcgccgccaa ggtctattcg    480

tactgggcga cccgcaatta tcgcgaagcg tacggattgt tcgccgttaa cggcatcttg    540

ttcaatcacg aatcaccgcg gcgcggtgag acgttcgtga cccgaaagat caccagggcc    600

gtggcacgca tcaaggccgg tatccagtcc gaggtctata tgggcaatct ggatgcggtc    660

cgcgactggg ggtacgcgcc cgaatacgtc gaaggcatgt ggcggatgct gcagaccgac    720

gagcccgacg acttcgtttt ggcgaccggg cgcggtttca ccgtgcgtga gttcgcgcgg    780

gccgcgttcg agcatgccgg tttggactgg cagcagtacg tgaaattcga ccaacgctat    840
```

-continued

```
ctgcggccca ccgaggtgga ttcgctgatc ggcgacgcga ccaaggctgc cgaattgctg    900

ggctggaggg cttcggtgca cactgacgag ttggctcgga tcatggtcga cgcggacatg    960

gcggcgctgg agtgcgaagg caagccgtgg atcgacaagc cgatgatcgc cggccggaca   1020


<210> SEQ ID NO 49
<211> LENGTH: 966
<212> TYPE: DNA
<213> ORGANISM: M. tuberculosis

<400> SEQUENCE: 49

atgaacgcgc acacctcggt cggcccgctt gaccgcgcgg cccgggtcta catcgccggg     60

catcgcggcc tggtcgggtc cgcgctgcta cgcacgtttg cgggcgcggg gttcaccaac    120

ctgctggtgc ggtcacgcgc cgagcttgat ctgacggatc gggccgcgac gttcgacttc    180

gttctcgagt cgaggccgca ggtcgtcatc gacgcggcgg cccgggtcgg cggcatcctg    240

gccaacgaca cctacccggc cgatttcctg tcggaaaacc tccagatcca ggtcaacctg    300

ctggatgccg ccgtggcggc gcgggtgccg cggctgctgt tcctgggctc gtcgtgcatc    360

tacccgaaac tcgccccgca gccgatcccg gagagcgcgc tgctcaccgg tccgttggag    420

ccgaccaacg acgcgtacgc gatcgccaaa atcgccggca tccttgcggt ccaggcggtg    480

cgccgccaac atggcctgcc gtggatctcg gcgatgccca ccaacctgta cgggccaggc    540

gacaactttt cgccgtccgg ctcgcatctg ctgccggcac tcatccgccg ctatgacgag    600

gccaaagcca gtggcgcgcc caacgtgacc aactggggca ccggcacgcc ccgacgggag    660

ttgctgcacg tcgacgacct ggcgagcgca tgcctgtatc tgctggaaca tttcgacggg    720

ccgacccatg tcaacgtggg aaccggcatc gaccacacca tcggcgagat cgccgagatg    780

gtcgcctcgg cggtaggcta tagcggcgaa acccgctggg atccaagcaa accggacgga    840

acaccacgca aactgctgga tgtttcggtg ctacgggagg cgggatggcg gccttcgatc    900

gcgctgcgcg acggcatcga ggcgacggtg gcgtggtatc gcgagcacgc gggaacggtt    960

cggcaa                                                               966


<210> SEQ ID NO 50
<211> LENGTH: 729
<212> TYPE: DNA
<213> ORGANISM: Mycobacteria tuberculosis

<400> SEQUENCE: 50

atgaggctgg cccgtcgcgc tcggaacatc ttgcgtcgca acggcatcga ggtgtcgcgc     60

tactttgccg aactggactg ggaacgcaat ttcttgcgcc aactgcaatc gcatcgggtc    120

agtgccgtgc tcgatgtcgg ggccaattcg gggcagtacg ccaggggtct gcgcggcgcg    180

ggcttcgcgg gccgcatcgt ctcgttcgag ccgctgcccg ggccctttgc cgtcttgcag    240

cgcagcgcct ccacggaccc gttgtgggaa tgccggcgct gtgcgctggg cgatgtcgat    300

ggaaccatct cgatcaacgt cgccggcaac gagggcgcca gcagttccgt cttgccgatg    360

ttgaaacgac atcaggacgc ctttccacca gccaactacg tgggcgccca acgggtgccg    420

atacatcgac tcgattccgt ggctgcagac gttctgcggc ccaacgatat tgcgttcttg    480

aagatcgacg ttcaaggatt cgagaagcag gtgatcgcgg gtggcgattc aacggtgcac    540

gaccgatgcg tcggcatgca gctcgagctg tctttccagc cgttgtacga gggtggcatg    600

ctcatccgcg aggcgctcga tctcgtggat tcgttgggct ttacgctctc gggattgcaa    660

cccggtttca ccgacccccg caacggtcga atgctgcagg ccgatggcat cttcttccgg    720
```

-continued

```
ggcagcgat                                                         729

<210> SEQ ID NO 51
<211> LENGTH: 786
<212> TYPE: DNA
<213> ORGANISM: Mycobacteria tuburculosis

<400> SEQUENCE: 51

gtgacgtctg ctccgaccgt ctcggtgata acgatctcgt tcaacgacct cgacgggttg    60

cagcgcacgg tgaaaagtgt gcgggcgcaa cgctaccggg gacgcatcga gcacatcgta   120

atcgacggtg gcagcggcga cgacgtggtg gcatacctgt ccgggtgtga accaggcttc   180

gcgtattggc agtccgagcc cgacggcggg cggtacgacg cgatgaacca gggcatcgcg   240

cacgcatcgg gtgatctgtt gtggttcttg cactccgccg atcgtttttc cgggcccgac   300

gtggtagccc aggccgtgga ggcgctatcc ggcaagggac cggtgtccga attgtggggc   360

ttcgggatgg atcgtctcgt cgggctcgat cgggtgcgcg gcccgatacc tttcagcctg   420

cgcaaattcc tggccggcaa gcaggttgtt ccgcatcaag catcgttctt cggatcatcg   480

ctggtggcca agatcggtgg ctacgacctt gatttcggga tcgccgccga ccaggaattc   540

atattgcggg ccgcgctggt atgcgagccg gtcacgattc ggtgtgtgct gtgcgagttc   600

gacaccacgg gcgtcggctc gcaccgggaa ccaagcgcgg tcttcggtga tctgcgccgc   660

atgggcgacc ttcatcgccg ctacccgttc gggggaaggc gaatatcaca tgcctaccta   720

cgcggccggg agttctacgc ctacaacagt cgattctggg aaaacgtctt cacgcgaatg   780

tcgaaa                                                            786

<210> SEQ ID NO 52
<211> LENGTH: 894
<212> TYPE: DNA
<213> ORGANISM: Mycobacteria tuburculosis

<400> SEQUENCE: 52

atgtcgacaa acccaggacc agccgaaggg gctaaccaag tgatggcaca ggaacattcg    60

gccggcgcgg tacaattcac cgcccacaac gttcgcctcg acgacggaac cttgacgata   120

ccggagtcct cgcgcacgtt agacgaatcg tcctggttca tctcggcgcg cgggattctg   180

gaaaccgtct ttcccgggga caagagccac ctacgcctgg ccgatgtcgg ctgcttggaa   240

ggcgggtacg cggtcgggtt cgcgcgcatg ggatttcagg tcctcgggat cgaggttcgc   300

gagctgaaca tggcggcctg caactacatc aaatcgaaga ccaacctgcc gaatctccgg   360

ttcgtccacg acaacgccct caacatcgcc aaccacgggc tcttcgatac cgtcttctgc   420

tgcggcctct tctaccacct ggagaatccg aagcaatacc tggaaaccct ctcgtcggta   480

acgaacaagc tgctgattct ccagacgcac ttctcgatca tcaaccggag cgataaatgg   540

ctccggttgc ccacgacggc acgacaattg accgatcggt tgctgcggcg gccggcgccg   600

gtgaagttca tgctctcggc gcccaccgaa catgagggac ttcccggtag gtggtttacc   660

gagttttccg acgaccgctc gtttggccag cgcgacaccg caaaatgggc gtcctgggac   720

aatcgccggt cattctggat tcaacgcgag cacctacttc aggccatcaa agacgtcggc   780

gtcgacctgg tgatggagga gtacgacaac ttggaaccaa gcatcgccga gtcgttgctc   840

ggaggttcct atgcggcgaa tcttcgaggc accttcatcg gtatcaagac ccgg         894

<210> SEQ ID NO 53
```

-continued

<211> LENGTH: 1119
<212> TYPE: DNA
<213> ORGANISM: Mycobacteria tuburculosis

<400> SEQUENCE: 53

```
gtgccgtacg tccgccgacc accaggccac gacggccgac ggccggcggg cacaggcgat     60
tcacgttcgc catcgcaata cccttgcggc cgcgcaggaa aagggccgac ggtgagtccc    120
cagctttgcc ccaaggtgag catcgtctcg accactcaca accaggcggg ctacgcccgt    180
caggccttcg acagctttct cgaccagcaa accgacttcc cggtggagat catcgtcgcc    240
gacgacgcgt cgaccgatgc caccccggcg atcatccgtg agtacgccga gcggtacccg    300
cacgtgttcc ggccgatctt caggaccgaa aacctcggcc tcaatgggaa cctgaccggc    360
gccctgtcgg ccgctcgcgg cgagtacgtc gcgttgtgcg aggcggacga ctactggatc    420
gatccgctga agctaagcaa acaggtcgca ttcctcgacc ggcaccccaa gacgacggtg    480
tgcttccatc ccgtccgagt gatatgggag gacggccatg ccaaggactc gaagttcccc    540
ccggttcggg tgcggggcaa cttgagcctg gatgcgttga tcttgatgaa cttcatccag    600
accaactcgg ccgtgtaccg tcgcctcgag cgctacgacg acattcctgc cgacgtcatg    660
cccctggact ggtatctgca cgtccggcac gcggtgcatg gcgacatcgc catgttgccc    720
gacaccatgg ccgtgtatcg ccgccacgcc caaggcatgt ggcacaacca ggtggtggac    780
ccgccaaagt tctggttgac gcagggtccg gggcatgcgg cgacgtttga cgcgatgctc    840
gacctgttcc cgggagaccc cgcgcgcgag gagctcatcg ccgtcatggc cgactggatc    900
cttcgccaga tcgccaacgt tccaggcccg gaggggcgcg ccgcgctgca ggaaaccatc    960
gcgcgccatc cccggatcgc catgctggcg ctgcagcacc gcggggcgac acccgcgcgg   1020
cggctcaaga cccagtggcg caagctcgcc gccgcgacgc cgagccgcag gggctcgtg    1080
gatgtgtggc cctcccggct ccgacgcggc tgtcgagcc                          1119
```

<210> SEQ ID NO 54
<211> LENGTH: 282
<212> TYPE: DNA
<213> ORGANISM: Mycobacteria tuburculosis

<400> SEQUENCE: 54

```
atgaccatca actatcagtt cggtgatgtc gacgctcatg gcgccatgat ccgcgctcag     60
gccgggttgc tggaggcgga gcatcaggcc atcgttcgtg atgtgttggc cgcgggtgac    120
ttttggggcg gcgccggttc ggtggcttgc caggagttca tcacccagct gggccgtaac    180
ttccaggtga tctacgagca ggccaacgcc cacgggcaga aggtgcaggc tgccggcaac    240
aacatggcac aaaccgacag cgccgtcggc tccagctggg cc                       282
```

<210> SEQ ID NO 55
<211> LENGTH: 294
<212> TYPE: DNA
<213> ORGANISM: Mycobacteria tuburculosis

<400> SEQUENCE: 55

```
atggcaacac gttttatgac ggatccgcac gcgatgcggg acatggcggg ccgttttgag     60
gtgcacgccc agacggtgga ggacgaggct cgccggatgt gggcgtccgc gcaaaacatc    120
tcgggcgcgg gctggagtgg catggccgag gcgacctcgc tagacaccat ggcccagatg    180
aatcaggcgt ttcgcaacat cgtgaacatg ctgcacgggg tgcgtgacgg gctggttcgc    240
gacgccaaca actacgagca gcaagagcag gcctcccagc agatcctcag cagc          294
```

<210> SEQ ID NO 56
<211> LENGTH: 324
<212> TYPE: DNA
<213> ORGANISM: Mycobacteria tuburculosis

<400> SEQUENCE: 56
gtgcttttgc ctcttggtcc gcctttgccg cccgacgcgg tggtggcgaa acgggctgag 60
tcgggaatgc tcggcgggtt gtcggttccg ctcagctggg gagtggctgt gccacccgat 120
gattatgacc actgggcgcc tgcgccggag gacggcgccg atgtcgatgt ccaggcggcc 180
gaaggggcgg acgcagaggc cgcggccatg gacgagtggg atgagtggca ggcgtggaac 240
gagtgggtgg cggagaacgc tgaaccccgc tttgaggtgc cacggagtag cagcagcgtg 300
attccgcatt ctccggcggc cggc 324

<210> SEQ ID NO 57
<211> LENGTH: 1524
<212> TYPE: DNA
<213> ORGANISM: M. tuberculosis

<400> SEQUENCE: 57
atgtcacgcc gagcattcct ggctaaggcg gctggagccg gggcagcggc ggttttgacg 60
gactgggccg caccggtgat cgaaaaggcc tatggtgccg gtccctgctc gggtcatttg 120
accgatatcg agcacatcgt gctgtgccta caggagaaca ggtcgttcga tcactatttc 180
ggcacgcttt ctgccgtcga cgggttcgac actccgacgc cgctgtttca acaaaagggc 240
tggaacccgg agacgcaggc gctggacccc accggcatta cgctgcccta ccgcatcaat 300
accaccgggg gtcccaacgg ggttggcgag tgcgtcaacg acccagacca ccagtggatt 360
gccgcgcact tgtcatggaa cggcggcgcc aatgacggct ggctgccggc gcaggcgcgg 420
acccggtcgg tggccaacac gcccgtggtg atgggctatt acgcacgtcc tgacataccg 480
atccactact tgttggccga taccttcacg atctgcgacc agtacttctc gtcgcttctt 540
ggcgggacga tgcctaaccg gctctattgg atcagcgcca ccgtcaatcc cgacggggat 600
caaggtgggc cgcagatcgt cgaacccgcc atccagccga agttgacctt cacctggcgc 660
atcatgccgc agaacctcag tgacgccggc atcagttgga aggtgtacaa cagcaagctg 720
ctcggcgggc tcaacgacac ttccttgagc cgtaacgggt atgtgggcag tttcaaacag 780
gccgcagatc cgaggtcgga cctggcccgt tatggcatcg ccccggccta cccgtgggat 840
ttcatccgcg acgtcatcaa caacacgctg ccccaggtgt cctgggtcgt tccgttgacc 900
gtcgagtccg aacatccgtc attcccggtg gcagtcggtg cggtgacgat cgtgaacttg 960
ataagggtgt tgctgcgcaa tccggcggtg tgggagaaaa ccgcgttgat catcgcctat 1020
gacgaacatg gcggcttctt cgaccacgtc acaccgctca ccgcgccgga gggcacaccc 1080
ggcgaatgga ttcccaacag tgttgacatc gacaaggtcg acggctccgg cggaatacgt 1140
ggacccatcg gcttgggctt tcgcgtgccc tgcttcgtca tttcgcctta cagtcgcggc 1200
gggctgatgg tccatgatcg gttcgaccac acatcgcagc tgcaattgat cggcaagcgt 1260
ttcggggtgc cggttcccaa cttgacaccc tggcgtgcca gtgtcaccgg cgatatgacg 1320
tcggcattca atttcgcggc cccgccggac ccgtcgccac ccaatctgga ccacccggtc 1380
cgtcaattgc cgaaggtcgc caagtgcgtg cccaatgtgg tgctgggttt cttgaacgaa 1440
ggcctgccgt atcgggtgcc ctacccccaa acaacgccag tccaggaatc cggtcccgcg 1500

```
cggccgattc ccagcggcat ctgc                                          1524

<210> SEQ ID NO 58
<211> LENGTH: 1536
<212> TYPE: DNA
<213> ORGANISM: M. tuberculosis

<400> SEQUENCE: 58

atgtcacgtc gagagttttt gacaaagctc actggcgcag gcgcagcggc attcctgatg     60

gactgggctg caccggtgat tgaaaaggcc tacggcgccg ggccttgtcc cggacatttg    120

accgacatcg agcatatcgt gttgctgatg caggagaacc ggtcattcga ccactatttc    180

ggaacgcttt ccagcaccaa tgggttcaac gccgcgtcgc cggcattcca acaaatgggt    240

tggaacccca tgacgcaggc gttggacccc gccggggtca ccattccgtt ccgcttggac    300

accacccgag gccccttcct ggacggcgag tgcgtcaacg accccgagca ccagtgggtg    360

gggatgcacc tggcctggaa cggtggtgcc aacgacaact ggctgccggc gcaggcgacc    420

acccgcgcag gaccatatgt ccctttgacc atgggttact acacgcgcca agacatcccg    480

atccactatc tgctggccga cacgttcacc atctgcgacg gctaccattg ctcgctgctg    540

acgggcaccc tgcccaaccg gctctactgg ttgagcgcca acatcgaccc cgccggcacc    600

gacgggggac cccaattggt agagccgggc ttcctgccgc tgcagcaatt cagttggcgc    660

atcatgccgg aaaacctcga agatgccggg gtcagctgga aggtgtacca gaacaagggc    720

ctcgggcgat tcatcaacac gcccatcagc aataacgggc tggtgcaggc cttccgccag    780

gcagctgatc cgaggtcgaa cttggcccgc tacggtatcg ccccgaccta ccctggggac    840

ttcgctgccg acgtcagggc caaccggcta cccaaggtct cctggttagt tcccaacatc    900

ctgcagtccg aacaccccgc cctgccggta gcgcttggcg cggtgtccat ggtgaccgcg    960

ctgcggatct tgctgtccaa tcccgcggtg tgggaaaaga ccgcacttat cgtcagctat   1020

gacgagaacg gcggcttctt cgaccacgtc acgcccccca cggcaccgcc cgggacaccc   1080

ggcgaattcg tcacggtgcc caacatcgac gcagtacccg ggtccggtgg cattcgtggt   1140

ccgctcggtc tgggttttcg cgttccctgc attgtcattt cgccgtacag ccgcggcccg   1200

ctgatggtct ccgacacgtt cgaccacacc tcgcaattga agttgattcg cgcccggttc   1260

ggcgtgccgg ttcccaacat gaccgcctgg cgcgacggcg tggttggcga catgacctca   1320

gcgttcaact ttgcgactcc accgaattcg accagaccca acttgagcca cccgttgctg   1380

ggagcgctgc cgaagctgcc gcagtgcatc cctaacgtgg tgttgggaac caccgacggc   1440

gcgttgccga gcattcccta tcgggtgccc tatccgcagg tgatgccaac tcaggaaacc   1500

acacccgtcc gcgggactcc cagcgggctg tgcagc                             1536

<210> SEQ ID NO 59
<211> LENGTH: 1536
<212> TYPE: DNA
<213> ORGANISM: M. tuberculosis

<400> SEQUENCE: 59

atgtcacgtc gagagttttt gacaaagctc actggcgcag gcgcagcggc attcctgatg     60

gactgggctg caccggtgat tgaaaaggcc tacggcgccg ggccttgtcc cggacatttg    120

accgacatcg agcatatcgt gttgctgatg caggagaacc ggtcattcga ccactatttc    180

ggaacgcttt ccagcaccaa tgggttcaac gccgcgtcgc cggcattcca acaaatgggt    240

tggaacccca tgacgcaggc gttggacccc gccggggtca ccattccgtt ccgcttggac    300
```

-continued

```
accacccgag gccccttcct ggacggcgag tgcgtcaacg accccgagca ccagtgggtg    360

gggatgcacc tggcctggaa cggtggtgcc aacgacaact ggctgccggc gcaggcgacc    420

acccgcgcag gaccatatgt ccctttgacc atgggttact acacgcgcca agacatcccg    480

atccactatc tgctggccga cacgttcacc atctgcgacg gctaccattg ctcgctgctg    540

acgggcaccc tgcccaaccg gctctactgg ttgagcgcca acatcgaccc cgccggcacc    600

gacgggggac cccaattggt agagccgggc ttcctgccgc tgcagcaatt cagttggcgc    660

atcatgccgg aaaacctcga agatgccggg gtcagctgga aggtgtacca gaacaagggc    720

ctcgggcgat tcatcaacac gcccatcagc aataacgggc tggtgcaggc cttccgccag    780

gcagctgatc cgaggtcgaa cttggcccgc tacggtatcg ccccgaccta ccctggggac    840

ttcgctgccg acgtcagggc caaccggcta cccaaggtct cctggttagt tcccaacatc    900

ctgcagtccg aacaccccgc cctgccggta gcgcttggcg cggtgtccat ggtgaccgcg    960

ctgcggatct tgctgtccaa tcccgcggtg tgggaaaaga ccgcacttat cgtcagctat   1020

gacgagaacg gcggcttctt cgaccacgtc acgcccccca cggcaccgcc cgggacaccc   1080

ggcgaattcg tcacggtgcc caacatcgac gcagtacccg ggtccggtgg cattcgtggt   1140

ccgctcggtc tgggttttcg cgttccctgc attgtcattt cgccgtacag ccgcggcccg   1200

ctgatggtct ccgacacgtt cgaccacacc tcgcaattga agttgattcg cgcccggttc   1260

ggcgtgccgg ttcccaacat gaccgcctgg cgcgacggcg tggttggcga catgacctca   1320

gcgttcaact ttgcgactcc accgaattcg accagaccca acttgagcca cccgttgctg   1380

ggagcgctgc cgaagctgcc gcagtgcatc cctaacgtgg tgttgggaac caccgacggc   1440

gcgttgccga gcattcccta tcgggtgccc tatccgcagg tgatgccaac tcaggaaacc   1500

acacccgtcc gcgggactcc cagcgggctg tgcagc                             1536
```

<210> SEQ ID NO 60
<211> LENGTH: 1173
<212> TYPE: DNA
<213> ORGANISM: Mycobacteria tuburculosis

<400> SEQUENCE: 60

```
atgattttgg atttttcgtg gttgccgccg gagatcaact cggcgcggat ctatgccggt     60

gcggggtcgg ggccgttgtt tatggcggcg gcggcgtggg aggggttggc tgcggatttg    120

cgggcctcgg cgtcctcgtt tgatgcggtg atcgccgggt tggcggctgg gccgtggtcg    180

ggtccggcgt cggtggcgat ggcgggggcg gcggcgccgt atgtggggtg gttgagtgcg    240

gcggccgggc aggcggagtt gtcggctggt caggctaccg cggcggcgac ggcgtttgag    300

gcggcgttgg cggccacggt gcatccggcg gcggtgacgg cgaatcgggt gttgttgggg    360

gcgttggtgg cgacgaacat tttgggtcag aacacgccgg cgattgcggc cactgagttc    420

gattatgtgg agatgtgggc tcaggacgtg ggtgcgatgg tggggtatca cgcgggggcg    480

gcggcggtgg ctgagacgtt gacgccgttt agtgtgccgc cgctggattt ggcgggggttg    540

gcttcccagg ccggtgcgca gttgaccggg atggcgacgt cggtttcggc tgcgttgtct    600

ccgatcgcgg agggtgcggt ggagggggtg ccggctgtgg tggctgcggc gcagtcggtg    660

gcggcggggt tgccggtgga tgcggcgctg caggtggggc aggccgcggc gtatccggcc    720

agtatgttga ttgggccgat gatgcagttg gcgcagatgg ggactacggc caacacggct    780

gggttggccg gtgcggaggc tgcggggttg gctgcggcgg atgtgccgac gtttgccggt    840
```

-continued

```
gatatcgctt cggggacggg cctaggtggt gccggtggtc tgggtgcggg gatgtcggcg    900

gagttgggta aggcgcggtt ggtgggggcg atgtcggtgc ctccgacctg ggaggggtcg    960

gttcctgcgc ggatggccag ttcggcgatg gcgggtttgg gggctatgcc tgctgaggtg   1020

ccggcggcag gcgggcccat ggggatgatg ccgatgccga tgggtatggg ggtgctgggg   1080

gcgggtatgc cggccgggat gatgggccgc ggtggcgcaa atccgcatgt ggtgcaggct   1140

cggcccagtg tggtgccgcg ggtcgggatc gga                                1173
```

<210> SEQ ID NO 61
<211> LENGTH: 1062
<212> TYPE: DNA
<213> ORGANISM: Mycobacteria tuburculosis

<400> SEQUENCE: 61

```
atgccggggc ggttcagaaa cttcggtagc caaaacctgg gtagcggcaa catcggcagc     60

accaacgtgg gcagcggcaa catcggcagc accaacgtgg gcagcggcaa catcggcgac    120

acgaacttcg gtaacggaaa caacggcaac ttcaactttg gtagcggcaa taccggcagt    180

aacaacatcg gcttcggaaa caccggcagc gggaatttcg gtttcggaaa cacgggcaac    240

aacaacatcg gtatcgggct caccggcgat ggtcagatcg gcatcggcgg actgaactcg    300

ggcagcggaa acatcggttt cgggaactcc ggcaccggaa acgtcggttt gttcaactcc    360

ggcaccggca acgtaggctt cgggaactcc ggtactgcga acactggatt cgggaacgcg    420

ggcaacgtca acaccggatt ttggaacggc ggcagcacaa acactggcct cgctaacgcc    480

ggcgccggca acacaggctt tttcgacgct ggcaactaca acttcggcag tcttaacgcc    540

ggaaacataa actcgagttt tgggaattcg ggtgacggca acagtggttt cctcaatgct    600

ggcgacgtca actccggtgt gggcaatgcg ggtgatgtca acactggctt agggaactcg    660

ggcaacatca atactggtgg gtttaatccg ggcacgctca acacgggctt cttcagcgcg    720

atgacccaag ctggtccgaa ttcgggcttc ttcaacgccg gtaccggtaa ctctggtttc    780

gggcacaacg acccggctgg cagtggcaac tcgggcattc agaactcggg cttcggcaac    840

tcgggctatg tcaataccag caccacaagc atgttcggcg gtaactcagg ggtgctcaac    900

acgggctacg gcaactcagg tttctataac gcggccgtca acaacaccgg gatttttgtg    960

accggcgtga tgagttcggg atttttcaat tttgggacgg gcaactcggg cctgctggtc   1020

agcggcaatg ggctttcggg tttcttcaag aacttgttcg ga                      1062
```

<210> SEQ ID NO 62
<211> LENGTH: 654
<212> TYPE: DNA
<213> ORGANISM: Mycobacteria tuburculosis

<400> SEQUENCE: 62

```
atgagccgac tcctagcttt gctgtgcgct gcggtatgca cgggctgcgt tgctgtggtt     60

ctcgcgccag tgagcctggc cgtcgtcaac ccgtggttcg cgaactcggt cggcaatgcc    120

actcaggtgg tttcggtggt gggaaccggc ggttcgacgg ccaagatgga tgtctaccaa    180

cgcaccgccg ccggctggca gccgctcaag accggtatca ccacccatat cggttcggcg    240

ggcatggcgc cggaagccaa gagcggatat ccggccactc cgatggggggt ttacagcctg    300

gactccgctt ttggcaccgc gccgaatccc ggtggcgggt tgccgtatac ccaagtcgga    360

cccaatcact ggtggagtgg cgacgacaat agccccacct ttaactccat gcaggtctgt    420

cagaagtccc agtgcccgtt cagcacggcc gacagcgaga acctgcaaat cccgcagtac    480
```

-continued

```
aagcattcgg tcgtgatggg cgtcaacaag gccaaggtcc caggcaaagg ctccgcgttc    540

ttctttcaca ccaccgacgg cgggcccacc gcgggttgtg tggcgatcga cgatgccacg    600

ctggtgcaga tcatccgttg gctgcggcct ggtgcggtga tcgcgatcgc caag          654
```

<210> SEQ ID NO 63
<211> LENGTH: 489
<212> TYPE: DNA
<213> ORGANISM: Mycobacteria tuburculosis

<400> SEQUENCE: 63

```
gtgtgctgca atggcgtggt gactccgggt gatccagccg acattgcagc gatcaaacag     60

ctcaaatacc ggtatctgcg ggcattggac accaagcatt gggacgactt caccgacacc    120

ctggccgagg atgtcaccgg cgattacggg tcatcggtcg gtacggagct gcacttcacc    180

aaccgcgccg acctggtcga ctacctgcgc caggcactcg gcccgggtgt catcaccgaa    240

caccgggtca cccatccgga aatcaccgtg accggcgata ccgcaaccgg catctggtac    300

ctgcaagacc gggtcatcgt cgccgagttc aatttcatgc tcatcggcgc cgcgttctac    360

cacgaccagt accgacgaac caccgacggc tggcggatca gcgccaccgg ctacgaccga    420

acctacgagg cgaccatgtc gttggcgggc cttaacttca acatcaggcc gggccgcgcg    480

ctggccgat                                                            489
```

<210> SEQ ID NO 64
<211> LENGTH: 1227
<212> TYPE: DNA
<213> ORGANISM: Mycobacteria tuburculosis

<400> SEQUENCE: 64

```
atgagccaat cccggtacgc ggggttgtcc cgcagcgagc tggcagttct gttacccgag     60

ctgttgttga tcggccagct gatcgaccga tcgggcatgg cctggtgtat acaggcattc    120

ggccgccagg agatgctgca gatcgccatc gaggagtggg cgggcgccag cccgatctac    180

accaagcgca tgcaaaaggc gctgaacttc gagggcgacg acgtgcccac catcttcaag    240

gggctacagc tcgacatcgg cgcgccgccg caattcatgg acttccgttt caccctgcac    300

gaccgctggc acggcgagtt tcacctcgac cactgcggtg cgctgctcga cgtggagccg    360

atgggcgacg actacgtcgt cggcatgtgc cacaccatcg aagatccgac gttcgacgcc    420

accgcgatcg cgaccaaccc gcgcgcgcag gtgcgcccca tccaccggcc gccccgcaag    480

ccggccgacc ggcatccgca ctgtgcgtgg accgtcatca tcgacgagtc ctatcccgag    540

gctgagggta ttccggcgct ggacgcggtc cgtgaaacca aagctgccac ctgggaatta    600

gacaacgtcg atgcgtctga cgacgggctg gtggactatt cgggtccgct ggtgtccgac    660

ctggacttcg ggcgttctc gcattccgca ctggtgcgga tggccgatga ggtctgcctg     720

caaatgcacc tgctgaatct gtcgttcgcc attgccgtgc ggaaacgggc caaagccgat    780

gctcaactgg ccatttcggt gaacacccgc cagttgatcg gagtggccgg gctgggcgca    840

gaacgcattc accgtgcgat ggctttaccc ggcggaatcg aaggcgcgtt aggtgtgctg    900

gagctacacc cgctgctcaa cccggccggt tacgtgctgg ccgaaacgtc gccggaccgt    960

ctggtggtgc acaactcgcc agcccacgcc gacggcgcct ggatttcgtt gtgcacaccg   1020

gcatccgtgc agccgttgca ggccatcgcc accgctgtag acccgcatct gaaggttcgg   1080

atcagcggga cggacaccga ctggaccgcg gaactcatcg aggccgatgc cccagcgagc   1140
```

-continued

```
gaactgccgg aggtgttggt agccaaggtc agtcgcggat cggtcttcca gttcgagccg   1200

aggcgctcac tgccgttgac cgtgaaa                                         1227
```

<210> SEQ ID NO 65
<211> LENGTH: 1860
<212> TYPE: DNA
<213> ORGANISM: Mycobacteria tuburculosis

<400> SEQUENCE: 65

```
atgtacgacc cgctggggtt gtcgatcggg accacaaacc tggtcgcggc gggtaacgga     60

ggtccgccgg ttactcgtcg cgccgtgctg accctgtacc cgcattgcgc accgaaaatc    120

ggtgtgccta gccagaaccc gaacttgatc gagccgggcg ccctaatgag cggctttgtt    180

gagcgcattg gagatgcggt ggcgctggtg tctcccgacg gatccgtgca cgatccagac    240

ctcttgctgg tcgaggcgct ggatgcgatg gtgctgaccg ccggtgcgga cgcgagttcc    300

tcggagatcg ccattgccgt tcccgcgcat tggaagcccg gagctgtaca cgcactgcgt    360

aacggtttgc ggacgcacgt cggcttcgtc cgcagcggca tggcgccgcg cctggtttcc    420

gatgcgatcg cggcgttgac cgcggtgaac tcggaattgg gcctgcccca cggcagtgtg    480

gtggggttgc ttgatttcgg tggctccgcg acttacgtca ccttggtgga gaccaagtcg    540

gattccagga cgtcggattt ccagcccgtt agtgccacgg cacggtacca ggacttttcc    600

ggtagtcaga tcgaccaggc tttgctgctt cgggtcatcg accaattcgg gtacggcgat    660

gacgtcgatc cggccagtac cgccgcggtc gggcaactcg gccaactcag ggagcagtgc    720

cgtgcggcaa aggaacgact gtccaccgac gttgccacgg aattgttcgc tgagcttgcc    780

gggtgcagct cgagcatcga gatgactcgg gaacagctcg aagacctgat ccaggatcca    840

ttgaccggct tcatctacgc gttcgacgac atgctggcgc gccacaacgc gagctgggcg    900

gatctcgcgg cggtggtcac cgtcggcggt ggtgccaata ttccccttgt gactcaacgt    960

ctttcgttcc acactcgtcg acctgtgctg accgcgtcgc aacccgggtg cgcggcggcg   1020

atgggtgcgt tgctgctcgc caaccgtggg ggagagcgcg attcgcgaac gcggacgtcc   1080

atcggcctcg ccacggccgc agccgccggc accagtgtca tcgagctgcc ggccggcgac   1140

gtcatggtca tcgaccatga ggccttgacc gatcgcgagt tggcctggtc gcagaccgac   1200

ttcccaagcg aagctccggc gcgtttcgag ggcgactcgt ataacgaagg cggcccctgc   1260

tggtcgatgc gtctgaacgc ggtcgagccc cccaaaggac cagcgtggcg gcgaatccgg   1320

gtgtcgcagt tgctcatcgg ggtgtcggcg gtagtggcca tgaccgcgat cgggggcgtg   1380

gcattgacgt tgacagccat cgagagagcg ccaagcccgc taccaacccc aattgtgccc   1440

ggcctggccc cgatgccgcc cggatccgtc gtgcctagct cgcgcgcacc gaccccgccg   1500

ccaccgccgt cgaccgttgc gccgcttccc agtgcggcac cggccccgac gacggtcgcg   1560

ccggcaccgc cgccgcccac acaggtggtg acgaccacga cagcgccacc cgtcaccacg   1620

acgccgaggc cgtcgccgac caccacaacg accaccgcgc caccgtcgac aacgacgaca   1680

accgagccgc cggtgacgac cacttcgacg attccaacga ttccgacgac tacgacgacg   1740

gtgaagatga ccacggagtg gttgcacgtc ccgtttttgc ccgttccgat cccggtcccg   1800

attccgcaaa atccgggtgc cggcgaaccg cagaacccgt tcggaagcct tggctctggg   1860
```

<210> SEQ ID NO 66
<211> LENGTH: 720
<212> TYPE: DNA
<213> ORGANISM: M. tuberculosis

<400> SEQUENCE: 66
atgatccgat tggtccgtca ttcgatcgcc ctggtggccg ccggccttgc cgccgcattg 60
tcggggtgcg attcccacaa ctcgggatcg ctcggtgccg atccgcggca ggtgaccgtg 120
ttcggatccg ggcaagtgca gggtgtgccg gacacgttga tcgctgacgt cggcattcag 180
gtcaccgcgg ccgacgtcac cagcgcgatg aaccagacca atgatcgcca gcaagcggtg 240
atcgatgcac tggtgggtgc cggcctggac cgcaaggaca tccgcaccac cagggtcacc 300
gtggcaccgc agtacagcaa tccggagccg gccggaaccg ccaccatcac cgggtatcgg 360
gcagacaacg acatcgaggt gaagatccac ccgaccgacg ccgcgtcgcg gctgctggcc 420
ctcgtcgtca gcaccggcgg tgacgccacc cggatcagct cggtcagcta ctcgattggc 480
gacgactcgc agctggtgaa ggatgcccgg gcgcgcgcct tccaagacgc caagaaccgt 540
gcggaccagt acgcacaact gtcggggctg cggctaggca aggtgatctc gatctccgag 600
gcatctggcg ccgcgcccac gcacgaggcg ccggcgccgc cgcgcggcct atccgcggtg 660
ccgctggaac ccggccagca gacggtgggc ttctcggtca cggtggtctg ggaactgacc 720

<210> SEQ ID NO 67
<211> LENGTH: 297
<212> TYPE: DNA
<213> ORGANISM: Mycobacteria tuburculosis

<400> SEQUENCE: 67
atgtcgatca tgcacgccga gccagagatg ctggctgcga ccgcggggga actgcagtcg 60
atcaacgccg ttgcgcgggc cggaaatgca gcggtggcgg gcccgacgac gggtgtggtt 120
ccggccgccg ctgatttggt gtccctgcta accgcctccc agtttgccgc gcatgcacag 180
ctgtaccagg cgattagtgc cgaggcgatg gcggtccagg agcagttggc gaccacgctg 240
ggcatcagcg ccggttcata tgcggccacc gaggctgcca acgccgccac gatcgct 297

<210> SEQ ID NO 68
<211> LENGTH: 1239
<212> TYPE: DNA
<213> ORGANISM: Mycobacteria tuburculosis

<400> SEQUENCE: 68
atgctggact ttgctcagtt accgccggag gtcaactccg cgctgatgta cgccggaccc 60
ggttcgggac cgatgctggc tgccgcggcg gcctgggagg cgctggccgc cgagttgcaa 120
accacggcgt ccacctacga cgctctgatc actggcctgg ccgacgggcc atggcagggg 180
tcctccgcgg cgtccatggt ggctgccgcc acgccccagg tggcgtggtt gaggagcacc 240
gccgggcagg ccgagcaagc cggcagccaa gcggtggcag cggcgagtgc ttatgaggcg 300
gcgtttttcg cgaccgtgcc gcccccggag atcgcggcca acagggcgtt gttgatggcg 360
ttgctggcga cgaacttcct tggccagaac acggcggcga tcgcggccac cgaggcgcaa 420
tacgccgaga tgtgggccca ggatgcggcc gcgatgtacg gctatgctgg cgcgtcggcg 480
gcggcgacgc agttgtcgcc attcaatccg gcggcgcaga ccatcaaccc ggccgggctg 540
gccagccagg ccgcatctgt cggacaagct gtcagcgggg ccgcaaatgc gcaagcactc 600
accgacattc ctaaagcgtt gtttgggctt agcggaatct tcaccaatga accgccttgg 660
ctcaccgacc ttggcaaggc gctcggtttg accgggcaca cctggtcctc ggacggtagc 720
gggctcatcg tgggcggagt gcttggcgac tttgtgcagg gtgtgaccgg gtcggccgaa 780

-continued

```
cttgatgcca gcgtggccat ggacacgttc ggcaaatggg tctcgcccgc tcggctcatg     840

gtcacccaat tcaaggacta ctttggcctg gcgcacgacc tgccgaagtg ggcgagtgaa     900

ggcgccaaag ccgccggtga ggccgccaag gcgttgccgg ccgccgttcc ggccattccg     960

agtgctggcc tgagcggcgt tgcgggcgcc gtcggtcagg cggcgtcggt cgggggattg    1020

aaggttccgg ccgtttggac cgccacgacc ccggcggcga gccccgcggt gctggcggcg    1080

tccaacggcc tcggagccgc ggccgccgct gaaggttcga cacacgcgtt tggcgggatg    1140

ccgctcatgg gtagcggtgc cggacgtgcg tttaacaact tcgctgcccc tcgatacgga    1200

ttcaagccga ccgtgatcgc ccaaccgccg gctggcgga                           1239
```

<210> SEQ ID NO 69
<211> LENGTH: 294
<212> TYPE: DNA
<213> ORGANISM: Mycobacteria tuburculosis

<400> SEQUENCE: 69

```
atgacctcgc gttttatgac ggatccgcac gcgatgcggg acatggcggg ccgttttgag      60

gtgcacgccc agacggtgga ggacgaggct cgccggatgt gggcgtccgc gcaaaacatt     120

tccggcgcgg gctggagtgg catggccgag gcgacctcgc tagacaccat gacccagatg     180

aatcaggcgt ttcgcaacat cgtgaacatg ctgcacgggg tgcgtgacgg gctggttcgc     240

gacgccaaca actacgaaca gcaagagcag gcctcccagc agatcctcag cagc           294
```

<210> SEQ ID NO 70
<211> LENGTH: 282
<212> TYPE: DNA
<213> ORGANISM: Mycobacteria tuburculosis

<400> SEQUENCE: 70

```
atgaccatca actatcaatt cggggacgtc gacgctcacg gcgccatgat ccgcgctcag      60

gccgggtcgc tggaggccga gcatcaggcc atcatttctg atgtgttgac cgcgagtgac     120

ttttggggcg gcgccggttc ggcggcctgc caggggttca ttacccagct gggccgtaac     180

ttccaggtga tctacgagca ggccaacgcc cacgggcaga aggtgcaggc tgccggcaac     240

aacatggcac aaaccgacag cgccgtcggc tccagctggg cc                        282
```

<210> SEQ ID NO 71
<211> LENGTH: 1185
<212> TYPE: DNA
<213> ORGANISM: Mycobacteria tuburculosis

<400> SEQUENCE: 71

```
atgaaggcac cgttgcgttt tggcgttttc atcacgccat tccatccgac cggtcaatcc      60

ccgaccgtgg cgttgcaata cgacatggag cgcgtcgttg cgctggaccg gctcggctac     120

gacgaggcgt ggtttggcga acaccactcc ggtggctacg agctgatcgc ttgcccggag     180

gtgtttatcg cggccgcagc ggaacggacc acccacatcc ggctaggtac cggagtggtt     240

tcgctgccct accatcatcc gctaatggtg gccgaccgtt gggtgctgct ggatcacctg     300

acccgtgggc gggtcatgtt cggcaccggc cccggcgcgc tgccgtcgga cgcctacatg     360

atgggcatcg atccggtcga gcagcgacga atgatgcagg agtccctcga ggcgattctc     420

gcgctgttcc gtgccgcacc tgacgagcga atcgaccgcc actccgactg gttcaccctg     480

cgtgaagcgc aattgcacat ccgcccctac acctggccgt accccgaaat cgctaccgca     540

gccatgattt cgccatcggg tccgcgactg gccggtgcgc tgggcacgtc gctgttatca     600
```

```
ctgtcgatgt cagtgcccgg cggctacgct gcgctggaaa cagcgtgggg cgtggtgcgg    660

gagcaggccg ccaaagctgg gcggggcgag ccggatcgcg ccgattggcg ggtgttgagc    720

atcatgcact tgtcggacag ccgcgaccag gcgatcgacg actgcactta cgggttaccc    780

gacttctcga ggtacttcgg cgcggcaggg tttgtcccgt tggcgaacac cgtggaaggc    840

acccagtcgt ctcgggaatt cgtcgagcaa tacgcggcca agggaaattg ctgcatcggc    900

acgcccgatg acgcgatcgc ccacattgaa gacttgctgc accggtcggg tggcttcgga    960

acgttgctac tgctcggcca cgactgggcc ccgccaccgg caacctttca ctcctatgag   1020

ctgttcgccc gtgctgtgat tccttatttc aagggacaac tcgcggcgcc gcgggcgtcg   1080

cacgaatggg ctagaggcaa gcgcgaccaa ttgattggcc gcgccggcga agcggtcgtc   1140

aaagccatca ccgagcacgt cgccgaacaa ggggaagcgg gcagc                   1185
```

<210> SEQ ID NO 72
<211> LENGTH: 966
<212> TYPE: DNA
<213> ORGANISM: M. tuberculosis

<400> SEQUENCE: 72

```
atgggcgcac ctaccgaacg gttagttgat accaacggcg tgcgactgcg agtggtcgag     60

gccggtgagc ccggcgcacc cgtggtgata ctggcccacg gctttcccga actggcctat    120

tcatggagac accagattcc tgcgcttgcc gacgccggct accacgtgtt ggctcccgat    180

cagcgcggtt acggcggatc gtctcgccca gaggcgatcg aggcctacga cattcaccgg    240

ttgaccgctg acctagtggg cctactagat gatgtcggtg ccgagcgggc ggtctgggtt    300

ggtcatgact ggggtgccgt ggtggtgtgg aacgcgccac tgctgcacgc tgaccgagtc    360

gccgccgttg ccgcgttgag cgtccccgcg ctgccccggg cacaggtgcc gccgacgcaa    420

gcgttccgca gcaggtttgg ggagaacttc ttctacatcc tttatttcca ggagcccggc    480

atcgccgacg ccgaactcaa tggcgacccg gcccgcacga tgcgccgaat gatcggcggt    540

ctgcgccctc cgggcgatca gagcgcggca atgcgtatgc tggcgcccgg ccccgacggc    600

tttatcgatc ggcttccgga gccggccggg ttgccggcct ggattagtca ggaggaactc    660

gaccactaca tcggcgagtt cacccgcacc ggtttcaccg gcggcctgaa ctggtaccgc    720

aacttcgacc gcaactggga gaccacggcc gacctcgccg gcaagacgat ctccgtgccc    780

tcgttgttca ttgcgggcac agccgatccc gtcttgacgt tcacccgcac cgaccgcgct    840

gcggaggtga tctccggccc gtatcgcgag gtgctgatcg acggggccgg tcactggctg    900

cagcaggaac gtcccggtga ggtgaccgcg gccctgctgg agttcctgac ggggttggag    960

ttgcga                                                               966
```

<210> SEQ ID NO 73
<211> LENGTH: 1365
<212> TYPE: DNA
<213> ORGANISM: Mycobacteria tuburculosis

<400> SEQUENCE: 73

```
gtgaataccg atgtgctggc tggcctgatg gccgagctgc ccgaggggat ggtggtcacc     60

gaccccgccg tcaccgacgg ctaccggcaa gaccgggcct ttgacccttc ggccggcaaa    120

ccgctggcaa tcatccggcc acggcgcacc gaagaggtgc agacggtgct gcgttgggcc    180

agtgcgaacc aggtgcccgt ggtgacccga ggagccggta gcggcctttc gggcggggcg    240
```

-continued

```
accgccctgg atggcgggat cgtgctgtcc accgaaaaga tgcgcgacat caccgtcgac    300

ccggtcaccc gcaccgcagt gtgccagccc ggcctgtaca acgccgaggt gaaggaggcc    360

gccgccgaac acggcctgtg gtatcccccg gatccgtcgt cgttcgagat ctgcagcatc    420

ggcggcaaca tcgccaccaa cgccggcggg ctgtgctgcg tgaagtacgg cgtcacaggc    480

gactacgtac tgggcatgca ggttgtgctg gccaacggca ccgcggtccg gctgggcggc    540

ccacggctca aggacgtcgc cgggctttcc ctgaccaaac tgttcgtcgg cagcgaaggc    600

acgctgggcg tcatcacgga ggtgacgttg cgactgctgc ccgcacagaa tgcatcgagc    660

atcgtggtgg ccagcttcgg ctcggtgcag gcggcggtcg atgcggtgct cggggttacc    720

ggccgacttc gccccgcgat gctggagttc atggattcgg tggcgatcaa cgccgtcgag    780

gacaccttgc ggatggacct ggaccgcgat gcggcggcca tgctggtggc tggttctgat    840

gaacgtggcc gcgcggccac cgaagacgcc gccgtgatgg ccgccgtgtt cgccgaaaac    900

ggtgcgatag acgtgttttc gaccgacgac ccggatgagg gcgaggcgtt cattgcggcc    960

cggcggttcg ccattccggc ggtcgagagc aagggggcgt tgctgctcga ggacgtcggg   1020

gtaccgctgc ccgcactggg cgaactggtc accgggattg cgcgcatcgc cgaggagcgg   1080

aatctgatga tctcggtgat cgcccacgcc ggggacggca atacccaccc gttgctggtg   1140

tacgaccccg cagatgccgc gatgctagag cgcgcccacc tcgcgtacgg cgaaatcatg   1200

gacctggccg tcggcctggg cggcacgatc accggcgaac acggcgtggg ccggttgaaa   1260

cggccgtggt tggccggcta tctcgggccc gacgtcctgg ccctcaacca gcgcatcaag   1320

caagcgctgg acccccaggg catcctcaat cccggctcgg cgatc                   1365
```

<210> SEQ ID NO 74
<211> LENGTH: 1215
<212> TYPE: DNA
<213> ORGANISM: Mycobacteria tuburculosis

<400> SEQUENCE: 74

```
atgacatcag taatgtctca cgaattccag ctcgccaccg ccgaaacctg gccgaatccg     60

tggccgatgt accgcgcgtt gcgcgaccac gacccggtgc accacgtcgt cccgccgcag    120

cgtcccgagt acgactacta cgtgctgtcc cggcacgccg acgtctggtc ggcagcgcgg    180

gaccatcaga cgttctcgtc ggcgcaaggc ttgaccgtta actacggcga gctggaaatg    240

attggactgc acgacacccc gcccatggtg atgcaggatc cgccggtcca caccgagttt    300

cgcaagctgg tgtcgcgcgg cttcacgcca cgacaggtcg aaaccgtcga gcccacggtg    360

cgcaagttcg tcgttgagcg gctcgaaaag ctgcgcgcca acggtggcgg cgacattgtc    420

accgaactat tcaaaccgct cccgtcgatg gtggtggcgc actatctcgg tgttcccgaa    480

gaggattgga cgcaattcga cgggtggacc caggccatcg tggcggcgaa cgcggttgac    540

ggcgccacca ccggcgcact ggacgcggtc ggctcgatga tggcctactt caccgggctg    600

atcgagcgac gccgcaccga gcccgccgac gacgccatct cccacctggt agccgccggg    660

gtcggcgccg acggcgacac cgccggcaca ctgtccatac tggcgttcac gttcaccatg    720

gtcaccggcg gcaacgacac cgtcaccggc atgctaggcg gttcgatgcc gttgctgcac    780

cggcggcccg accagcgccg gctgctgctg gatgacccag agggcatccc cgacgcggtc    840

gaggagctgc tgcggctcac ctcgccggtg caggggctgg cgcgcacaac cacgcgcgac    900

gtcacgatcg gtgacaccac catcccggcc ggtcgccggg tgctgctgct gtacggctcg    960

gccaaccgtg acgaacgcca atacggcccg gacgcagccg aactcgatgt cactcggtgc   1020
```

-continued ccgcgcaaca tcttgacctt cagccacggc gcccaccact gcctgggtgc ggccgcggcc 1080
cggatgcaat gccgggtggc gctgaccgaa ctgctggccc ggtgcccgga cttcgaggtg 1140
gccgagtcac gcatcgtgtg gtccggcggc agttatgtcc ggcgtccgct gtcggtgccg 1200
ttccgagtga catcc 1215

<210> SEQ ID NO 75
<211> LENGTH: 606
<212> TYPE: DNA
<213> ORGANISM: Mycobacteria tuburculosis

<400> SEQUENCE: 75
atggcgggta ccgactggct gtccgcgcgt cggaccgagt tagccgcaga tcggatactc 60
gacgccgccg agcgactctt tacgcagcgt gacccggcgt cgatcggcat gaacgagatc 120
gccaaggccg caggctgttc gcgcgcaaca ctgtatcggt acttcgacag ccgcgaggcg 180
ctgcgaaccg cgtacgtgca ccgcgagacc cgccggctcg gccgcgagat catggtgaag 240
atcgccgatg tcgtcgaacc tgccgaacgg ctgctggtga gcatcaccac gacgttgcgg 300
atggtccgcg acaaccccgc gttggccgcg tggtttacca ccacccgccc accgatcggc 360
ggcgagatgg ccggacggtc cgaggtgatc gcggccctgg ccgcggcatt cctcaactca 420
ctaggtcccg acgatccgac caccgtcgaa cgccgcgccc gctgggtggt ccggatgctc 480
acatcgctgc tgatgttccc cggccgtgac gaagccgacg aacgagcgat gatcgcggag 540
ttcgtcgtcc cgatcgtgac acctgcttct gccgccgcta ggaaggccgg tcaccctgga 600
cccgag 606

<210> SEQ ID NO 76
<211> LENGTH: 534
<212> TYPE: DNA
<213> ORGANISM: Mycobacteria tuburculosis

<400> SEQUENCE: 76
atgcatccaa tgataccagc ggagtatatc tccaacataa tatatgaagg tccgggtgct 60
gactcattgt ctgccgccgc cgagcaattg cgactaatgt ataactcagc taacatgacg 120
gctaagtcgc tcaccgacag gctcggcgag ctgcaggaga actggaaagg tagttcgtcg 180
gacttgatgg ccgacgcggc tgggcggtat ctcgactggc tgactaaaca ctctcgtcaa 240
attctggaaa ccgcctacgt gatcgacttc ctcgcatacg tctatgagga gacacgtcac 300
aaggtggtac ccccggcgac tatcgccaac aaccgcgagg aggtgcacag gctgatcgcg 360
agcaacgtgg ccggggtaaa cactccagca atcgcaggac tcgatgcaca atatcagcag 420
taccgggccc aaaatatcgc tgtcatgaac gactatcaaa gtaccgcccg gtttatccta 480
gcgtatctgc cccgatggca ggagccgccg cagatctacg gggcggggg cggg 534

<210> SEQ ID NO 77
<211> LENGTH: 1230
<212> TYPE: DNA
<213> ORGANISM: Mycobacteria tuburculosis

<400> SEQUENCE: 77
gtggccacga tagcccaacg gctgcgtgac gaccacgggg tggcggcgtc ggagtcgtcg 60
gtgaggcgtt ggatcgcaac gcatttcgcc gaggaggtgg cccgcgagag agtcacggtg 120
ccgcgcggac cggtcgatgc gggtagtgag gcgcagatcg attacgggcg gctgggcatg 180

-continued

```
tggttcgacc cggccaccgc gcgccgggtc gcggtgtggg cgttcgtgat ggtgctggcg    240

ttctcccgac acctgttcgt gcgtccggtc atccggatgg accaaaccgc ttggtgtgct    300

tgccatgtcg ccgcattcga attcttcgac ggggtgccgg cgcggctagt gtgtgacaac    360

ctcaggaccg gggtggacaa gcccgacctg tacgacccgc agatcaaccg ctcctacgcc    420

gagctggcca gccactacgc cacgctggtc gacccggccc gcgccagaaa acccaaagat    480

aaaccccgcg tggagcggcc gatgacctat gtgcgggact cgttttggaa aggccgcgag    540

ttcgattcgc tggcccagat gcagcaggcg gcggtcacct ggagcaccga agtggccggg    600

cttcggtact tacgtgcctt ggagggcgcc caacccctgc ggatgttcga agctgtggag    660

caacaagcgt tgatcgcatt gccgcccagg gcatttgaac tcaccagctg gtcgatcggc    720

accgtcgggg tggacacgca cctcaaagtt ggcaaggcac tctattccgt gccgtggcgg    780

ctgatcgggc aacgcctgca cgcgcgcacc gccggtgatg tggtgcagat cttcgccggc    840

aacgatgtgg tggccaccca tgtgcgccga cccagcgggc gctccaccga cttctcccac    900

tacccaccgg agaagatcgc cttccacatg cgcaccccga cctggtgtcg acacaccgcc    960

gaactggtcg gcccagccag ccagcaagtg atcgccgaat tcatgcgcga caacgccatc   1020

caccacctac ggtcggccca aggcgtgctc gggctacgcg acaaacacgg ctgcgaccgg   1080

ctggaggccg cctgcgcccg cgccatcgag gtcggcgacc cgagctatcg caccatcaag   1140

ggcatccttg ttgccggcac cgaacacgcc gccaacgagc cgaccaccag tagtccggca   1200

agcaccgctg gggcgttcc tgcgcggccc                                     1230
```

<210> SEQ ID NO 78
<211> LENGTH: 753
<212> TYPE: DNA
<213> ORGANISM: Mycobacteria tuberulosis

<400> SEQUENCE: 78

```
atgtctatct gtgatccggc gctgcgtaat gcgctacgta ccctgaaact gtccggcatg     60

ctcgacaccc tcgacgcccg cctggcccaa acccgcaacg gcgacctggg gcatctggaa    120

ttcctgcaag cgttgcgtga agacgagatc gcccgccgcg agtccgccgc cctgacacga    180

cgattacgcc gcgccaagtt cgaagcccaa gccaccttcg aagacttcga cttcactgcc    240

aacccgaaac tgcccggtgc gatgttgcgc gatctggccg cgctgcgctg gctggatgcc    300

ggcgaatcgg tcatcctcca cggcccggtc ggcgtcggaa aaacccatgt agcacaagca    360

cttgtccacg ccgtggcccg ccgcggcggc gacgtgcgct tcgccaaaac ctcccgcatg    420

ctctccgacc tcgccggcgg gcacgccgac cgatcctggg gccaacgcat ccgcgaatac    480

accaagccgc tcgtgctcat tctggacgac ttcgcgatgc gtgagcacac cgccatgcac    540

gctgatgacc tctacgagct catcagcgac cgcgccatca ctggcaaacc gctgatcttg    600

accagcaacc gcgcaccgaa taactggtac ggcctgttcc ccaaccccgt cgtcgccgaa    660

tcactcctgg atcggctcat caacaccagc caccaaatcc tcatggacgg acccagctac    720

cgaccccgca agagacccgg ccgcaccacc agc                                 753
```

<210> SEQ ID NO 79
<211> LENGTH: 696
<212> TYPE: DNA
<213> ORGANISM: Mycobacteria tuberulosis

<400> SEQUENCE: 79

```
atgcatctaa tgatacccgc ggagtatatc tccaacgtaa tatatgaagg tccgcgtgct     60
```

-continued

```
gactcattgt atgccgccga ccagcgattg cgacaattag ctgactcagt tagaacgact    120

gccgagtcgc tcaacaccac gctcgacgag ctgcacgaga actggaaagg tagttcatcg    180

gaatggatgg ccgacgcggc tttgcggtat ctcgactggc tgtctaaaca ctcccgtcag    240

attttgcgaa ccgcccgcgt gatcgaatcc ctcgtaatgg cctatgagga gacacttctg    300

agggtggtac cccggcgac tatcgccaac aaccgcgagg aggtgcgcag gctgatcgcg     360

agcaacgtgg ccgggggtaa acactccagc aatcgcagac ctcgaggcac aatacgagca    420

gtaccgggcc gaaaatatcc aagcaatgga ccgctatcta agttggaccc gatttgcgct    480

atcgaagctg ccccgatggc gggagccgcc gcagatccac aggagcgggt aggtccaaga    540

ggccggcgcg gtcttgcagg ccagcaacaa tgccgcggtc gaccaggccc atcgcttcgc    600

tgctcgcacg acacaccgcg gtttcagatg aatcaggcgt ttcacaccat ggtgaacatg    660

ttgctgacgt gttttgcatg tcaggagaaa ccgaga                              696
```

<210> SEQ ID NO 80
<211> LENGTH: 528
<212> TYPE: DNA
<213> ORGANISM: Mycobacteria tuberulosis

<400> SEQUENCE: 80

```
atgcatccaa tgataccagc ggagtatatc tccaacataa tatatgaagg cccgggcgct     60

gactcattgt tttcgcctc cgggcaattg cgagaattgg cttactcagt tgaaacgacg     120

gctgagtcgc tcgaggacga gctcgacgag ctggatgaga actggaaagg tagttcgtcg    180

gacttgttgg ccgacgcggt tgagcggtat ctccaatggc tgtctaaaca ctccagtcag    240

cttaagcatg ccgcctgggt gatcaacggc ctcgcgaacg cctataacga cacacgtcgg    300

aaggtggtac cccggagga gatcgccgcc aaccgcgagg agaggcgcag gctgatcgcg     360

agcaacgtgg ccggggtaaa cactccagca atcgcagacc tcgatgcaca atacgaccag    420

taccgggccc gcaatgtcgc tgtaatgaac gcctatgtaa gttggacccg atctgcgcta    480

tcggatctgc cccggtggcg ggaaccgccg cagatctaca ggggcggg                 528
```

<210> SEQ ID NO 81
<211> LENGTH: 1170
<212> TYPE: DNA
<213> ORGANISM: M. tuberculosis

<400> SEQUENCE: 81

```
atgatcatcg ttgtcgggat cggcgccgac ggcatgaccg gtctctccga gcattctcgc     60

tccgaattgc gcagggccac agtaatttac ggctcgaaac ggcaacttgc cctgctcgac    120

gataccgtca ccgccgagcg ctgggagtgg ccgacgccga tgctgcccgc ggtgcaaggc    180

ctgtcaccgg atggggctga cctacacgtg gttgccagcg gcgacccgtt gttgcatggt    240

atcggctcca ccctgatccg gctgttcggc cacgacaacg tgaccgtgtt gccgcacgtg    300

tccgcggtga cgttggcgtg cgcccggatg ggctggaacg tgtatgacac cgaggtgatc    360

agcctggtca ccgcgcaacc acacaccgcg gtgcgccgcg gcggccgggc catcgtgctg    420

tccggcgatc ggtccacccc gcaggcgctg gcggtgctgc tgaccgagca cggtcgcggt    480

gactccaagt tcagcgtgct cgaacagctt ggcggcccgg ccgaacgccg ccgcgacggt    540

acggcccggg catgggcctg cgacccaccc ctcgatgtcg atgagctcaa cgtgatcgcc    600

gtgcgctacc tgctcgacga gcgcacgtcg tgggcacccg acgaggcatt cgcgcacgac    660
```

-continued

```
gggcagatca ccaaacaccc gatccgcgtg ctgaccctgg ctgcgctggc gccaaggccc    720

gggcagcggt tatgggacgt cggcgcgggc tcaggcgcca tcgcggtcca gtggtgtcgg    780

agctggccgg gctgcaccgc ggtggcgttc gagcgcgacg aacggcgccg ccgcaacatt    840

gggttcaatg ccgcggcctt cggggtgagc gtcgacgtgc gcggcgacgc gcccgatgcg    900

ttcgacgacg ccgcacggcc gtcggtgatt tttcttggcg gtggtgtaac ccagccaggc    960

ctgcttgagg cctgcctgga cagcctgccc gcaggcggga acttggtcgc caacgctgtc   1020

accgtcgaat cggaagccgc tctggcgcat gcatattcgc gcctcggtgg cgagctacga   1080

cgattccagc actatctcgg cgaaccgctg ggcggcttca ccggttggcg cccacagctg   1140

ccggtcaccc agtggtcggt gaccaagcga                                    1170
```

<210> SEQ ID NO 82
<211> LENGTH: 747
<212> TYPE: DNA
<213> ORGANISM: Mycobacteria tuberulosis

<400> SEQUENCE: 82

```
gtggacgaca cgggcgctgc tccggtagta attttcggcg gccgcagcca gatcggcggc     60

gaactcgcgc gacgcctggc tgccggggcg acgatggtgc tggccgcgcg gaacgccgat    120

caactcgccg accaggccgc cgcactccgc gcagctggcg ctatagcggt gcacacccgg    180

gagttcgacg ccgacgacct ggccgcacac ggcccgttgg tcgcttcgct cgttgccgag    240

cacggcccca tcggcaccgc ggtgctggcc ttcgggatac tcggcgacca ggcccgcgcc    300

gagacagacg cggcgcacgc ggtggccatc gtgcacaccg actacgtcgc ccaggtcagc    360

ctgctgactc atctggcagc ggcgatgcgc accgccggac ggggatcgct ggtggtgttc    420

tcctcggtcg ccgggattcg ggtgcgccgc gccaactatg tctacggatc ggccaaagcc    480

ggcctggacg gcttcgccag cggcctggcc gatgcgttgc acggcaccgg ggtgcggtta    540

ctgatcgcgc ggccgggatt cgtcatcggg cgcatgaccg agggcatgac gcccgcaccc    600

ctgtcggtca ccccggagcg ggtggccgcc gcgaccgcgc gtgcgctggt caacggtaag    660

cgcgtggtgt ggattccgtg ggcgctgcgg ccaatgtttg ttgcgctgcg gttgcttccc    720

cggttcgtct ggcgcaggat gccgcga                                        747
```

<210> SEQ ID NO 83
<211> LENGTH: 411
<212> TYPE: DNA
<213> ORGANISM: Mycobacteria tuberulosis

<400> SEQUENCE: 83

```
gtggcgatgg tcaacaccac tacgcggctt agtgacgacg cgctggcgtt tctttccgaa     60

cgccatctgg ccatgctgac cacgctgcgg gcggacaact cgccgcacgt ggtggcggta    120

ggtttcacct tcgaccccaa gactcacatc gcgcgggtca tcaccaccgg cggctcccaa    180

aaggccgtca atgccgaccg cagtgggctt gccgtgctca gccaggtcga cggcgcgcgc    240

tggctctcac tggagggtag ggcggcggtg aacagcgaca tcgacgccgt gcgcgacgcc    300

gagctgcgct acgcgcagcg ctatcgcacc ccgcgtccca atccacgccg agtggtcatc    360

gaggtccaga ttgagcgcgt gctgggatcc gcggatctgc tcgaccgggc c             411
```

<210> SEQ ID NO 84
<211> LENGTH: 1461
<212> TYPE: DNA
<213> ORGANISM: Mycobacteria tuberulosis

<400> SEQUENCE: 84

```
atgccccgcg cccgatggct gcagagcgcg gccctcatgg gcgccttggc cgtggtgttg      60
ataaccgcgg caccggtggc cgccgatgcc taccaggtgc ccgctccgcc ctcgcccacc     120
gcatcctgtg acgtaataag cccggttgcg atcccctgcg tggcgctcgg caagttcgcc     180
gacgcggtcg ctgcggagtg tcgccgcgtc ggtgtgcccg atgcgcggtg cgtgcttccg     240
ctcgcgcacc gggtgaccca ggccgcgcgt gatgcctacc tacagtcttg ggtgcatcgc     300
accgcgcggt tccaggatgc gttgcaagac ccggtgccgc tgcgggaaac tcagtggctc     360
ggcacgcaca actcgttcaa cagcctcagc gattcgttca cggtctcgca cgcagactca     420
aaccagcagc tgtcgttggc ccaacagctc gacatcgacg tccgcgcgct cgagctagac     480
ctgcactact tgccccgcct cgagggccac ggcgccccg gcgtcaccgt gtgtcacggg      540
ctgggaccga agaacgcgaa cctaggctgc accgtcgaac ctctgctggc cacagtgctg     600
ccgcagatcg ccaactggtt gaacgcaccc gggcataccg aggaggtcat cctgctctac     660
ctggaggacc agctgaagaa cgcgtcggcg tatgagtcgg tggtggctac cctcgaccaa     720
gtgttgcggc gtgcggacgg aacaagcctt atctaccgtc ccaacccggc ccggcgtgcc     780
accaacggct gtgtcccgct tccactcgac gtgtcgcggg aggaaatccg cgcatccggc     840
gcacgagccg tgctcgtcgg gtcttgtgcg ccaggttggt cggccgccgt cttcgactgg     900
agcggcgttg agctggaaag cggctcgaac tccggctacc ggccataccc ggcctgcgat     960
gccacctatg gccgcggtgt ctacgcttgg cgactggtcc gctattacga ggactccacg    1020
ctggccacgg cgttggccaa cccgacccgt ccaccggcca atccgcaggc gcttaccccg    1080
ccgaaggtgc cggcgatgac cgattgcggg gtcaatctgt tcggcttcga tcagctgctc    1140
cccgaagacg gccgcattca ggcgtcgttg tggagctggg caccggacga accgcgtgcc    1200
ggtgccggag catgcgccct gcagggcgcg gatggccgct gggtcgccgc atcgtgcggt    1260
gacccacacc ctgcggcctg tcgggacgcg gcaggcaggt ggaccgtgac gccggcaccc    1320
gtggtcttcg ccggggctgc cctagcctgc acagccatcg gcgcggactt taccctgccc    1380
cgaacgggca atcagaacgc ccgtctgcac gccgtggccg ggcccgccgg tggcgcctgg    1440
gtgcattacc tactgccgcc a                                              1461
```

<210> SEQ ID NO 85
<211> LENGTH: 429
<212> TYPE: DNA
<213> ORGANISM: Mycobacteria tuberulosis

<400> SEQUENCE: 85

```
atgaccacca cgccccgaca acccctgttc tgcgcccacg ccgacaccaa cggcgacccg      60
ggccgctgcg cctgcggcca gcagctcgcc gacgtcggcc cggccacccc gccaccgccc     120
tggtgcgaac cgggcaccga acccatctgg gagcagctca ccgaacgata cggcggcgtc     180
acaatctgcc agtggacacg atattttccg gccggcgacc cggtggctgc cgacgtgtgg     240
atcgccgccg acgatcgtgt cgttgacggc cgggtgctgc gcacccaacc ggcgattcac     300
tacacggaac cgcccgtgtt ggggatcggc ccggcggcgg cccgccggct ggccgctgag     360
ctgctcaacg ccgccgacac cctcgacgac ggccgccggc agctagacga cctcggcgaa     420
caccggcgg                                                            429
```

<210> SEQ ID NO 86

<211> LENGTH: 996
<212> TYPE: DNA
<213> ORGANISM: Mycobacteria tuberulosis

<400> SEQUENCE: 86

```
gtgaacaccg cgacccgggt ccggctggcc cgcaaacgcg ccgaccggct caatctgaaa     60
ctaatcaaga acggccacca cttcaggttg cgtgacgccg acgagatcac gctggcggtc    120
gggcacctag gggtggtgga agccttcctg gcggcggcca agtcgcaaaa caagccgccc    180
ggtccgccgc cgagcctcca cgccccgcca tcctggcggc gcgacatcga cgactacctg    240
ctcaacctga acgccgccgg tcaacgccca gcgacgatcc ggctacgcaa gacggtgctg    300
tgcgcagccg cccacggcct cggccgccca cccgccgacg tcaccgccga acacctcctg    360
gactggctag gcaaacagca gcacctctcc ccagagggcc gcaaaaccta tcgcagcacg    420
ttgcggggct tcttcgtgtg ggcctacgaa atggaccggg tgcgcgacta tgtcgcagac    480
tccctgccta aggtgcgctg cccgaaacag ccgccccgcc cggccggcga cgacgtctgg    540
caagcggcgc tggccaaggc cgaccgtcga atcgagctga tgatccgcct agccggtgag    600
gccgggctgc gacgcgccga agccgcccag gcgcacaccg gcgacttgat ggacggcggg    660
cttctcctcg ttcacggcaa aggtggtaaa cgccgtattg tgccgatcag cgactacttg    720
gccgcgctca tccgcgacac cccgcacggc tacctgttcc ccaacggcac cggcggccac    780
ctcaccgccg aacacgtggg aaaactcgtc tcccgggcat tacccggtga cgcgaccatg    840
cacaccctgc ggcaccgata cgccacccgc gcctaccgcg gctcccacaa cttgcgagct    900
gtacaacaac ttctcggtca cgcctcgatc gtgacaacag aacgctacac agcgctgtgc    960
gacgacgagg tgcgcgccgc agcagcagcc gcatgg                              996
```

<210> SEQ ID NO 87
<211> LENGTH: 366
<212> TYPE: DNA
<213> ORGANISM: Mycobacteria tuberulosis

<400> SEQUENCE: 87

```
gtgcacgtgt gccacacgat cgccgacgtg gtcgaccggg ccaaagccga acgctccgaa     60
aacacgcttc gcaaggattt caccccctcg gagctgctcg ccgctggtcg ccggatcgcc    120
gagctggaac ggccgaaagc caaacagcgg caacgcgaag gcggcgacca tggccgccag    180
gctcgatatt ctggcttagg ctccatggag cctaagccag aatcagagcg cgatgcccac    240
aaagccgaca ctgccatcag cgaagccctc ggcatctccc gcggccacta ccagcggctc    300
aaacgaatcg acaacgcaac ccgcagcgaa gctggctacc gggatggttt aaacggttgg    360
agcggc                                                               366
```

<210> SEQ ID NO 88
<211> LENGTH: 324
<212> TYPE: DNA
<213> ORGANISM: Mycobacteria tuberulosis

<400> SEQUENCE: 88

```
atgtcaggtg gttcatcgag gaggtacccg ccggagctgc gtgagcgggc ggtgcggatg     60
gtcgcagaga tccgcggtca gcacgattcg gagtgggcag cgatcagtga ggtcgcccgt    120
ctacttggtg ttggctgcgc ggagacggtg cgtaagtggg tgcgccaggc gcaggtcgat    180
gccggcgcac ggcccgggac cacgaccgaa gaatccgctg agctgaagcg cttgcggcgg    240
gacaacgccg aattgcgaag ggcgaacgcg attttaaaga ccgcgtcggc tttcttcgcg    300
```

gccgagctcg accggccagc acgc 324

<210> SEQ ID NO 89
<211> LENGTH: 984
<212> TYPE: DNA
<213> ORGANISM: Mycobacteria tuberulosis

<400> SEQUENCE: 89
aaagaccgcg tcggctttct tcgcggccga gctcgaccgg ccagcacgct aattacccgg 60
ttcatcgccg atcatcaggg ccaccgcgag ggccccgatg gtttgcggtg gggtgtcgag 120
tcgatctgca cacagctgac cgagctgggt gtgccgatcg ccccatcgac ctactacgac 180
cacatcaacc gggagcccag ccgccgcgag ctgcgcgatg gcgaactcaa ggagcacatc 240
agccgcgtcc acgccgccaa ctacggtgtt tacggtgccc gcaaagtgtg gctaaccctg 300
aaccgtgagg gcatcgaggt ggccagatgc accgtcgaac ggctgatgac caaactcggc 360
ctgtccggga ccacccgcgg caaagcccgc aggaccacga tcgctgatcc ggccacagcc 420
cgtcccgccg atctcgtcca gcgccgcttc ggaccaccag cacctaaccg gctgtgggta 480
gcagacctca cctatgtgtc gacctgggca gggttcgcct acgtggcctt tgtcaccgac 540
gcctacgctc gcaggatcct gggctggcgg gtcgcttcca cgatggccac ctccatggtc 600
ctcgacgcga tcgagcaagc catctggacc cgccaacaag aaggcgtact cgacctgaaa 660
gacgttatcc accatacgga taggggatct cagtacacat cgatccggtt cagcgagcgg 720
ctcgccgagg caggcatcca accgtcggtc ggagcggtcg gaagctccta tgacaatgca 780
ctagccgaga cgatcaacgg cctatacaag accgagctga tcaaacccgg caagccctgg 840
cggtccatcg aggatgtcga gttggccacc gcgcgctggg tcgactggtt caaccatcgc 900
cgcctctacc agtactgcgg cgacgtcccg ccggtcgaac tcgaggctgc ctactacgct 960
caacgccaga gaccagccgc cggc 984

<210> SEQ ID NO 90
<211> LENGTH: 1437
<212> TYPE: DNA
<213> ORGANISM: Mycobacteria tuberulosis

<400> SEQUENCE: 90
atgactaatg aacaacattt cgctgacgat ggcgacatca aacagctcag cctcgacgaa 60
acccgttccg cggcaaaaca gctcctcgac tccgtcgagg gcgacctgac cggtgatgtg 120
gcgcaacgtt ttcaggcgct gacacgccac gccgaggaac tgcgggcgga gcagcgccgc 180
cgcggccgcg aagccgagga ggcgctgcgc cgctgccggg ccggtgagct gagggtggtg 240
cccggtgctc ccaccggcgg cgacgacggc gacgcgccgc cgggcaactc gttgcgcgac 300
atcgcgtttc gcacactgga cgtttgtgtg cgcgatggcc tgatgtcgtc gcgggcggcg 360
gaagccgcgg aaaccttgtg ccgcaccggg ccgccgcagt cgacgtcgtg ggcgcagcgc 420
tggctggcgg ccaccggcaa ccgcgactac ctgggggcgt tcgtcaagag ggtttcgaac 480
cctgttgcgg ggcacacgac ctggaccgac cgggaagcgg ccgcgtggcg tgaggcggcc 540
gcggtggccg ccgagcagcg agcaatgggc ttggtggaca ccgccggcgg gtttttgatc 600
ccggcggcgc tggatccggc gattctgctg tcgggtgatg gttcaacgaa tccgatccgg 660
caggtggcga gggtggtgca aacgacctcc gaggtttggc ggggcgtgac ctccgaaggc 720
gccgaggctc attggtactc cgaagcccag gaggtgtccg acgattcgcc aacgctggcc 780

-continued

```
cagccggcgg tgccgagcta ccgtggctcc tgctggattc cgttcagtct cgagattgag    840

ggtgacgccg ccggattcgt cgcagaggtg ggccgcgtcc tagcggattc ggttgagcag    900

ctgcaggcgg cggcgttcgt cagcggctcc ggcaacggcg agcccaccgg attcgtctcc    960

gcactgaccg gcaccgcgga ctacaccgtc accggcgcgg ggacggaagc cgttgtagcc   1020

gccgacgttt acgcgctgca gtcggcgttg ccgccgcgct ttcaatccaa cagcgcgttc   1080

gcggcgaact tgtccaccat caacgtgctg cgccaggcgg aaaccgcgaa tggggcgctg   1140

aaattcccat cgctgcacgc cagcccgccg atgctggccg ggaaacacat ctgggaggtg   1200

tcgaacatgg acaccgtgga cgcggcggtg accgccacca attacccgct ggtgcttggc   1260

gactggaagc agttcatcat caccgaccgg gtcgggtcga cggtggagct ggtgccgcac   1320

gtgttcggcg gcaaccgccg accgaccgga cagcgcggat tcttctgctg gttccgagtc   1380

ggttctgatg tgctggtgga caatgcgttc cgcgtgctga aggtgcagac caccgcg      1437
```

<210> SEQ ID NO 91
<211> LENGTH: 531
<212> TYPE: DNA
<213> ORGANISM: Mycobacteria tuberulosis

<400> SEQUENCE: 91

```
ttgagtagca tccttttccg cacggccgag ctgcggcctg gtgagggccg caccgtgtac     60

ggcgtcatcg tgccttatgg cgaggtgacc accgtccgcg acctcgacgg cgagttccgg    120

gaaatgttcg ctcctggcgc ttttcggcgc tccatcgctg agcgcggcca caaggtgaag    180

ctgctggtct cccacgacgc tcgaacccgc tacccggttg gccgggccgt cgagctgcgt    240

gaggagcctc acggcttgtt cggggcgttc gagcttgcga acaccccgga cggcgacgag    300

gccctggcga atgtgaaagc tggtgtggtg gacgcgtttt cggtgggttt ccggccgatc    360

cgggaccgcc gggaagggga tgtgatcgtg cgggtcgagg cggcgctgtt ggaggtctcc    420

ttgaccggcg ttccggccta tctgggcgcg cagatcgccg gtgtgcgcgc ggaatcgctt    480

gcagtcgttt cccgttcgct agccgaagcc aggttagccc tgatggattg g             531
```

<210> SEQ ID NO 92
<211> LENGTH: 624
<212> TYPE: DNA
<213> ORGANISM: Mycobacteria tuberculosis

<400> SEQUENCE: 92

```
ttgccatcgc cagcaaccgc ccgaccggac accgccacgg tgggagagcg tgtgcgcgct     60

caagttttat ggggcgtttt ttggcatcat ggcattcgcg acccgaaacc cggaaagagg    120

agggtggtgt tgaaaatggg taggcgtggt cccgcgccgg cgccggcgca gttgaaactc    180

ctcggcggcc gctcgccggg ccgtgattct ggcggccggc gggttacacc accggcggcg    240

ttcgagcgtg ttgcgccgga atgcccggat tggttgccgc caggcgctaa agacatgtgg    300

gggcgcgtcg ttcccgagct tgcggcatta aacctgctga aggagtccga ccttggggtg    360

ctgacctcct tctgcgtcgc ctgggatcag ctcatgcagg ctgtaacagc ctaccgtgaa    420

cagggtttca tcgcgacgaa cgcccgcagc cgacgggtga cggtgcatcc tgccgtggcc    480

gcggcccggg ccgcgacgag ggacgttttg gtgctcgcgc gcgaattggg gtgcacgcca    540

agcgctgagg cgaatttggc tgctgtgctg gcggcggcgg gggaccccga cgacgacgag    600

ttcaacccgt tcgccccaga ccgg                                           624
```

-continued

```
<210> SEQ ID NO 93
<211> LENGTH: 321
<212> TYPE: DNA
<213> ORGANISM: Mycobacteria tuberculosis

<400> SEQUENCE: 93

ttgacccaca agcgcactaa acgccagcca gccatcgccg cagggctcaa cgccccgcgt      60

cggaatcgcg ttgggcggca acatggttgg ccggccgacg ttccgtccgc cgagcagcgc     120

cgcgcccaac ggcagcgcga cctcgaggct atccgccgag cgtacgccga gatggtggcg     180

acatcacacg aaatcgacga cgacacagcc gaactggcgc tgttgtcgat gcatctcgac     240

gatgagcagc gccggcttga ggcggggatg aagctcggct ggcatccgta tcacttcccc     300

gacgaacccg acagcaaaca g                                               321


<210> SEQ ID NO 94
<211> LENGTH: 243
<212> TYPE: DNA
<213> ORGANISM: Mycobacteria tuberculosis

<400> SEQUENCE: 94

atgagcggcc acgcgttggc tgctcggacg ttgctggccg ccgcggacga gcttgtcggc      60

ggcccgccag tcgaggcttc ggccgccgcg ctggccggcg acgccgcggg cgcatggcgg     120

accgcggccg tcgagcttgc gcgagcgttg gtccgcgctg tggcggagtc gcacggcgtc     180

gcggccgttt tgttcgccgc gacggccgcc gcggcggcgg ccgtcgaccg gggtgatccg     240

ccg                                                                   243


<210> SEQ ID NO 95
<211> LENGTH: 1425
<212> TYPE: DNA
<213> ORGANISM: Mycobacteria tuberculosis

<400> SEQUENCE: 95

atggctgaca tcccctacgg ccgtgactat cccgacccga tctggtgtga cgaggacggc      60

cagccgatgc cgccggtcgg cgccgaattg ctcgacgaca ttagggcatt cttgcggcgg     120

ttcgtagtct atccaagcga ccatgaactg atcgcgcaca ccctctggat tgcgcattgc     180

tggtttatgg aggcgtggga ctcaacgccc cgaatcgctt ttttgtcacc ggaacccggc     240

tctggcaaga gccgcgcact cgaagtcacg gaaccgctag tgccccggcc ggtgcatgcc     300

atcaactgca caccggccta cctgttccgt cgggtggccg atccggtcgg gcggccgacc     360

gtcctgtacg acgagtgtga caccctgttt ggcccgaaag ctaaagaaca cgaggaaatt     420

cgcggcgtga tcaacgccgg ccaccgcaag ggagccgtcg cgggccgctg cgtcatccgc     480

ggcaagatcg ttgagaccga ggaactgcca gcgtactgtg cggtcgcctt ggccggcctc     540

gacgacctgc ccgacaccat catgtctcgg tcgatcgtgg tgaggatgcg caggagggca     600

ccaaccgaac ccgtggagcc gtggcgcccc cgcgtcaacg gccccgaggc cgagaagctg     660

cacgaccggt tggcgaactg ggcggccgcc attaacccgc tggaaagcgg ttggccggcg     720

atgccggacg gggtgaccga ccggcgcgcc gacgtctggg agtccctggt tgcggttgct     780

gacaccgcgg gcgggcactg gcccaaaacc gcccgtgcaa ccgcagaaac ggatgcaacc     840

gcaaatcgag gagccaagcc cagcataggc gtgctgctgc tgcgggatat ccgtcgagtc     900

ttcagcgacc gggaccggat gcgcaccagc gacatcctga ccggactgaa ccggatggag     960

gagggaccgt ggggctccat ccgccgcggc gacccgctcg acgcgcgcgg cctcgcgacc    1020
```

-continued

```
cggctcggca gatacggcat cgggccgaag ttccagcaca gtggtggcga accaccctac   1080

aaagggtatt cgcggaccca gttcgaggat gcgtggtccc ggtatctctc tgccgacgac   1140

gaaacccccg aggaacgaga tttatcggtt tccgcggttt ccgcggtttc accgccggtt   1200

ggcgatcccg gtgatgcaac cggcgcaacc gatgcaaccg atctcccgga ggcgggcgac   1260

ttgccgtacg agccgccggc gcccaacggg caccccaacg gcgacgcgcc gctgtgctcc   1320

gggccgggat gccccaacaa gctcctcagt actgaggcca aggccgccgg caaatgccgg   1380

ccctgccgag gtcgagcggc ggctagcgct cgggacggcg cccga                    1425
```

<210> SEQ ID NO 96
<211> LENGTH: 390
<212> TYPE: DNA
<213> ORGANISM: Mycobacteria tuberculosis

<400> SEQUENCE: 96

```
atgaccgccg tcggcgggtc gccgccgacg cgacgatgcc cggccacaga ggaccgggca     60

cccgcgacag tcgccacacc gtctagcacc gatcctaccg cgtcccgcgc cgtgtcgtgg    120

tggtcggtgc acgagtatgt cgcaccgacc ctggccgccg ccgtggaatg gccgatggcc    180

ggcaccccgg cgtggtgcga cctcgacgac accgacccgg tcaaatgggc cgcgatctgc    240

gacgctgctc ggcattgggc actccgggtg gagacgtgcc aggccgcgtc ggccgaggca    300

tcacgtgacg tatccgccgc cgccgactgg ccggcggtct ctcgggagat ccagcgtcgg    360

cgtgacgcct acattcggcg ggtggtggtc                                     390
```

<210> SEQ ID NO 97
<211> LENGTH: 258
<212> TYPE: DNA
<213> ORGANISM: Mycobacteria tuberculosis

<400> SEQUENCE: 97

```
atgtgcgcgt tcccgtcgcc gagtctcggg tggacggtct ctcacgagac cgaaaggccc     60

ggcatggcag acgctccccc gttgtcacgg cggtacatca cgatcagtga ggccgccgaa    120

tatctagcgg tcaccgaccg cacggtccgc cagatgatcg ccgacggccg cctacgcgga    180

taccgctccg gcacccgcct cgtccgtctg cgccgcgatg aggtcgacgg cgccatgcac    240

ccgttcggtg gtgccgca                                                  258
```

<210> SEQ ID NO 98
<211> LENGTH: 360
<212> TYPE: DNA
<213> ORGANISM: Mycobacteria tuberculosis

<400> SEQUENCE: 98

```
atggccgatg cggttaagta cgtagttatg tgcaactgcg acgacgaacc gggagcgctc     60

atcatcgcct ggatcgacga cgaacgaccc gccggcgggc acatacagat gcggtcgaac    120

acccgcttca ccgaaacaca gtggggccgc catatcgagt ggaaactcga atgccgggca    180

tgccgaaagt atgcgccgat atccgagatg accgccgcgg cgatcctcga cggtttcggg    240

gcgaagcttc acgagctgag aacgtcgacc atccccgacg ctgacgatcc atcaatagca    300

gaggcgcgac acgtaattcc gttcagcgca ttatgcttgc gcttgagcca gctaggcggg    360
```

<210> SEQ ID NO 99
<211> LENGTH: 1125
<212> TYPE: DNA
<213> ORGANISM: Mycobacteria tuberculosis

<400> SEQUENCE: 99
gtgacgcaaa ccggcaagcg tcagagacgc aaattcggtc gcatccgaca gttcaactcc 60
ggccgctggc aagccagcta caccggcccc gacggccgcg tgtacatcgc cccccaaaacc 120
ttcaacgcca agatcgacgc cgaagcatgg ctcaccgacc gccgccgcga aatcgaccga 180
caactatggt ccccggcatc gggtcaggaa gaccgccccg gagccccatt cggtgagtac 240
gccgaaggat ggctgaagca gcgtggaatc aaggaccgca cccgcgccca ctatcgcaaa 300
ctgctggaca accacatcct ggccaccttc gctgacaccg acctacgcga catcaccccg 360
gccgccgtgc gccgctggta cgccaccacc gccgtgggca caccgaccat gcgggcacac 420
tcctacagct tgctgcgcgc aatcatgcag accgccttgg ccgacgacct gatcgactcc 480
aacccctgcc gcatctcagg cgcgtccacc gcccgccgcg tccacaagat caggcccgcc 540
accctcgacg agctggaaac catcaccaaa gccatgcccg acccctacca ggcgttcgtg 600
ctgatggcgg catggctggc catgcgctac ggcgagctga ccgaattacg ccgcaaagac 660
atcgacctgc acggcgaggt tgcgcgggtg cggcgggctg tcgttcgggt gggcgaaggc 720
ttcaaggtga cgacaccgaa aagcgatgcg ggagtgcgcg acataagtat cccgccacat 780
ctgatacccg ccatcgaaga ccaccttcac aaacacgtca accccggccg ggagtccctg 840
ctgttcccat cggtcaacga ccccaaccgt cacctagcac cctcggcgct gtaccgcatg 900
ttctacaagg cccgaaaagc cgccggccga ccagacttac gggtgcacga ccttcgacac 960
tccggcgccg tgttggctgc atccaccggc gccacactgg ccgaactgat gcagcggcta 1020
ggacacagca cagccggcgc cgcactccgc taccagcacg ccgccaaggg ccgggaccgc 1080
gaaatcgccg cactgttaag caaactggcc gagaaccagg agatg 1125

<210> SEQ ID NO 100
<211> LENGTH: 225
<212> TYPE: DNA
<213> ORGANISM: Mycobacteria tuberculosis

<400> SEQUENCE: 100
gtgatagcgg gcgtcgacca ggcgcttgca gcaacaggcc aggctagcca gcgggcggca 60
ggcgcatctg gtggggtcac cgtcggtgtc ggcgtgggca cggaacagag gaacctttcg 120
gtggttgcac cgagtcagtt cacatttagt tcacgcagcc cagattttgt ggatgaaacc 180
gcaggtcaat cgtggtgcgc gatactggga ttgaaccagt ttcac 225

<210> SEQ ID NO 101
<211> LENGTH: 186
<212> TYPE: DNA
<213> ORGANISM: Mycobacteria tuberculosis

<400> SEQUENCE: 101
atgatcgagc agggccgcga ctgccgggac gtggtcaccc agctcgccgc ggtatcgcgc 60
gcactcgacc gcgccggatt caagatcgtt gcggcagggt tgaaggaatg cgtgtccggg 120
gccacggcca gcggcgcggc accgctgagt gcagctgagc tagaaaagct gttcctggcg 180
ctcgct 186

<210> SEQ ID NO 102
<211> LENGTH: 357
<212> TYPE: DNA
<213> ORGANISM: Mycobacteria tuberculosis -continued

<400> SEQUENCE: 102
atgtcggacc agccacgtca tcaccaggtc ctcgacgacc tgctgcccca acaccgcgct 60
ctacgtcacc agattcccca ggtgtaccag cgatttgtag ccctgggcga cgccgcgctt 120
accgacggcg ctctcagccg caaggtcaag gagcttgtgg cgctggcgat cgcggttgtg 180
caggggtgcg atggctgcgt cgcatcacac gcccaagccg cggtacgggc cggcgctaca 240
gcgcaagaag ccgctgaggc catcggggtc accatcttga tgcacggtgg accggccacc 300
atccacggtg ctcgtgccta cgcggcattt tgcgaattcg ctgacacaac gccgtcc 357

<210> SEQ ID NO 103
<211> LENGTH: 1854
<212> TYPE: DNA
<213> ORGANISM: Mycobacteria tuberculosis

<400> SEQUENCE: 103
atgtcctatc tcgtcgtggt gccggagttg gtcgcagcgg cggcaacaga tttggcgaac 60
atcggttcgt cgattagtgc agccaacgcg gccgcggcgg caccgaccac ggcactggtc 120
gcagccggcg gcgacgaggt atcggcggcc atagccgcgt tgttcggagc gcatgctcgg 180
gcatatcaag cgttgagtgc ccaggcggcg atgtttcatg aacagtttgt ccgggccctc 240
gccgccggcg gtaactccta cgccgtcgct gaggcggcaa ccgcgcaatc ggttcagcaa 300
gatctgctca acctgatcaa tgcgcccacc caggcgctgt tggggcgtcc gctgatcggc 360
aacggcgcca acgggctgcc gggtacgggc cagaacggcg gcgacggcgg gattctgtac 420
ggcaacggcg gcaacggtgg gtccggcggg gtcaaccagg ccggtggcaa tggcgggaat 480
gctgggctgt ggggcaatgg cggatccggc ggagccggcg ggaacgccac cactgccggc 540
cgcaacggct tcaacggggg cgccggggga agcggcggtt tgctgtgggg caatggcggt 600
gccggcgggg ccggtgggaa cggcggtccg gctccgctcg tgggcggggt gggcaccacc 660
ggtggcgccg gcgggaacgg cggcggcgcc gggttgttct acggtttcgg cggcgccggt 720
gggaacggcg ggatgggcgg ggtggcaccg agcaccggcc cctcgatggg catcctcccg 780
gccggcggtg tcggcgggcc tggtggctcc ggcggggcga gcgcgcttgc cttcggctcc 840
ggcggcgtcg gcggtgccgg tggcttgggc gggccgaccg atggcaccgt ccagggggtg 900
ggcggcttcg gcggtcaggg cggcaacggc gggcagagcg gcttgttgtt tggcaacgcg 960
ggagccggcg gggcaggcgc tgccggcgga gccggcaccg gcgacaccga gagcttcggc 1020
ggccacggcg gggccggcgg tgatggcggc gctgttggct tgatcggtaa cggcggggcc 1080
ggcggcaccg gatctcccgg cgctgtggtg ggtggtaacg gcggcgtcgg tggtctgggt 1140
ggcgccggca gtcccggggg tctgttgtac ggcaccgggg gggccggcgg caatggcgga 1200
ccgggtggtg acggtggtac tggcgcgacg gtgggctttg ccggctccgg cggtttcggc 1260
ggtgcggggg gcatcgccca gctgtttggc acgggtggca tgggtggtag cggcggtggt 1320
ataggcgctg gcaccacgac cgtggtgccg cccgacgtcg ccccggtggg tggcacaggc 1380
ggcaatggcg gtcgcgccgg gctgctgttg ggtgtgggtg gcatgggcgg taatggcggt 1440
gccaccagcg tcggcgggac gctctacgcc gccggtggaa acggcggcga cggcgggttg 1500
gtgtggggca acggtggcac cggcgggagc ggtggcgccg gcggggcggg cagcgtcggc 1560
aacggcggtg cgggtggcaa cgcggcactg ctgttcggca acggcggggc gggcggggcc 1620
ggcggcgccg gcggcatcgg tgccggcgga gccggcggct tcggcgcggt tctgtttggc 1680
aacggcgggg ctggcgggag cggtgccccc ggtggcatcg gcgccggtgg caatggcgga 1740
aacgcgctgc tggtcggcaa cggcggcaac ggtggggcag gtaccggtgg ggctgctggc 1800
ggtgccggtg gctcgggcgg gttgctattc ggccaaaatg ggatgcccgg gccg 1854

<210> SEQ ID NO 104
<211> LENGTH: 1242
<212> TYPE: DNA
<213> ORGANISM: Mycobacteria tuberculosis

<400> SEQUENCE: 104
gtgcatgagg tggctgctcg tgagcaacgt tcggacgggc cgatgaggct ggatgcgcag 60
ggccgactgc agcgttacga ggaggcgttc gctgactacg atgcaccgtt tgcgttcgta 120
gatctcgacg cgatgtgggg caatgccgat caactgcttg cgcgcgccgg cgacaagccg 180
atccgggtgg cgtcgaagtc gctgcgttgc cgaccactgc aacgcgaaat ccttgatgcc 240
agtgagcgat tcgacgggct attgacgttc acgcttaccg agacgctgtg gcttgccggc 300
caaggtttct cgaacctgtt gttggcctac ccgccgaccg accgggcggc attgcgtgcg 360
cttggcgagc tgacggccaa ggacccggac ggggcgccga tcgtgatggt ggacagcgtg 420
gagcaccttg acctgatcga gcgcacgacc gacaagccgg tacggctgtg tctggatttc 480
gatgccggct attggcgcgc cggcgggcgg ataaaaattg gttccaagcg ctcgccgctg 540
cacaccccgg agcaggctcg cgcactcgcg gtggagatcg cgcggcggcc ggcgctaacg 600
ttggcggcgt tgatgtgcta cgaggcccac attgcgggcc tcggtgacaa cgtcgccggc 660
aagcgggtcc acaacgcgat catccgtcgg atgcagcgca tgtcgttcga agagctgcgc 720
gagcgtcgtg cccgggccgt cgagctggtg cgcgaggtcg ccgacatcaa gatcgtcaac 780
gccggtggca ccggcgactt gcagctggtt gcgcaggagc cgttgattac cgaagcgacc 840
gccggctcgg gtttttacgc gccgacactg ttcgactcgt attcgacgtt cacgctgcag 900
cccgcggcga tgttcgcgct gccggtatgc cgtcgtcccg gtgcaaagac cgtgaccgcg 960
ctcgggggtg gctatttagc cagcggggtc ggggcgaagg accgcatgcc gactccctac 1020
ctgccggtcg ggctgaagct caatgcgctg gagggaacgg gcgaagttca gacaccgcta 1080
tccggtgatg cagcccgacg gctgaagctt ggcgacaagg tctacttccg ccacaccaag 1140
gccggtgagc tgtgtgagcg gttcgaccat ctgcatctgg tccgtggcgc tgaagtagtc 1200
gacaccgtcc ccacctaccg ggtgaaggg cgcaccttcc tc 1242

<210> SEQ ID NO 105
<211> LENGTH: 1284
<212> TYPE: DNA
<213> ORGANISM: Mycobacteria tuberculosis

<400> SEQUENCE: 105
atggacgagg cccacccggc tcacccggca gatgcggggc ggcccggtgg cccaattcaa 60
ggcgcgcgaa gaggagctgc catgacaccg atcaccgccc tgccgaccga gttggcggcc 120
atgcgcgagg tagtcgagac gctcgcaccc attgagcgtg ccgcgggcga gccgggtgag 180
cacaaggcgg ccgagtggat cgtcgagcgc ctgcgcacgg cgggcgcgca ggacgcgcgc 240
atcgaggagg agcagtacct cgacggctac ccgaggctgc acctcaagct gtcggtgatc 300
ggggtggcgg ccggcgtcgc gggcctgctc agcagacgtt tgcgcatccc cgccgcgctg 360
gccggggtgg gtgcggggct ggcaatcgcc gacgattgcg ccaacgggcc gcgcattgtg 420
cgcaaacgaa cggagacgcc ccggacgaca tggaacgcgg tagccgaggc cggtgatcct 480

-continued

```
gctggtcagc taacagttgt tgtgtgcgct caccacgacg ccgcgcacag cggcaagttt    540

ttcgaggctc atattgagga ggtaatggtc gagctgtttc ccgggattgt ggagcgcatc    600

gacacgcagc tgccgaactg gtgggggccg atcctcgcgc ccgcactcgc cggtgtcggc    660

gccctgcgcg gcagccggcc gatgatgatc gccggaacgg tgggtagcgc cctggccgcc    720

gctttgttcg ccgacatcgc gcgcagtccg gtcgtccccg gtgccaacga caatctctcc    780

gcggttgcgc tgctggtcgc gctggccgag cggctgcgcg agcggccggt gaagggcgtg    840

cgagtgttgc tcgtgtccct gggggccgag gaaacgttgc agggcgggat ctacgggttc    900

ctggcgcgac acaaacccga gctggaccgc gaccgcacat acttcctgaa cttcgacacc    960

atcggctcac ccgagctcat catgctcgag ggcgagggcc cgacggtcat ggaggactac   1020

ttctatcggc cattccggga tctggtcatc cgggcggccg agcgcgccga cgcgccgctg   1080

cggcgcggca tccggtcgcg caacagtacc gacgcggtgt tgatgagccg cgccggctac   1140

ccgaccgcgt gctttgtgtc gatcaaccgg cacaagtcgg tggccaatta ccacctgatg   1200

tccgatacac ctgagaatct ctgctatgag acggtgtccc acgccgtcac cgtcgccgaa   1260

tccgtgatca gggagctggc ccga                                          1284
```

<210> SEQ ID NO 106
<211> LENGTH: 1284
<212> TYPE: DNA
<213> ORGANISM: Mycobacteria tuberculosis

<400> SEQUENCE: 106

```
atgagcccga tatggagtaa ttggcctggt gagcaagtct gcgcgccgtc ggcgatcgta     60

cggccgacct cggaggctga gctggccgac gtgatcgcgc aggcggcgaa aagaggcgag    120

cgggtacgcg cggttggcag cgggcattcg tttaccgaca tcgcctgcac ggacggggtc    180

atgatcgaca tgaccggcct gcagcgggtc ctcgacgtgg accagccgac tggcctggtg    240

acggtcgagg ggggcgcaaa gctacgtgcg ctgggacccc aattggcgca acgacggctc    300

ggcctggaga accagggtga cgtggatccc caatccatca ccggcgcgac cgcgaccgcg    360

acgcacggaa ccggggtgcg tttccagaat ctgtcggcgc ggatcgtttc gctgcggctg    420

gtcaccgcgg gcggggaagt gctcagtctg tccgaaggtg acgattacct ggcggcacgg    480

gtttccctcg gcgcgctagg agtgatctca caggtcaccc tgcagacggt tccgctattc    540

acgttgcatc gccatgatca gcgacgctcg ctggcgcaga cgctggagcg cctcgacgag    600

ttcgtggacg gtaatgacca tttcgagttt ttcgtattcc cttacgcaga taaggcgttg    660

acgcgcacca tgcatcgcag tgacgagcag cccaaaccca cgcccgggtg gcagcgcatg    720

gtcggcgaga acttcgagaa cgggggattg agcctgatct gccagaccgg ccgtcgtttt    780

cctagtgtgg cgccgcgact gaaccgcctg atgacgaaca tgatgtcgtc ctccaccgtg    840

caagaccgcg cctacaaggt ctttgcgacc caacgcaagg tcaggttcac cgagatggag    900

tacgcgatcc cgcgtgaaaa cgggcgcgag gcgctccagc gtgtcatcga ccttgtgcgc    960

cgtcgcagct tgccgatcat gtttccgatt gaggtgcgat tctccgcccc cgacgattcc   1020

ttcctgtcga ccgcatatgg gcgcgacact tgctacatcg cggttcatca atacgccggt   1080

atggagttcg aaagctactt ccgcgccgtc gaggagatca tggacgacta cgccggtcgg   1140

ccacactggg gtaaacgtca ctatcagacc gccgccacgc ttcgtgagcg ctatccgcag   1200

tgggatcggt tcgccgcggt tcgcgatcgc ctcgatccgg accgggtgtt tctcaacgac   1260

tacacccggc gcgttctcgg tccc                                          1284
```

<210> SEQ ID NO 107
<211> LENGTH: 309
<212> TYPE: DNA
<213> ORGANISM: Mycobacteria tuberculosis

<400> SEQUENCE: 107
ttgggttcaa caggaggtag ccaacccatg acggcgaatc gagggcccgc tgcaatctcg 60
agcggctcga actctggccg cgttctcgac accgcccggg gtatcctcat cgctcttcgg 120
cggtgccccg cagagaccgc gttcgacgag ttgcacaacg ccgctcaacg gcacagattg 180
ccggtcttcg aaatagcttg ggcactagtg catttggcgg tcgagggaag cacgccatgc 240
cggagcttcg tcgatgccca gtcggcggct cggcgggagt ggggtcagct ttttgcgcat 300
gcggcggcg 309

<210> SEQ ID NO 108
<211> LENGTH: 744
<212> TYPE: DNA
<213> ORGANISM: Mycobacteria tuberculosis

<400> SEQUENCE: 108
gtgccgccta cggaaggaaa gtcgacaacg aatcgcgacg aaggcatcca ggtgctccgt 60
cgcgccgtcg ccgcgctgga cgaaatagct gccgaaccgg gacacctgcg cctagtcgat 120
ctctgcgagc ggctggggct ggccaaatcg acgactcgac gcttgctggt cggcctggtc 180
gaggtggggc tggttagtgt cgattcgcac ggccgcttcg cactgggcga gcgtttgctg 240
ggattcggaa gtgtcaccgg agcccacata gccgcggcgt tccggccgac cgtcgagcga 300
gttgcccgcg cgaccgacgg cgaaacggtc gacctgtcgg tactgcgcgg ccagcgaatg 360
tggtttgtcg accagatcga atcgtcttac cggctgcgtg cggtctcagc cgtcgggctc 420
cgcttcccgt tgaacggaac cgcgaatgga aaagcggcgc tggctgctct cgacgacgcc 480
gacgccgagg ccgcgctctg ccgtctggat cccatggtgg ccgaaggtct acggcgcgag 540
atcgtcgaga tccggcgcac cggtatcgct ttcgaccgca acgagcacac cccagggata 600
tccgcggctg cgatcgcacg acgcgccctg ggcgacaacg tgatcgcgat ctcggtgccg 660
gcgcccaccg cacgatttct ggaaaaagag cagcgcataa tcgccgcgtt gcgcgccgcc 720
gcggactcgc cggactggac tcgc 744

<210> SEQ ID NO 109
<211> LENGTH: 1218
<212> TYPE: DNA
<213> ORGANISM: Mycobacteria tuberculosis

<400> SEQUENCE: 109
atggcatccg tcgcccaacc cgttaggcgc cgcccaaagg accggaagaa gcagattttg 60
gatcaggccg ttggactgtt catcgaacgt ggcttccatt cggtcaaatt ggaggacatt 120
gccgaggcgg ccggggtgac cgcgcgcgcg ttgtatcgcc actacgacaa caagcaggcg 180
ttgctcgccg aagcgatccg aaccggccag gatcagtacc agagcgcgcg tcgtctcacc 240
gagggcgaga cggagccgac gccgcggccg ttgaacgccg atctggaaga cctgatcgcc 300
gcggcggtcg cctctcgggc gttgacggtg ctgtggcagc gcgaggcccg ctacctcaac 360
gaggacgacc gcacggcggt ccggcgccgc atcaacgcga tcgtcgccgg catgcgtgac 420
agcgtgctgc tggaggtgcc cgatctgagt ccacagcatt cggagttgcg ggcgtgggcg 480

-continued

```
gtgtccagca ctttgaccag cctgggccgg cacagcctaa gcctgccggg cgaggaactg    540
aaaaagcttc tctaccaggc gtgtatggcc gcggcaagga cgcctcccgt ctgcgaattg    600
ccgccactgc cggccggtga tgccgcacgc gacgaggccg acgtgctgtt ctcccgctac    660
gagaccctgc tggccgcggg cgcgcggctg ttccgtgcgc agggctatcc ggccgtcaac    720
accagcgaaa tcggcaaggg agccggcatc gcgggcccgg ggctgtaccg ttcgttttct    780
tccaaacagg ccatcctgga cgcgctcatc cgccgcctcg acgagtggcg ctgcctggag    840
tgcatccgag cgctacgagc gaatcagcaa gcggcacaac ggttgcgcgg ccttgtccaa    900
gggcacgttc ggatcagctt ggacgctccg gatctggtgg cagtgtcggt caccgaactg    960
tcgcacgcct ctgtcgaagt acgcgacggc tacctgcgaa atcagggcga ccgcgaggcc   1020
gtgtggatcg acctcatcgg caagctggta cccgcgacca gtgtcgccca ggggcgactg   1080
ctggtcgcgg cggcgattag cttcatcgaa gacgtcgctc gcacctggca tctcacgcgc   1140
tacgccggag tcgccgacga gatcagtggc ctggcgctgg cgatcctgac cagcggggca   1200
ggtaacctct tgcgcgca                                                 1218
```

<210> SEQ ID NO 110
<211> LENGTH: 795
<212> TYPE: DNA
<213> ORGANISM: Mycobacteria tuberculosis

<400> SEQUENCE: 110

```
atggtaatcg tggccgacaa ggcggccggt cgggtcgctg atccggtctt gcggccggtg     60
ggcgcgctgg gcgatttctt cgcgatgacg ctcgacacgt ccgtgtgcat gttcaagccg    120
cctttcgcgt ggcgtgaata cctacttcag tgctggttcg tggcgcgggt gtcgacgctg    180
cctggggtgt tgatgacgat cccatgggcg gtgatctcgg ggtttctctt caacgtcttg    240
ctgaccgaca tcggtgccgc ggacttttcc ggcaccggct gtgcgatctt caccgtgaac    300
caaagcgccc cgatcgtcac ggtcttggtg gtcgcgggcg cgggcgccac cgccatgtgc    360
gccgatctgg gtgcgcgcac catccgtgag gaactcgacg cactgcgggt gatgggcatc    420
aacccgatcc aagcgctagc ggctccgcgc gtgctggcgg ccaccacggt gtcgttggcg    480
ctgaattcgg tggtgaccgc gacggggctg atcggcgcgt tcttttgctc ggtgtttctc    540
atgcacgtct cggcgggggc atgggtgacc gggcttacca cgctgaccca caccgtggac    600
gtcgtcattt cgatgatcaa ggcgacgttg ttcgggctga tggccggact gatcgcctgc    660
tataagggca tgtcggtcgg tggcggcccg gccggagtcg gccgggcggt gaacgaaacc    720
gtggtgtttg ccttcatcgt cttgttcgtg atcaacatcg tcgtcaccgc ggtcggcatc    780
ccattcatgg tgtcc                                                     795
```

<210> SEQ ID NO 111
<211> LENGTH: 813
<212> TYPE: DNA
<213> ORGANISM: Mycobacteria tuberculosis

<400> SEQUENCE: 111

```
atgacggcag cgaaagccct tgtaagcgaa tggaatcgga tgggatcgca gatgcggttc     60
ttcgtcggca cgctggccgg gattcccgac gccctcatgc actaccgcgg cgagctgctg    120
cgggtgatcg cgcaaatggg gttggggacc ggggttcttg cggtgatcgg tggaacggtc    180
gcgatcgtcg ggttcttggc gatgaccacc ggcgcgatcg tggccgtgca gggctacaac    240
cagttcgctt cggtgggtgt ggaggcgctg accggcttcg cgtcggcctt cttcaacacc    300
```

-continued

```
cgcgagattc agcccggaac cgtgatggtc gcgctagcgg ccaccgtcgg tgccggtacc    360
accgctgcgc tgggggcgat gcggataaac gaggagatcg acgcgctcga ggtgatcggc    420
atccgcagca tcagctacct ggcgagcacc cgggtgctgg ccggagtggt cgtggccgtc    480
cctctgttct gtgtgggact gatgacggcc tacctggccg cgcgcgtcgg caccaccgcc    540
atctatggcc aggggtcggg cgtgtacgac cactacttca acacgttcct gcgcccgacc    600
gacgtgctct ggtcgtcggt tgaagtcgtc gtggtcgctc tgatgatcat gctggtgtgc    660
acctattacg gctacgccgc acatggcggg ccggccgggg ttggcgaggc ggtcggccgg    720
gccgtgcgtg cctcgatggt cgtcgcgtcg atcgcaatcc ttgtcatgac gctggccatc    780
tacggccagt cgcccaactt tcacctggcg acc                                  813
```

<210> SEQ ID NO 112
<211> LENGTH: 1275
<212> TYPE: DNA
<213> ORGANISM: M. tuberculosis

<400> SEQUENCE: 112

```
atgagacgcg ggccgggtcg acaccgtttg cacgacgcgt ggtggacgct gatcctgttc     60
gcggtgatcg gggtggctgt cctggtgacg gcggtgtcct tcacgggcag cttgcggtcg    120
actgtgccgg tgacgctggc ggccgaccgc tccgggctgg tgatggactc cggcgccaag    180
gtcatgatgc gcggtgtgca ggtcggccgg gtcgcccaga tcggtcggat cgagtgggcc    240
cagaacgggg cgagcctcag actggagatc gaccccgacc agatccggta catcccggcc    300
aatgtcgagg cacagatcag cgccaccacc gcattcggtg ccaagttcgt cgacctggtg    360
atgccgcaaa acccaagtcg tgcacggctg tccgctgggg cggtactgca ttcgaagaac    420
gtcagcacgg aaatcaacac cgtcttcgaa aacgtcgtcg acctgctcaa catgatcgac    480
ccgctgaaac tgaacgccgt gctgaccgcg gtcgccgacg ccgttcgcgg gcaaggtgaa    540
cggataggcc aggccaccac cgacctcaac gaggtgctgg aggcactcaa cgcacgcggc    600
gacaccatcg gcggcaactg gcgatcgctc aagaacttca ccgacaccta tgacgcggcc    660
gcccaagaca tcctgacgat cctgaacgcc gccagcacca ccagtgcgac cgtcgtgaat    720
cattcgacgc agctggatgc cttgctactc aacgccatcg gactatccaa cgctggcacc    780
aacctgcttg gcagcagccg agacaatctc gtcggcgcgg ccgacatcct ggcgccgacc    840
acgagcctgc tgttcaagta caaccccgaa tacacctgct tcctgcaggg cgccaagtgg    900
tatctcgaca acggcggcta tgcggcctgg ggcggggccg acgggcgcac gctacaactc    960
gatgtggcgc tactgttcgg caacgacccc tatgtctatc cggacaacct gccggttgtc   1020
gcggccaagg ggggtcccgg cggaaggccg ggatgcgggc cattgccgga tgccacccac   1080
aacttcccgg tgcgccagct ggtcaccaac accggatggg gaaccgggct ggacatccgg   1140
cccaaccccg gcatcgggca tccctgctgg gccaactact tcccggtgac ccgcgcggtg   1200
cccgagccgc cgtcgatccg tcagtgcatc ccgggccgg cgatcgggcc caaccccgcg    1260
gcgggggagc agcca                                                    1275
```

<210> SEQ ID NO 113
<211> LENGTH: 1026
<212> TYPE: DNA
<213> ORGANISM: Mycobacteria tuberculosis

<400> SEQUENCE: 113

-continued

```
atgagggaga acctgggggg cgtcgtggtg cgcctcggcg tcttcctggc ggtatgcctg     60
ctgacggcgt tcctgctgat tgccgtcttc ggggaggtgc gcttcggcga cggcaagacc    120
tactacgccg agttcgccaa cgtgtccaat ctgcgaacgg gcaagctggt gcgcatcgcc    180
ggcgtcgagg tcggcaaggt caccaggatc tccatcaacc ccgacgcgac ggtgcgggtg    240
cagttcaccg ccgacaactc ggtcaccctc acgcggggca cccgggcggt gatccgctac    300
gacaacctgt tcggtgaccg ctatttggcg ctggaggaag ggccggcgg actcgccgtt    360
cttcgtcccg gtcacacgat tccgttggcg cgcacccaac cggcgttgga tctggatgcc    420
ctgatcggtg gattcaagcc gctgtttcgt gcgctgaacc ccgagcaggt caacgcgctg    480
agcgaacagt tgctgcacgc gtttgccgga caggggccca cgatcgggtc attgctggcc    540
cagtccgcgg ccgtgaccaa caccctggcc gaccgtgatc ggctgatcgg gcaggtgatc    600
accaacctca acgtggtgct gggctcgctg ggcgctcaca ccgatcggtt ggaccaggcg    660
gtgacgtcgc tatcagcgtt gattcaccgg ctcgcgcaac gcaagaccga catctccaac    720
gccgtggcct acaccaacgc cgccgccggc tcggtcgccg atctgctgtc gcaggctcgc    780
gcgccgttgg cgaaggtggt tcgcgagacc gatcgggtgg ccggcatcgc ggccgccgac    840
cacgactacc tcgacaatct gctcaacacg ctgccggaca aataccaggc gctggtccgc    900
cagggtatgt acggcgactt cttcgccttc tacctgtgcg acgtcgtgct caaggtcaac    960
ggcaagggcg gccagccggt gtacatcaag ctggccggtc aggacagcgg gcggtgcgcg   1020
ccgaaa                                                              1026
```

<210> SEQ ID NO 114
<211> LENGTH: 1230
<212> TYPE: DNA
<213> ORGANISM: Mycobacteria tuberculosis

<400> SEQUENCE: 114

```
atgaaatcct tcgccgaacg caaccgtctg gccatcggca cagtcggcat cgtcgtcgtc     60
gccgccgttg cgctggccgc gctgcaatac cagcggctgc cgtttttcaa ccagggcacc    120
agggtctccg cctatttcgc cgacgccggc gggctgcgca ccggcaacac cgtcgaggtc    180
tccggctatc cggtgggaaa agtgtccagc atctcgctcg acggaccggg cgtgctggtg    240
gagttcaagg tcgacaccga cgtccgactc ggaaaccgca ccgaagtggc aatcaaaacc    300
aagggcttgt tgggcagcaa gttcctcgac gtcacccccc gcggggacgg ccgactcgat    360
tctccgatcc cgatcgagcg gaccacgtcg ccctaccaac tgcccgacgc ccttggcgat    420
ttggccgcca cgatcagcgg gttgcacacc gagcggctgt ccgaatcgct ggccaccctg    480
gcgcagacct ttgccgatac gccggcgcac ttccgcaacg ccatacacgg ggtggcccgg    540
ctcgcccaaa ccctcgatga gcgcgacaac caactgcgca gcctgctggc caacgcggcc    600
aaagccaccg gggtgctggc caaccgcacc gaccagatcg tcggcctggt gcgcgacacg    660
aatgtggtct tggcgcagct gcgcacccaa agcgccgccc tggaccggat ctgggcgaac    720
atctcggcgg tggccgaaca actgcggggc ttcatcgctg agaaccgcca gcagctgcgc    780
ccggcgctgg acaagctcaa cggggtgctg gctatcgtcg aaaaccgcaa agagcgtgtg    840
cggcaggcca tcccgctgat caacacctat gtcatgtcgc tgggtgagtc gctgtcgtcg    900
ggcccgttct tcaaggcata cgtggtgaac ctgctgccgg gtcagttcgt gcaaccgttc    960
atcagcgccg cgttctccga cctggggctc gacccggcca cgttgctgcc gtcgcagctg   1020
accgacccac cgaccggtca acccggaacc ccgccgttgc cgatgcccta cccgcgcacg   1080
```

ggccagggcg gtgagccgcg gctgacgctg cccgacgcga tcaccggcaa tcccggcgat 1140
ccgcgctatc cgtaccggcc ggagccgccc gcgccgccgc ccggcgggcc gccgcccggc 1200
ccgcccgcgc agcagccggg agaccaaccg 1230

<210> SEQ ID NO 115
<211> LENGTH: 1269
<212> TYPE: DNA
<213> ORGANISM: Mycobacteria tuberculosis

<400> SEQUENCE: 115
gtgacaacga aactcagacg tgcccgctcg gtgttggcga ccgccctggt gctggtcgcg 60
ggcgtgatcc tggccatgcg caccgccgac gccgccgccc gcacgaccgt ggtcgcctac 120
ttcgacaaca gcaacggtgt gttcgccggt gacgacgtgc tcattcgggg cgtgccggtg 180
ggcaagatcg tcaagatcga accgcaaccg ctgcgcgcca agatttcgtt ctggttcgac 240
cgcaaatacc gagtccccgc cgatgccgcc gcggcgatcc tgtcgccgca actggtgacc 300
ggccgggcca tccagctgac accgccgtat gccggcgggc cgaccatggc cgacggcaca 360
gtaatcccgc aagagcgcac cgtggtgccg gtggagtggg acgacttgcg ggcgcaactt 420
cagcggctga ccgcattgct gcagcccacc cggccgggcg gcgtcagcac gctgggtgcg 480
ctcatcaata ctgccgccga caacctgcgc gggcaaggcg ccaccatccg cgacaccatc 540
atcaaactgt cacaagcgat ttcggctctc ggtgaccaca gcaaagacat cttctccacc 600
gtgacgaacc tgtcgacgct ggtcacggcg ctgcatgaca gcgctgacct gctcgaacgg 660
ctcaaccaca acctggccgc ggtgacctcg ctgctggccg atggcccgga caagatcggt 720
caggcagccg aggacctcaa cgcggtcgta gccgacgtcg gcagcttcgc cgccgagcac 780
cgcgaggcga tcggcaccgc atcagacaag ctcgcgtcaa tcaccaccgc gctggtcgac 840
agcctcgacg acatcaagca gacgctgcat atcagcccga cggtgttgca gaacttcaac 900
aacatcttcg aaccggccaa cggcgcgctg accggcgcgc tggcgggcaa caacatggcc 960
aacccaatcg ccttcctgtg cggcgcgatc caggctgcct cccggctggg cggcgagcaa 1020
gcggccaaat tgtgcgtgca atacctggcg ccgatcgtga agaaccgcca gtacaactac 1080
ccgccgctgg gggcgaacct gttcgtcggg gcgcaggcca ggcctaacga ggtcacctac 1140
agcgaggact ggctgcggcc cgattacgtt gcaccagttg cggacacgcc gccagatccg 1200
gccgcggccg tgaccgtcga tcccgcgacc ggcctgcgcg gcatgatgat gccgccgggg 1260
ggtggctcg 1269

<210> SEQ ID NO 116
<211> LENGTH: 1131
<212> TYPE: DNA
<213> ORGANISM: M. tuberculosis

<400> SEQUENCE: 116
gtgaggatcg gcctgaccct ggtgatgatc gcggccgtgg tagcgagctg cggctggcgc 60
gggctgaatt cgctgccgct gcccggcacg cagggcaacg gcccggggtc cttcgcggtc 120
caggcgcagc tgccggatgt caacaacatc cagccgaact cgcgggtgcg ggttgccgac 180
gtgacggtcg gccacgtcac gaaaatcgag cgccaaggct ggcacgcgtt ggtgaccatg 240
cggctggatg gcgacgtcga tttgcccgcc aacgcaacgg ccaagatcgg caccaccagc 300
ctgctgggtt cctaccacat cgagctggcg ccaccgaaag gcgaagcgcg gcaaggcaag 360

-continued

```
ctgcgcgacg gttcactcat tgcgctgtca cacggtagcg cctacccaag caccgagcag    420

acgctggcag cgctgtcgct ggtgctcaac ggcggcggac tgggccaggt tcaagacatc    480

accgaggcgt tgagcaccgc gtttgccggc cgtgagcacg atctgcgcgg gctgattggg    540

cagctggaca ccttcaccgc atacctcaac aaccagtccg gtgacatcat cgcggccacc    600

gacagcctca accgcctcgt cggcaagttc gccgaccagc aacccgtctt cgatcgggcc    660

ctggccacca tccccgacgc gctcgcggtg ctggccgatg agcgggacac gctcgtcgag    720

gctgccgagc agctgagcaa gttcagcgcc ctgaccgtcg actcggtcaa caagaccacc    780

gcgaacctgg tcaccgaact gcggcaactc ggaccggtgt tggagtcgct ggccaattcc    840

ggtccggcgc tgacccgatc gctgtccctg ctggccacgt tcccgttccc gaacgagacg    900

ttccaaaatt tccagcgcgg cgaatacgcc aacctgaccg cgatcgtcga cctcacgctc    960

agccgcatcg accagggcct gttgaccggc acccgctggg agtgtcatct gacccagctc   1020

gagctgcagt ggggtcgcac cattgggcag ttccccagcc cgtgtaccgc gggctatcgg   1080

ggtaccccgg gcaatccgct gacgatcgcc taccgctggg atcaggggcc c            1131
```

<210> SEQ ID NO 117
<211> LENGTH: 1311
<212> TYPE: DNA
<213> ORGANISM: Mycobacteria tuberculosis

<400> SEQUENCE: 117

```
atgctgcatc taccgcgccg agtgatcgtt cagctggccg tctttaccgt gatcgcggtg     60

ggcgtgctgg ccatcacgtt cctgcatttc gtgaggctgc cggcgatgct tttcggcgtc    120

ggccgctaca cggtgacgat ggagctggtc gaagccggtg ggctgtatcg caccggcaat    180

gtcacctacc gcggctttga ggtgggccgg gtggcagcgg tgcggctcac cgacaccggg    240

gtgcaagcgg tgctggccct gaaatcgggc atcgatatcc cgtcggacct caaggccgag    300

gtgcacagcc acaccgcgat cggcgaaacc tacgtcgagt tgttgccgcg caacgccgcc    360

tcgccgccac tgaagaacgg cgatgtcatt gcgctggccg acacctcggt gccgcccgac    420

atcaacgacc tgctcagcgc ggccaacacc gcattggagg caatacctca cgagaacctg    480

cagaccgtca tcgacgagtc gtacaccgcg gtggccgggt tagggctcga actttcccgg    540

ctgatcaagg gctcggcgga actggcgatc gatgctcgcg cgaatctcga tccgctggtg    600

gcgctgatcg accgggcagg accggtgctg gattcgcaga cccacacctc ggatgcgatc    660

gcggcctggg cggcacagct ggccgcagtc accggccaat tgcagacaca cgactcggcg    720

gtcggcgatc tcatcgaccg ggcggtccg gcgttgggg agacgcgcca actgctcgag    780

cggctacaac ccaccgtgcc catcctgctg gccaacctgg tcagcgtcgg ccaggtcgca    840

ctcacctatc acaacgacat cgaacagctg ctggtggtgt tccccatggc catcgccgcc    900

gaacaggccg gcatcctggc caacctcaac accaagcagg cctaccgggg ccagtatctg    960

agcttcaacc tcaacctgaa cctgccgccg ccgtgcacca ccggctttct gccggcccag   1020

cagcggcgca ttcccacgtt cgaggactac ccggatcgcc cggccggtga tctgtactgc   1080

cgggtgcccc aggattcgcc gtttaacgtg cgcggcgccc gcaacatccc ctgtgaaacc   1140

gtgccgggca agcgcgcacc caccgtgaag ttatgcgaga gcgacgcgcc atacctgccg   1200

ctgaacgacg gctacaactg gaagggcgac cccaacgcca cggtgccggg tttggggtcc   1260

ggccaggaca tcccgcagac atggcaaacg atgctgctgc cgccgggcag c            1311
```

<210> SEQ ID NO 118
<211> LENGTH: 573
<212> TYPE: DNA
<213> ORGANISM: Mycobacteria tuberculosis

<400> SEQUENCE: 118
atgtcggtag cagtggattc cgacgccgag gatgacgccg tatcggagat cgctgaggca 60
gccggcgtgt cgccggcccc agccaaacca tccatgtcgg cgccgcggcg catgctgctg 120
ttcggcctgg tcgtcgtcgt cgctttggcg gtgctgttgt gttgctgggg atttcgcgtc 180
cagcgggcac gccatgcgca ggaccagcgt ggtcacttcc tgcaagcggc ccggcagtgc 240
gcgctgaacc taacgaccat cgactggcgc aacgccgagg cggatgtgcg ccgcattctg 300
gacggcgcca caggcgagtt ttacaacgac ttcgcccagc ggtcccagcc cttcgtcgaa 360
gtactgaggc acgcaaaggc cagcacggtc ggcacgatca ccgaggccgg gctgcagacg 420
cagaccgccg acacggccca ggcgctggtg gcggtgtccg tgcaaacgtc gaatgccggc 480
gaagccgacc cggttccacg agcgtggcga atgcgcatca ccgtgcagcg ggtcggcgac 540
cgggtcaagg tgtccgacgt cgggttcgtg ccg 573

<210> SEQ ID NO 119
<211> LENGTH: 480
<212> TYPE: DNA
<213> ORGANISM: Mycobacteria tuberculosis

<400> SEQUENCE: 119
gtgagctggt cgcgggtgat cgcctacggg ctgctgcccg ggctggcgtt ggcgctgacg 60
tgtggcgcgg gcttgctgaa atggcaggac ggcgccgtcc gcgacgccgc ggttgcccgt 120
gcggaatccg tgcgggccgc gaccgacggc accaccgcgc tgctgtctta ccggcccgac 180
accgtgcagc atgacctcga gagcgcgcga agcaggctca cgggcacgtt cctcgacgcc 240
tacacacagc tgacccacga cgtggtgatc cccggcgcac agcagaagca gatctcggcc 300
gtggccaccg tcgcggccgc ggcgtcggtg tcgacttccg ccgaccgcgc cgtcgtcctg 360
ctgttcgtaa accagaccat caccgtcggc aaggacgcgc cgaccaccgc cgcttccagc 420
gttcgggtga ccctcgacaa catcaacggg cgttggctga tctcgcaatt cgaaccgatc 480

<210> SEQ ID NO 120
<211> LENGTH: 375
<212> TYPE: DNA
<213> ORGANISM: Mycobacteria tuberculosis

<400> SEQUENCE: 120
gtgcagcgcc aatcattgat gccccagcag acccttgccg ccggcgtttt cgtgggtgcg 60
ctgctatgcg gtgtcgtgac ggcggcggtg ccaccacacg cacgcgccga cgtggtcgcc 120
tatctggtca acgtgacggt acgcccgggc tacaacttcg ccaacgccga cgccgcgttg 180
agttacggac atggcctctg cgagaaggtg tctcggggcc gcccttacgc acagatcatc 240
gccgacgtca aggctgattt cgacacccgc gaccaatacc aggcctcgta tctgctcagc 300
caggctgtca acgaactctg ccccgcgctg atctggcagt tgcgaaactc cgcagtcgac 360
aatcggcgct cgggc 375

<210> SEQ ID NO 121
<211> LENGTH: 663
<212> TYPE: DNA
<213> ORGANISM: Mycobacteria tuberculosis

<400> SEQUENCE: 121
atgtcgcgtc gagcatcggc cacgtgtgcc ttgtccgcga ccaccgccgt cgccataatg 60
gctgctcccg ccgcacgggc cgacgacaag cggctcaacg acggcgtggt cgccaacgtc 120
tacaccgttc aacgtcaggc cggctgcacc aacgacgtca cgatcaaccc gcaactacaa 180
ttggccgccc aatggcacac cctcgatctg ctgaacaacc ggcacctcaa cgacgacacc 240
ggttctgacg gatccacacc gcaagaccgc gcgcatgccg ccggcttccg cgggaaagtc 300
gctgaaaccg tggcgatcaa tcccgccgta gcgatcagcg gcatcgagtt gataaaccag 360
tggtactaca accccgcgtt tttcgcgatc atgtccgact gcgccaacac ccagatcggg 420
gtgtggtcag aaaacagccc ggatcgcacc gtcgtggtgg ccgtttacgg acagcccgat 480
cgaccttccg cgatgccgcc caggggagcg gtaaccggac cgccgtcccc ggtggccgcg 540
caagagaacg ttcctatcga ccccagcccc gactacgacg ccagcgacga gatcgaatac 600
ggcatcaact ggctgccatg gatcctgcgc ggcgtgtacc cgccgcccgc aatgccgccg 660
cag 663

<210> SEQ ID NO 122
<211> LENGTH: 405
<212> TYPE: DNA
<213> ORGANISM: Mycobacteria tuberculosis

<400> SEQUENCE: 122
gtgcggtgga ttgtcgacgg tatgaacgtg atcggaagtc gtccggatgg ttggtggcgc 60
gaccgccatc gcgcgatggt gatgctggtg gaaaggctcg aggggtgggc catcaccaag 120
gctcggggcg acgacgtgac ggtggtgttc gagcggccgc cgtcgaccgc catcccgtca 180
tcggtggtcg aagtggcgca tgcgcccaag gcggccgcca actcggccga cgacgagatc 240
gtccggctgg tccgatccgg cgcccagcca caagagattc gtgtggtgac atcggacaaa 300
gcgttgaccg accgggtccg agacttgggt gcggcagtct acccggcaga acggttccgt 360
gaccttatcg acccgcgcgg gtcgaacgcg gcccgccgca cgcag 405

<210> SEQ ID NO 123
<211> LENGTH: 1044
<212> TYPE: DNA
<213> ORGANISM: Mycobacteria tuberculosis

<400> SEQUENCE: 123
atgtctcaga cacccgctac aacccgcaaa acgtttcccg agatcagctc aagagcgtgg 60
gagcaccccg ccgaccggac cgccctttcc gcgctgcgcc ggctcaaagg cttcgaccag 120
atcttgaagc tgatgtcggg gatgttgcgg gaacggcagc accggctgct gtacctggcc 180
agcgcggcac gggtcgggcc gcggcagttc gccgacctcg acgcgctgct ggacgaatgc 240
gtggatgtgc tggacgcgtc ggcgaaaccc gaactctacg tgatgcagtc accaatcgcg 300
gatgccttca ccatcggcat gggcaagcca ttcaccgtga tcacctcggg gctgtacgac 360
ctggtgacac acgacgagat gcggttcgtg atgggccacg agctcggcca cgcactgtcc 420
ggccacgcgg tgtaccgcac gatgatgatg catctgctgc ggttggcccg gtcattcggc 480
gtcttgccgg ttggcggctg ggcgctgcgc gcaatcgtgg ctgcgctgct ggaatggcag 540
cgcaaatcgg agctgtccgg cgatcgcgct gggttgctgt gcgcgcagga tttggacacc 600
gcgctcaggg tggagatgaa gctcgctggc ggctgccggc tggacaagct ggactcggag 660
gccttcttgg ctcaggcccg ggaatacgag acatccggcg atatgcgcga cggggtgctc 720

```
aagctgctca acctggagct gcagacccat ccgttctctg tgctgcgggc tgccgccttg     780

actcactggg tggacaccgg cggctatgcc aaggtgatag ccggcgagta cccgcgtcgg     840

gccgacgacg gcaacgccaa atttgcagac gaccttggcg cggccgcccg gtactaccgg     900

gacggcttcg accagtccaa cgacccgctg atcaaaggta tccgcgacgg attcggtggc     960

atcgtcgagg gcgtgggacg ggcagcctcg aacgcggccg attcattggg ccgcaagatc    1020

accgagtggc ggcagccctc gaag                                           1044
```

```
<210> SEQ ID NO 124
<211> LENGTH: 564
<212> TYPE: DNA
<213> ORGANISM: Mycobacteria tuberculosis

<400> SEQUENCE: 124

atgactacgc gtccggcaac cgaccgccgc aagatgccca ctgggcggga agaggtagcg      60

gccgcaatcc tgcaggccgc caccgacctg ttcgccgagc gtgggccagc cgcgacgtcg     120

attcgcgaca tcgccgctcg atccaaggtc aaccacgggc tggtgtttcg tcacttcggc     180

accaaggacc aactggttgg ggccgtgctc gatcacctgg gcacgaagct gaccagactg     240

ttgcactccg aggcgcccgc tgacatcatc gaacgggctc tcgaccgaca tgggcgggtc     300

ttagcccggg cactgctgga cggatatccc gtgggccagc tgcaacagcg atttcccaat     360

gttgcggagc tgctcgacgc ggtacggcct cgctacgaca gcgacttggg cgcgcggctg     420

gcggtcgcgc acgcccttgc gctgcaattc ggttggcggc tctttgcgcc catgctgcgc     480

tcggcgacgg gtatcgacga gctgaccggt gacgaactac ggctgtccgt gaacgatgcg     540

gtagcccgga tcctggaacc gcac                                            564
```

```
<210> SEQ ID NO 125
<211> LENGTH: 702
<212> TYPE: DNA
<213> ORGANISM: Mycobacteria tuberculosis

<400> SEQUENCE: 125

gtgacgatat tgatcctgac cgacaacgtc cacgcccatg ctctggcggt cgatctgcag      60

gccaggcatg gcgatatgga cgtctatcag tcccccatcg gccagctgcc gggtgtcccg     120

cgatgtgatg tcgcagagcg cgtcgcggaa atcgtggagc ggtatgacct cgtcctttcc     180

ttccactgta aacagaggtt tcccgccgct ttgatcgatg gggtcaggtg tgtgaatgtt     240

catccgggtt tcaaccccta caaccgcggc tggtttcccc aggtcttctc gatcatcgac     300

gggcaaaaag tcggcgtgac gatccacgag atcgacgatc agttggacca tggtccgatc     360

atcgcccagc gggaatgcgc gatcgagtcg tgggattcct cgggaagtgt ctacgcccgg     420

ctgatggaca tcgagcgtga gttggtgctg gaacatttcg acgccatccg ggacggcagc     480

tacacggcta aatcgccggc caccgagggc aacctcaacc tgaaaaagga tttcgaacaa     540

ctccggcggc tagacctgaa cgagcgcgga acgtttgggc atttcctgaa tcgcctgcgc     600

gcgttgaccc atgatgattt ccgcaacgct tggttcgtcg atgcgtcagg ccgcaaggtg     660

tttgtccgcg tcgtgctcga accggagaag cccgcggaag cc                        702
```

```
<210> SEQ ID NO 126
<211> LENGTH: 1599
<212> TYPE: DNA
<213> ORGANISM: Mycobacteria tuberculosis
```

<400> SEQUENCE: 126

```
atgttagcct tcccttattt gatgactatg atcactccac ctaccttcga cgttgcgttc     60
atcggcagcg gggccgcgtg ctctatgact ctgctggaaa tggccgatgc cctgctgagc    120
agcccctcgg catcgcccaa gttgcgcatc gcggtggtgg agcgagacga gcagttctgg    180
tgcggaatcc cctatggcca acgctccagc atcggatcgc tggccattca gaagctcgac    240
gatttcgccg acgagccgga aaaggccgcc taccggatct ggctggagca gaacaagcag    300
cgctggctgg cgttcttcca ggcagagggc ggtgcggccg cggcccgctg gatctgcgac    360
aaccgcgacg cattggacgg caaccagtgg ggggagctct acctgccgcg gtttctcttc    420
ggtgtatttc tgtcggagca gatgattgcc gccatcgccg cgctcggcga gcgtgacctg    480
gccgaaatcg tcaccatccg cgctgaggcc atgagcgccc actccgcaga cggccactac    540
cgaatcggcc tccgcccgtc tggaaacggt ccaacggcaa ttgctgcagg caaagtggtt    600
gtggccattg gcagccccccc gaccaaagcc atccttgcga gcgattccga acccgcattc    660
acctatatca acgatttcta ctcccccggc ggggagagca acgttgcgcg actgcgcgat    720
tcgctcgacc gcgtcgagtc gtgggagaag cgcaacgtac tggtcgtggg ttccaacgcc    780
acctcgctgg aagcgctcta cctaatgcgt cacgacgcgc gcatccgcgc acgcgtccgg    840
tccatcaccg tcatctcgcg ctccggcgtg ctgccctaca tgatctgcaa tcagccgccg    900
gagtttgact tcccgcggct gcgcacgctg ctctgtacgg aagcgatcgc cgcggcggat    960
ctcatgtccg cgatccgcga cgatctcgcg acggccgaag aacgctcgtt gaacctggcc   1020
gatttgtacg acgccgttgc cgccctgttt gggcaggcgc tgcacaagat ggatctcgtg   1080
cagcaggaag agttcttctg cgtgcacggc atgaacttca ccaagttggt gcggcgtgcg   1140
ggacgcgatt gccgccaggc atccgaggag ctagccgcgg acggcacgct gagcctgctc   1200
gccggcgaag tactgcgcgt ggatgcctgc gcgtccggcc agccgttcgc caccatgacc   1260
taccgagccg cgggagccga gcatacccac cccgtcccct tcgctgcggt ggtgaattgt   1320
ggcggtttcg aggagctgga cacgtgttcc tcgccgttcc tggtcagcgc gatgcagaac   1380
gggctgtgcc gcccgaaccg caccaaccgt ggccttctgg ttaacgacga cttcgaggcc   1440
agcccaggtt tttgcgtcat cgggcccta gtcggcggca atttcactcc caagatccgt    1500
ttttggcacg tcgagagcgc accgcgcgtc cggtcgctgg cgaaatcgct ggcggccagc   1560
ctgcttgctt cgctccagcc cgtcgcactg gccccatgc                          1599
```

<210> SEQ ID NO 127
<211> LENGTH: 1236
<212> TYPE: DNA
<213> ORGANISM: Mycobacteria tuberculosis

<400> SEQUENCE: 127

```
atgaagatcc gaacgttatc cggctcggtg ctggagccgc cgtccgcagt acgcgcgacc     60
ccaggcacgt ccatgttaaa actcgagccg ggtggctcga cgatccccaa gatccccttc    120
atccgcccga gctttcccgg gccagccgag ctcgccgagg acttcgtaca gatcgcccag    180
gctaactggt acacgaactt cggtccgaac gagcggcggt ttgcccgcgc cctgcgcgac    240
tatctgggac ctcatctgca cgttgctacc ctcgccaacg gcaccctggc actcctcgcg    300
gcgctccacg tcagtttcgg cgccggtacg cgggaccgct acctgctgat gccgtcgttc    360
acgttcgtcg gcgtggctca ggctgcgcta tggactgggt accgtccctg gttcatcgac    420
atcgacgcca acacatggca gccatgcgtc cactccgccc gcgccgtcat cgaacgcttc    480
```

```
cgcgaccgga tcgccggcat cctgctggcc aatgtgttcg gcgtcggcaa tccccagatc    540
agcgtctggg aggagctcgc cgccgaatgg gagctaccga ttgtgctcga ctcggcggcc    600
ggcttcggct ccacgtacgc cgacggcgag cgcctcggtg gacgcggtgc atgcgagatc    660
ttctccttcc atgcgaccaa gccgttcgcg gttggtgagg gcggcgctct ggtttctcgc    720
gatccacggc tcgtcgagca cgcatacaag ttccagaact tcggcttggt gcaaacacgc    780
gagtccatcc agctcggaat gaacggcaag ctgtcggaga tcagcgccgc tattggccta    840
cgccaactag tcgggcttga tcgccgcctg gcaagtcgcc gcaaggtcct cgagtgctat    900
cgcaccggta tggccgacgc gggtgtgcgt ttccaggaca acgccaatgt tgcgtcgctc    960
tgtttcgcga gcgcttgctg cacgtccgcc gaccacaagg ccgcggttct gggtagcctg   1020
cgtaggcacg cgatcgaggc gcgcgactac tacaacccac cgcagcaccg acatccgtac   1080
tttgtgacga atgccgagtt agtcgagtcg accgatctag ccgtcacggc ggacatttgc   1140
tcgcgaatcg tgtcgctgcc agtccacgac cacatggccc cggatgacgt tgcccgggtc   1200
gtcgccgccg tgcaggaagc ggaggtgcgc ggtgaa                             1236
```

<210> SEQ ID NO 128
<211> LENGTH: 2358
<212> TYPE: DNA
<213> ORGANISM: Mycobacteria tuberculosis

<400> SEQUENCE: 128

```
atgatcaccg aggacgcctt ccccgtcgaa ccgtggcagg tccgcgagac caagctcaac     60
ctgaacctgc tggcccagtc cgaatcccta ttcgccttgt ccaacgggca cattggatta    120
cgcggcaacc tcgacgaggg cgaacccttc ggactgccgg gcacctacct gaactctttc    180
tacgaaatcc ggccgctgcc gtacgccgag gccggttatg gatatccgga ggccggccag    240
accgttgtcg acgtcaccaa cggcaagatc tttcgcctgt tggtcggcga cgagccgttc    300
gacgtccggt atggcgaatt gatctcccac gaacggatcc tcgacctgcg cgccgggacg    360
ctgacccgcc gcgcgcactg gcgctcaccg gcgggcaagc aagtcaaagt gacgtccacc    420
cggctggtgt cgctggccca ccgcagcgtc gcggcgatcg agtacgtcgt cgaggcaatc    480
gaggaattcg ttcgcgtgac cgtgcagtcc gaactcgtca ccaacgagga cgtaccggag    540
acctcggccg acccgcgggt gtcggccatc ctggacaggc cgctacaggc cgtcgagcac    600
gaacgcaccg agcggggtgc acttctcatg caccgcaccc gagccagcgc gctgatgatg    660
gccgcaggga tggaacacga ggtcgaggtt cccgggcggg tcgagatcac caccgacgcc    720
cgcccggacc tggcccgaac caccgtgatc tgcgggctgc gcccgggaca gaagctgcgc    780
atcgtcaaat acctggccta tggctggtcc agcctgcgct cccgcccggc gctgcgcgac    840
caggccgccg gcgcgctgca cggtgcccgc tacagcggct ggcaggggct gctggacgcg    900
caacgcgcct acctcgacga cttctgggac agcgcggacg tggaggtcga gggcgacccg    960
gaatgtcagc aagcggtgcg tttcgggtta tttcacctgt tgcaggccag cgcgcgcgcc   1020
gaacgccgcg cgatccccag caaggggctc accggaaccg ggtatgacgg ccacgccttt   1080
tgggacaccg aaggtttcgt gctaccggtg ctcacctaca ccgcaccgca tgcggtcgcc   1140
gacgcgctgc ggtggcgggc gtcgacgttg gacctggcca aggagcgggc ggccgagctc   1200
ggcctggaag gtgccgcctt tccctggcgg accatccgcg gacaggagtc ctcggcctac   1260
tggccggccg gcacggcggc ctggcacatc aacgccgaca tcgcgatggc gttcgagcgg   1320
```

-continued

```
taccgcatcg tcaccggcga cggttcgctg gaggaggaat gcggccttgc ggtgctgatc   1380

gagaccgccc ggctgtggct ctcgctcggg caccacgacc gccacggcgt ctggcacctc   1440

gacggggtca ccggtcccga cgagtacacg gcggtcgtcc gcgacaacgt gttcacgaat   1500

ctgatggcgg cgcacaatct gcacaccgcc gccgatgctt gcttgcgcca ccccgaggcg   1560

gcggaggcca tgggtgtcac caccgaggag atggccgcct ggcgcgacgc ggccgacgcc   1620

gccaacattc cctacgacga ggaactcggt gtccaccagc agtgtgaagg gttcaccacc   1680

cttgcggagt gggatttcga agccaacacc acttatccgt tgctactgca cgaggcctac   1740

gtgcgcttgt atcccgcaca ggtgatcaag caggccgacc tggtgctggc gatgcagtgg   1800

cagagtcacg cgttcacgcc cgagcagaag gcgcgcaacg tcgactacta cgaacggcgc   1860

atggtgcgcg actcgtcgtt gtcggcctgc actcaggcgg tgatgtgcgc cgaggtcggc   1920

catctcgagt tggcccacga ctatgcctac gaagccgccc tgatcgacct gcgcgacctg   1980

caccgcaaca cccgtgacgg cctacacatg gcttcgctgg ccggagcctg gacggcgctg   2040

gtcgtaggct tcggcggcct acgcgacgac gagggcatcc tgtccatcga tccgcagctg   2100

cccgacggca tctcgcggct gcggttccgg ctgcgatggc gcggcttccg gctgatcgtc   2160

gacgccaacc acaccgacgt caccttcatc cttggcgacg gtcccggcac ccagctgacc   2220

atgcgccacg ccggccaaga tctgacgctg cacacggaca caccgtccac catcgccgtg   2280

cgcacccgta agccgctgct gccgccacca ccgcagccgc caggccgcga gccagtgcac   2340

cgccgggctt tagcccgg                                                  2358
```

<210> SEQ ID NO 129
<211> LENGTH: 786
<212> TYPE: DNA
<213> ORGANISM: Mycobacteria tuberculosis

<400> SEQUENCE: 129

```
atggcgaact ggtatcgccc gaactatccg gaagtgaggt cccgcgtgct gggtctgccc     60

gagaaggtgc gtgcttgcct gttcgacctc gacggtgtgc tcaccgatac cgcgagcctg    120

cataccaagg cgtggaaggc catgtttgac gcctacctag ccgagcgagc cgagcgcacc    180

ggcgaaaaat tcgttccctt cgaccctgcc gcggactatc acacgtatgt ggacggcaag    240

aaacgcgaag acggcgttcg atcgtttctg agcagccgcg ccatcgaaat acccgacggt    300

tccccggatg acccgggcgc cgccgagacg gtgtatggcc tgggcaaccg caagaacgac    360

atgttgcaca agctgctgcg cgacgatggg gcccaggtgt tcgacgggtc gcggcgctac    420

ctggaggcgg tcacggccgc gggtctcggt gtggccgtgg tgtcttcgag cgccaacacc    480

cgcgacgtgc tcgcgaccac cggtctggac cggttcgtcc agcagcgggt ggacggcgtg    540

acgttgcgcg aagagcacat cgccggcaag ccggcccccg actccttcct gcgcgcggca    600

gaactgttgg gggttacccc cgacgcggcg gcggtgttcg aggacgccct gtccggggtg    660

gcggccggcc gcgccggcaa cttcgccgta gtggtgggca tcaaccgaac gggccgggcg    720

gctcaggccg cccagttgcg ccgccatggc gccgacgtgg tggtaaccga tctcgccgag    780

ctgctg                                                               786
```

<210> SEQ ID NO 130
<211> LENGTH: 60
<212> TYPE: DNA
<213> ORGANISM: M. tuberculosis
<220> FEATURE:
<221> NAME/KEY: misc_feature -continued

```
<222> LOCATION: (1)...(60)
<223> OTHER INFORMATION: n = A,T,C or G
<221> NAME/KEY: misc_feature
<222> LOCATION: 2, 55
<223> OTHER INFORMATION: n = A,T,C or G

<400> SEQUENCE: 130

antagtaatg tgcgagctga gcgatgtcgc cgctcccaaa aattaccaat ggttnggtca     60


<210> SEQ ID NO 131
<211> LENGTH: 60
<212> TYPE: DNA
<213> ORGANISM: M. tuberculosis

<400> SEQUENCE: 131

agtagtaatg tgcgagctga gcgatgtcgc cgctcccaaa aattaccaat ggtttggtca     60


<210> SEQ ID NO 132
<211> LENGTH: 60
<212> TYPE: DNA
<213> ORGANISM: M. tuberbulosis

<400> SEQUENCE: 132

tgacgccttc ctaaccagaa ttgtgaattc atacaagccg tagtcgtgca gaagcgcaac     60


<210> SEQ ID NO 133
<211> LENGTH: 60
<212> TYPE: DNA
<213> ORGANISM: M. tuberculosis

<400> SEQUENCE: 133

tgacgccttc ctaaccagaa ttgtgaattc atacaagccg tagtcgtgca gaagcgcaac     60


<210> SEQ ID NO 134
<211> LENGTH: 11
<212> TYPE: DNA
<213> ORGANISM: M. tuberculosis

<400> SEQUENCE: 134

actcttggag t                                                          11


<210> SEQ ID NO 135
<211> LENGTH: 11
<212> TYPE: DNA
<213> ORGANISM: M. tuberculosis

<400> SEQUENCE: 135

actcttggag t                                                          11


<210> SEQ ID NO 136
<211> LENGTH: 49
<212> TYPE: DNA
<213> ORGANISM: M. tuberculosis
<220> FEATURE:
<221> NAME/KEY: misc_feature
<222> LOCATION: (1)...(49)
<223> OTHER INFORMATION: n = A,T,C or G
<221> NAME/KEY: misc_feature
<222> LOCATION: 15, 24
<223> OTHER INFORMATION: n = A,T,C or G

<400> SEQUENCE: 136

gtggcctaca acggngctct ccgnggcgcg ggcgtaccgg atatcttag                 49


<210> SEQ ID NO 137
```

-continued

```
<211> LENGTH: 49
<212> TYPE: DNA
<213> ORGANISM: M. tuberculosis

<400> SEQUENCE: 137

gcggcctaca acggcgctct ccgcggcgcg ggcgtaccgg atatcttag               49
```

MOLECULAR DIFFERENCES BETWEEN SPECIES OF THE *M. TUBERCULOSIS* COMPLEX

This invention was made with Government support and you should include the following language in the application: "This invention was made with Governement support under contract AI01137, AI35969 awarded by the National Institutes of Health. The Government has certain rights in this invention."

Tuberculosis is an ancient human scourge that continues to be an important public health problem worldwide. It is an ongoing epidemic of staggering proportions. Approximately one in every three people in the world is infected with *Mycobacterium tuberculosis*, and has a 10% lifetime risk of progressing from infection to clinical disease. Although tuberculosis can be treated, an estimated 2.9 million people died from the disease last year.

There are significant problems with a reliance on drug treatment to control active *M. tuberculosis* infections. Most of the regions having high infection rates are less developed countries, which suffer from a lack of easily accessible health services, diagnostic facilities and suitable antibiotics against *M. tuberculosis*. Even where these are available, patient compliance is often poor because of the lengthy regimen required for complete treatment, and multidrug-resistant strains are increasingly common.

Prevention of infection would circumvent the problems of treatment, and so vaccination against tuberculosis is widely performed in endemic regions. Around 100 million people a year are vaccinated with live bacillus Calmette-Guerin (BCG) vaccine. BCG has the great advantage of being inexpensive and easily administered under less than optimal circumstances, with few adverse reactions. Unfortunately, the vaccine is widely variable in its efficacy, providing anywhere from 0 to 80% protection against infection with *M. tuberculosis.*

BCG has an interesting history. It is an attenuated strain of *M. bovis*, a very close relative of *M. tuberculosis*. The *M. bovis* strain that became BCG was isolated from a cow in the late 1800's by a bacteriologist named Nocard, hence it was called Nocard's bacillus. The attenuation of Nocard's bacillus took place from 1908 to 1921, over the course of 230 in vitro passages. Thereafter, it was widely grown throughout the world, resulting in additional hundreds and sometime thousands of in vitro passages. Throughout its many years in the laboratory, there has been selection for cross-reaction with the tuberculin skin test, and for decreased side effects. The net results have been a substantially weakened pathogen, which may be ineffective in raising an adequate immune response.

New antituberculosis vaccines are urgently needed for the general population in endemic regions, for HIV-infected individuals, as well as health care professionals likely to be exposed to tubercle bacilli. Recombinant DNA vaccines bearing protective genes from virulent *M. tuberculosis* are being developed using shuttle plasmids to transfer genetic material from one mycobacterial species to another, for example see U.S. Pat. No. 5,776,465. Tuberculosis vaccine development should be given a high priority in current medical research goals.

Relevant Literature

Mahairas et al. (1996) *J Bacteriol* 178(5):1274–1282 provides a molecular analysis of genetic differences between *Mycobacterium bovis* BCG and virulent *M. bovis*. Subtractive genomic hybridization was used to identify genetic differences between virulent *M. bovis* and *M. tuberculosis* and avirulent BCG. U.S. Pat. No. 5,700,683 is directed to these genetic differences.

Cole et al. (1998) *Nature* 393:537–544 have described the complete genome of *M. tuberculosis*. To obtain the contiguous genome sequence, a combined approach was used that involved the systematic sequence analysis of selected large-insert clones as well as random small-insert clones from a whole-genome shotgun library. This culminated in a composite sequence of U.S. Pat. No. 4,411,529 base pairs, with a G+C content of 65.6%. 3,924 open reading frames were identified in the genome, accounting for ~91% of the potential coding capacity.

*Mycobacterium tuberculosis* (*M. tb.*) genomic sequence is available at several internet sites.

SUMMARY OF THE INVENTION

Genetic markers are provided that distinguish between strains of the *Mycobacterium tuberculosis* complex, particularly between avirulent and virulent strains. Strains of interest include *M. bovis, M. bovis* BCG strains, *M. tuberculosis* (*M. tb.*) isolates, and bacteriophages that infect mycobacteria. The genetic markers are used for assays, e.g. immunoassays, that distinguish between strains, such as to differentiate between BCG immunization and *M. tb.* infection. The protein products may be produced and used as an immunogen, in drug screening, etc. The markers are useful in constructing genetically modified *M. tb.* or *M. bovis* cells having improved vaccine characteristics.

DETAILED DESCRIPTION OF THE EMBODIMENTS

Specific genetic deletions are identified that serve as markers to distinguish between avirulent and virulent mycobacteria strains, including *M. bovis, M. bovis* BCG strains, *M. tuberculosis* (*M. tb.*) isolates, and bacteriophages that infect mycobacteria. These deletions are used as genetic markers to distinguish between the different mycobacteria. The deletions may be introduced into *M. tb.* or *M. bovis* by recombinant methods in order to render a pathogenic strain avirulent. Alternatively, the deleted genes are identified in the *M. tb.* genome sequence, and are then reintroduced by recombinant methods into BCG or other vaccine strains, in order to improve the efficacy of vaccination.

The deletions of the invention are identified by comparative DNA hybridizations from genomic sequence of mycobacterium to a DNA microarray comprising representative sequences of the *M. tb.* coding sequences. The deletions are then mapped to the known *M. tb.* genome sequence in order to specifically identify the deleted gene(s), and to characterize nucleotide sequence of the deleted region.

Nucleic acids comprising the provided deletions and junctions are used in a variety of applications. Hybridization probes may be obtained from the known *M. tb.* sequence which correspond to the deleted sequences. Such probes are useful in distinguishing between mycobacteria. For example, there is a 10% probability that an *M. tb.* infected person will progress to clinical disease, but that probability may vary depending of the particular infecting strain. Analysis for the presence or absence of the deletions provided below as "*M. tb.* variable" is used to distinguish between different *M. tb.* strains. The deletions are also useful in identifying whether a patient that is positive for a tuberculin skin test has been infected with *M. tb.* or with BCG.

In another embodiment of the invention, mycobacteria are genetically altered to delete sequences identified herein as absent in attenuated strains, but present in pathogenic strains, e.g. deletions found in BCG but present in *M. tb.* H37Rv. Such genetically engineered strains may provide superior vaccines to the present BCG isolates in use. Alternatively, BCG strains may be "reconstructed" to more closely resemble wild-type *M. tb.* by inserting certain of the deleted sequences back into the genome. Since the protein products of the deleted sequences are expressed in virulent mycobacterial species, the encoded proteins are useful as immunogens for vaccination.

The attenuation (loss of virulence) in BCG is attributed to the loss of genetic material at a number of places throughout the genome. The selection over time for fewer side-effects resulting from BCG immunization, while retaining cross-reactivity with the tuberculin skin test, has provided an excellent screen for those sequences that engender side effects. The identification of deletions that vary between BCG isolates identifies such sequences, which may be used in drug screening and biological analysis for the role of the deleted genes in causing untoward side effects and pathogenicity.

Identification of *M. Tuberculosis* Complex Deletion Markers

The present invention provides nucleic acid sequences that are markers for specific mycobacteria, including *M. tb., M. bovis*, BCG and bacteriophage. The deletions are listed in Table 1. The absence or presence of these marker sequences is characteristic of the indicated isolate, or strain. As such, they provide a unique characteristic for the identification of the indicated mycobacteria. The deletions are identified by their *M. tb.* open reading frame ("Rv" nomenclature), which corresponds to a known genetic sequence, and may be accessed as previously cited. The junctions of the deletions are provided by the designation of position in the publicly available *M. tb.* sequence.

TABLE I

| SEQ ID | rd | rv_num | orf_Id | breakpoint |
|---|---|---|---|---|
| SEQ ID NO:1 | RD01 | Rv3871 | MTV027.06 | "H37Rv, segment 160: 7534, 16989" |
| SEQ ID NO:2 | RD01 | Rv3872 | MTV027.07 | "H37Rv, segment 160: 7534, 16989" |
| SEQ ID NO 3 | RD01 | Rv3873 | MTV027.08 | "H37Rv, segment 160: 7534, 16989" |
| SEQ ID NO:4 | RD01 | Rv3874 | MTV027.09 | "H37Rv, segment 160: 7534, 16989" |
| SEQ ID NO:5 | RD01 | Rv3875 | MTV027.10 | "H37Rv, segment 160: 7534, 16989" |
| SEQ ID NO:6 | RD01 | Rv3876 | MTV027.11 | "H37Rv, segment 160: 7534, 16989" |
| SEQ ID NO:7 | RD01 | Rv3877 | MTV027.12 | "H37Rv, segment 160: 7534, 16989" |
| SEQ ID NO:8 | RD01 | Rv3878 | MTV027.13 | "H37Rv, segment 160: 7534,16989" |
| SEQ ID NO:9 | RD01 | Rv3879c | MTV027.14c | "H37Rv, segment 160: 7534,16989" |
| SEQ ID NO:10 | RD02 | Rv1988 | MTCY39.31c | "H37Rv segment 88: 14211, segment 89: 8598" |
| SEQ ID NO:11 | RD02 | Rv1987 | MTCY39.32c | "H37Rv segment 88: 14211, segment 89: 8598" |
| SEQ ID NO:12 | RD02 | Rv1986 | MTCY39.33c | "H37Rv segment 88: 14211, segment 89: 8598" |
| SEQ ID NO:13 | RD02 | Rv1985c | MTCY39.34 | "H37Rv segment 88: 14211, segment 89: 8598" |
| SEQ ID NO:14 | RD02 | Rv1984c | MTCY39.35 | "H37Rv segment 88: 14211, segment 89: 8598" |
| SEQ ID NO:15 | RD02 | Rv1983 | MTCY39.36c | "H37Rv segment 88: 14211, segment 89: 8598" |
| SEQ ID NO:16 | RD02 | Rv1982c | MTCY39.37 | "H37Rv segment 88: 14211, segment 89: 8598" |
| SEQ ID NO:17 | RD02 | Rv1981c | MTCY39.38 | "H37Rv segment 88: 14211, segment 89: 8598" |
| SEQ ID NO:18 | RD02 | Rv1980c | MTCY39.39 | "H37Rv segment 88: 14211, segment 89: 8598" |
| SEQ ID NO:19 | RD02 | Rv1979c | MTCY39.40 | "H37Rv segment 88: 14211, segment 89: 8598" |
| SEQ ID NO:20 | RD02 | Rv1978 | MTV051.16 | "H37Rv segment 88: 14211, segment 89: 8598" |
| SEQ ID NO:21 | RD03 | Rv1586c | MTCY336.18 | "H37Rv, segment 70: 7677, 16923" |
| SEQ ID NO:22 | RD03 | Rvl585c | MTCY336.19 | "H37Rv, segment 70: 7677, 16923" |
| SEQ ID NO:23 | RD03 | Rv1584c | MTCY336.20 | "H37Rv, segment 70: 7677, 16923" |
| SEQ ID NO 24 | RD03 | Rv1583c | MTCY336.21 | "H37Rv, segment 70: 7677, 16923" |
| SEQ ID NO:25 | RD03 | Rv1582c | MTCY336.22 | "H37Rv, segment 70: 7677, 16923" |
| SEQ ID NO:26 | RD03 | Rv1581c | MTCY336.23 | "H37Rv, segment 70: 7677, 16923" |
| SEQ ID NO:27 | RD03 | Rvl580c | MTCY336.24 | "H37Rv, segment 70: 7677, 16923" |
| SEQ ID NO:28 | RD03 | Rv1579c | MTCY336.25 | "H37Rv, segment 70: 7677, 16923" |
| SEQ ID NO:29 | RD03 | Rv1578c | MTCY336.26 | "H37Rv, segment 70: 7677, 16923" |
| SEQ ID NO:30 | RD03 | Rv1577c | MTCY336.27 | "H37Rv, segment 70: 7677, 16923" |
| SEQ ID NO:31 | RD03 | Rv1576c | MTCY336.28 | "H37Rv, segment 70: 7677, 16923" |
| SEQ ID NO:32 | RD03 | Rv1575 | MTCY336.29c | "H37Rv, segment 70: 7677, 16923" |
| SEQ ID NO:33 | RD03 | Rv1574 | MTCY336.30c | "H37Rv, segment 70: 7677, 16923" |
| SEQ ID NO:34 | RD03 | Rv1573 | MTCY336.31c | "H37Rv, segment 70: 7677, 16923" |
| SEQ ID NO:35 | RD04 | Rv0221 | MTCY08D5.16 | "H37Rv, segment 12: 17432, 19335" |
| SEQ ID NO:36 | RD04 | Rv0222 | MTCY08D5.17 | "H37Rv, segment 12: 17432, 19335" |
| SEQ ID NO:37 | RD04 | Rv0223c | MTCY08D5.18 | "H37Rv, segment 12: 17432, 19335" |
| SEQ ID NO:38 | RD05 | Rv3117 | MTCY164.27 | "H37Rv, segment 135: 27437, 30212" |
| SEQ ID NO:39 | RD05 | Rv3118 | MTCY164.28 | "H37Rv, segment 135: 27437, 30212" |
| SEQ ID NO:40 | RD05 | Rv3119 | MTCY164.29 | "H37Rv, segment 135: 27437, 30212" |
| SEQ ID NO:41 | RD05 | Rv3120 | MTCY164.30 | "H37Rv, segment 135: 27437, 30212" |
| SEQ ID NO:42 | RD05 | Rv3121 | MTCY164.31 | "H37Rv, segment 135: 27437, 30212" |
| SEQ ID NO:43 | RD06 | Rv1506c | MTCY277.28c | "H37Rv, segment 65: 23614, 36347" |
| SEQ ID NO:44 | RD06 | Rv1507c | MTCY277.29c | "H37Rv, segment 65: 23614, 36347" |
| SEQ ID NO:45 | RD06 | Rv1508c | MTCY277.30c | "H37Rv, segment 65: 23614, 36347" |
| SEQ ID NO:46 | RD06 | Rv1509 | MTCY277.31 | "H37Rv, segment 65: 23614, 36347" |
| SEQ ID NO:47 | RD06 | Rv1510 | MTCY277.32 | "H37Rv, segment 65: 23614, 36347" |
| SEQ ID NO:48 | RD06 | Rv1511 | MTCY277.33 | "H37Rv, segment 65: 23614, 36347" |
| SEQ ID NO:49 | RD06 | Rv1512 | MTCY277.34 | "H37Rv, segment 65: 23614, 36347" |
| SEQ ID NO:50 | RD06 | Rv1513 | MTCY277.35 | "H37Rv, segment 65: 23614, 36347" |
| SEQ ID NO:51 | RD06 | Rv1514c | MTCY277.36c | "H37Rv, segment 65: 23614, 36347" |
| SEQ ID NO:52 | RD06 | Rv1515c | MTCY277.37c | "H37Rv, segment 65: 23614, 36347" |
| SEQ ID NO:53 | RD06 | Rv1516c | MTCY277.38c | "H37Rv, segment 65: 23614, 36347" |

TABLE I-continued

| SEQ ID | rd | rv_num | orf_Id | breakpoint |
|---|---|---|---|---|
| SEQ ID NO:54 | RD07 | Rv2346c | MTCY98.15c | "H37Rv, segment 103: 17622, 26584" |
| SEQ ID NO:55 | RD07 | Rv2347c | MTCY98.16c | "H37Rv, segment 103: 17622, 26584" |
| SEQ ID NO:56 | RD07 | Rv2348c | MTCY98.17c | "H37Rv, segment 103: 17622, 26584" |
| SEQ ID NO:57 | RD07 | Rv2349c | MTCY98.18c | "H37Rv, segment 103: 17622, 26584" |
| SEQ ID NO:58 | RD07 | Rv2350c | MTCY98.19c | "H37Rv, segment 103: 17622, 26584" |
| SEQ ID NO:59 | RD07 | Rv2351c | MTCY98.20c | "H37Rv, segment 103: 17622, 26584" |
| SEQ ID NO:60 | RD07 | Rv2352c | MTCY98.21c | "H37Rv, segment 103: 17622, 26584" |
| SEQ ID NO:61 | RD07 | Rv2353c | MTCY98.22c | "H37Rv, segment 103: 17622, 26584" |
| SEQ ID NO:62 | RD08 | Rv0309 | MTCY63.14 | "H37Rv, segment 16: 17018, 20446" |
| SEQ ID NO:63 | RD08 | Rv0310c | MTCY63.15c | "H37Rv, segment 16: 17018, 20446" |
| SEQ ID NO:64 | RD08 | Rv0311 | MTCY63.16 | "H37Rv, segment 16: 17018, 20446" |
| SEQ ID NO:65 | RD08 | Rv0312 | MTCY63.17 | "H37Rv, segment 16: 17018, 20446" |
| SEQ ID NO:66 | RD09 | Rv3623 | MTCY15C10.29c | "H37Rv, segment 153: 21131, segment 154: 2832" |
| SEQ ID NO:67 | RD09 | Rv3622c | MTCY15C10.30 | "H37Rv, segment 153: 21131, segment 154: 2832" |
| SEQ ID NO:68 | RD09 | Rv3621c | MTCY15C10.31 | "H37Rv, segment 153: 21131, segment 154: 2832" |
| SEQ ID NO:69 | RD09 | Rv3620c | MTCY15C10.32 | "H37Rv, segment 153: 21131, segment 154: 2832" |
| SEQ ID NO:70 | RD09 | Rv3619c | MTCY15C10.33 | "H37Rv, segment 153: 21131, segment 154: 2832" |
| SEQ ID NO:71 | RD09 | Rv3618 | MTCY15C10.34c | "H37Rv, segment 153: 21131, segment 154: 2832" |
| SEQ ID NO:72 | RD09 | Rv3617 | MTCY15010.35c | "H37Rv, segment 153: 21131, segment 154: 2832" |
| SEQ ID NO:73 | RD10 | Rv1257c | MTCY50.25 | "H37Rv segment 55: 3689, 6696" |
| SEQ ID NO:74 | RD10 | Rv1256c | MTCY50.26 | "H37Rv segment 55: 3689, 6696" |
| SEQ ID NO:75 | RD10 | Rv1255c | MTCY50.27 | "H37Rv segment 55: 3689, 6696" |
| SEQ ID NO:76 | RD11 | Rv3429 | MTCY77.01 | "H37Rv, segment 145: 30303 to segment 146: 1475" |
| SEQ ID NO:77 | RD11 | Rv3428c | MTCY78.01 | "H37Rv, segment 145: 30303 to segment 146: 1475" |
| SEQ ID NO:78 | RD11 | Rv3427c | MTCY78.02 | "H37Rv, segment 145: 30303 to segment 146: 1475" |
| SEQ ID NO:79 | RD11 | Rv3426 | MTCY78.03c | "H37Rv, segment 145: 30303 to segment 146: 1475" |
| SEQ ID NO:80 | RD11 | Rv3425 | MTCY78.04c | "H37Rv, segment 145: 30303 to segment 146: 1475" |
| SEQ ID NO:81 | RD12 | Rv2072c | MTCY49.11c | "H37Rv segment 93: 9301, 11331" |
| SEQ ID NO:82 | RD12 | Rv2073c | MTCY49.12c | "H37Rv segment 93: 9301, 11331" |
| SEQ ID NO:83 | RD12 | Rv2074 | MTCY49.13 | "H37Rv segment 93: 9301, 11331" |
| SEQ ID NO:84 | RD12 | Rv2075c | MTCY49.14c | "H37Rv segment 93: 9301, 11331" |
| SEQ ID NO:85 | RD13bis | Rv2645 | MTCY441.15 | "H37Rv, segment 118: 12475, 23455" |
| SEQ ID NO:86 | RD13bis | Rv2646 | MTCY441.16 | "H37Rv, segment 118: 12475, 23455" |
| SEQ ID NO:87 | RD13bis | Rv2647 | MTCY441.17 | "H37Rv, segment 118: 12475, 23455" |
| SEQ ID NO:88 | RD13bis | Rv2648 | MTCY441.17A | "H37Rv, segment 118: 12475, 23455" |
| SEQ ID NO:89 | RD13bis | Rv2649 | MTCY441.18 | "H37Rv, segment 118: 12475, 23455" |
| SEQ ID NO:90 | RD13bis | Rv2650c | MTCY441.19 | "H37Rv, segment 118: 12475, 23455" |
| SEQ ID NO:91 | RD13bis | Rv2651c | MTCY441.20c | "H37Rv, segment 118: 12475, 23455" |
| SEQ ID NO:92 | RD13bis | Rv2652c | MTCY441.21c | "H37Rv, segment 118: 12475, 23455" |
| SEQ ID NO:93 | RD13bis | Rv2653c | MTCY441.22c | "H37Rv, segment 118: 12475, 23455" |
| SEQ ID NO:94 | RD13bis | Rv2654c | MTCY441.23c | "H37Rv, segment 118: 12475, 23455" |
| SEQ ID NO:95 | RD13bis | Rv2655c | MTCY441.24c | "H37Rv, segment 118: 12475, 23455" |
| SEQ ID NO:96 | RD13bis | Rv2656c | MTCY441.25c | "H37Rv, segment 118: 12475, 23455" |
| SEQ ID NO:97 | RD13bis | Rv2657c | MTCY441.26c | "H37Rv, segment 118: 12475, 23455" |
| SEQ ID NO:98 | RD13bis | Rv2658c | MTCY441.27c | "H37Rv, segment 118: 12475, 23455" |
| SEQ ID NO:99 | RD13bis | Rv2659c | MTCY441.28c | "H37Rv, segment 118: 12475, 23455" |
| SEQ ID NO:100 | RD13bis | Rv2660c | MTCY441.29c | "H37Rv, segment 118: 12475, 23455" |
| SEQ ID NO:101 | RD14 | Rv1766 | MTCY28.32 | "H37Rv segment 79: 30573, 39642" |
| SEQ ID NO:102 | RD14 | Rv1767 | MTCY28.33 | "H37Rv segment 79: 30573, 39642" |
| SEQ ID NO:103 | RD14 | Rv1768 | MTCY28.34 | "H37Rv segment 79: 30573, 39642" |
| SEQ ID NO:104 | RD14 | Rv1769 | MTCY28.35 | "H37Rv segment 79: 30573, 39642" |
| SEQ ID NO:105 | RD14 | Rv1770 | MTCY28.36 | "H37Rv segment 79: 30573, 39642" |
| SEQ ID NO:106 | RD14 | Rv1771 | MTCY28.37 | "H37Rv segment 79: 30573, 39642" |
| SEQ ID NO:107 | RD14 | Rv1772 | MTCY28.38 | "H37Rv segment 79: 30573, 39642" |
| SEQ ID NO:108 | RD14 | Rv1773c | MTCY28.39 | "H37Rv segment 79: 30573, 39642" |
| SEQ ID NO:109 | RD15 | Rv1963c | MTV051.01c | "H37Rv segment 88: 1153, 13873" |
| SEQ ID NO:110 | RD15 | Rv1964 | MTV051.02 | "H37Rv segment 88: 1153, 13873" |
| SEQ ID NO:111 | RD15 | Rv1965 | MTV051.03 | "H37Rv segment 88: 1153, 13873" |
| SEQ ID NO:112 | RD15 | Rv1966 | MTV051.04 | "H37Rv segment 88: 1153, 13873" |
| SEQ ID NO:113 | RD15 | Rv1967 | MTV0S1.05 | "H37Rv segment 88:1153, 13873" |
| SEQ ID NO:114 | RD15 | Rv1968 | MTV051.06 | "H37Rv segment 88: 1153, 13873" |
| SEQ ID NO:115 | RD15 | Rv1969 | MTV051.07 | "H37Rv segment 88: 1153, 13873" |
| SEQ ID NO:116 | RD15 | Rv1970 | MTV051.08 | "H37Rv segment 88: 1153, 13873" |
| SEQ ID NO:117 | RD15 | Rv1971 | MTV051.09 | "H37Rv segment 88: 1153, 13873" |
| SEQ ID NO:118 | RD15 | Rv1972 | MTV051.10 | "H37Rv segment 88: 1153, 13873" |
| SEQ ID NO:119 | RD15 | Rv1973 | MTV051.11 | "H37Rv segment 88: 1153, 13873" |
| SEQ ID NO:120 | RD15 | Rv1974 | MTV051.12 | "H37Rv segment 88: 1153, 13873" |
| SEQ ID NO:121 | RD15 | Rv1975 | MTV051.13 | "H37Rv segment 88: 1153, 13873" |
| SEQ ID NO:122 | RD15 | Rv1976c | MTV051.14 | "H37Rv segment 88: 1153, 13873" |
| SEQ ID NO:123 | RD15 | Rv1977 | MTV051.15 | "H37Rv segment 88: 1153, 13873" |
| SEQ ID NO:124 | RD16 | Rv3405c | MTCY78.23 | "H37Rv, segment 145: 5012, 12621" |
| SEQ ID NO:125 | RD16 | Rv3404c | MTCY78.24 | "H37Rv, segment 145: 5012, 12621" |
| SEQ ID NO:126 | RD16 | Rv3403c | MTCY78.25 | "H37Rv, segment 145: 5012, 12621" |
| SEQ ID NO:127 | RD16 | Rv3402c | MTCY78.26 | "H37Rv, segment 145: 5012, 12621" |
| SEQ ID NO:128 | RD16 | Rv3401 | MTCY78.27c | "H37Rv, segment 145: 5012, 12621" |
| SEQ ID NO:129 | RD16 | Rv3400 | MTCY78.28c | "H37Rv, segment 145: 5012, 12621" |

The "Rv" column indicates public *M. tb.* sequence, open reading frame. The BCG strains were obtained as follows:

TABLE 2

Strains employed in study of BCG phylogeny

| Name of strain | Synonym | Source | Descriptors |
|---|---|---|---|
| BCG-Russia | Moscow | ATCC | #35740 |
| BCG-Moreau | Brazil | ATCC | #35736 |
| BCG-Moreau | Brazil | IAF | dated 1958 |
| BCG-Moreau | Brazil | IAF | dated 1961 |
| BCG-Japan | Tokyo | ATCC | #35737 |
| BCG-Japan | Tokyo | IAF | dated 1961 |
| BCG-Japan | Tokyo | JATA | vaccine strain |
| BCG-Japan | Tokyo | JATA | bladder cancer strain |
| BCG-Japan | Tokyo | JATA | clinical isolate - adenitis |
| BCG-Sweden | Gothenburg | ATCC | #35732 |
| BCG-Sweden | Gothenburg | IAF | dated 1958 |
| BCG-Sweden | Gothenburg | SSI | production lot, Copenhagen |
| BCG-Phipps | Philadelphia | ATCC | #35744 |
| BCG-Denmark | Danish 1331 | ATCC | #35733 |
| BCG-Copenhagen | | ATCC | #27290 |
| BCG-Copenhagen | | IAF | dated 1961 |
| BCG-Tice | Chicago | vaccine | dated 1973 |
| BCG-Tice | Chicago | ATCC | #35743 |
| BCG-Frappier | Montreal | IAF | primary lot, 1973 |
| BCG-Frappier, INH-resistant | Montreal-R | IAF | primary lot, 1973 |
| BCG-Frappier | Montreal | IAF | passage 946 |
| BCG-Connaught | Toronto | CL | bladder cancer treatment |
| BCG-Birkhaug | | ATCC | #35731 |
| BCG-Prague | Czech | SSI | lyophilized 1968 |
| BCG-Glaxo | | vaccine | dated 1973 |
| BCG-Glaxo | | ATCC | #35741 |
| BCG-Pasteur | | IAF | passage 888 |
| BCG-Pasteur | | IAF | dated 1961 |
| BCG-Pasteur | | IP | 1173P2-B |
| BCG-Pasteur | | IP | 1173P2-C |
| BCG-Pasteur | | IP | clinical isolate #1 |
| BCG-Pasteur | | IP | clinical isolate #2 |
| BCG-Pasteur | | ATCC | #35734 |

Abbreviations: IP = Institut Pasteur, Paris, France; IAF = Institut Armand Frappier, Laval, Canada; ATCC = American Type Culture Collection, Rockville, Md, USA; SSI = Statens Serum Institute, Copenhagen, Denmark; CL = Connaught Laboratories, Willowdale, Canada, JATA = Japanese Anti-Tuberculosis Association; INH = isoniazid. Canadian BCG's refers to BCG-Montreal and BCG-Toronto, the latter being derived from the former.

In performing the initial screening method, genomic DNA is isolated from two mycobacteria microbial cell cultures. The two DNA preparations are labeled, where a different label is used for the first and second microbial cultures, typically using nucleotides conjugated to a fluorochrome that emits at a wavelength substantially different from that of the fluorochrome tagged nucleotides used to label the selected probe. The strains used were the reference strain of *Mycobacterium tuberculosis* (H37Rv), other *M. tb.* laboratory strains, such as H37Ra, the O strain, *M. tb.* clinical isolates, the reference strain of *Mycobacterium bovis*, and different strains of *Mycobacterium bovis* BCG.

The two DNA preparations are mixed, and competitive hybridization is carried out to a microarray representing all of the open reading frames in the genome of the test microbe, usually H37Rv. Hybridization of the labeled sequences is accomplished according to methods well known in the art. In a preferred embodiment, the two probes are combined to provide for a competitive hybridization to a single microarray. Hybridization can be carried out under conditions varying in stringency, preferably under conditions of high stringency (e.g., 4×SSC, 10% SDS, 65° C.) to allow for hybridization of complementary sequences having extensive homology (e.g., having at least 85% sequence identity, preferably at least 90% sequence identity, more preferably having at least 95% sequence identity). Where the target sequences are native sequences the hybridization is preferably carried out under conditions that allow hybridization of only highly homologous sequences (e.g., at least 95% to 100% sequence identity).

Two color fluorescent hybridization is utilized to assay the representation of the unselected library in relation to the selected library (i.e., to detect hybridization of the unselected probe relative to the selected probe). From the ratio of one color to the other, for any particular array element, the relative abundance of that sequence in the unselected and selected libraries can be determined. In addition, comparison of the hybridization of the selected and unselected probes provides an internal control for the assay. An absence of signal from the reference strain, as compared to H37Rv, is indicative that the open reading frame is deleted in the test strain. The deletion may be further mapped by Southern blot analysis, and by sequencing the regions flanking the deletion.

Microarrays can be scanned to detect hybridization of the selected and the unselected sequences using a custom built scanning laser microscope as described in Shalon et al., *Genome Res.* 6:639 (1996). A separate scan, using the appropriate excitation line, is performed for each of the two fluorophores used. The digital images generated from the scan are then combined for subsequent analysis. For any particular array element, the ratio of the fluorescent signal from the amplified selected cell population DNA is compared to the fluorescent signal from the unselected cell population DNA, and the relative abundance of that sequence in the selected and unselected library determined.

Nucleic Acid Compositions

As used herein, the term "deletion marker", or "marker" is used to refer to those sequences of *M. tuberculosis* complex genomes that are deleted in one or more of the strains or species, as indicated in Table 1. The bacteria of the *M. tuberculosis* complex include *M. tuberculosis, M. bovis*, and BCG, inclusive of varied isolates and strains within each species. Nucleic acids of interest include all or a portion of the deleted region, particularly complete open reading frames, hybridization primers, promoter regions, etc.

The term "junction" or "deletion junction" is used to refer to nucleic acids that comprise the regions on both the 3' and the 5' sequence immediately flanking the deletion. Such junction sequences are preferably used as short primers, e.g. from about 15 nt to about 30 nt, that specifically hybridize to the junction, but not to a nucleic acid comprising the undeleted genomic sequence. For example, the deletion found in *M. bovis*, at Rv0221, corresponds to the nucleotide sequence of the *M. tuberculosis* H37Rv genome, segment 12: 17432,19335. The junction comprises the regions upstream of position 17342, and downstream of 19335, e.g. a nucleic acid of 20 nucleotides comprising the sequence from H37Rv 17332–17342 joined to 19335–19345.

Typically, such nucleic acids comprising a junction will include at least about 7 nucleotides from each flanking region, i.e. from the 3' and from the 5' sequences adjacent to the deletion, and may be about 10 nucleotides from each flanking region, up to about 15 nucleotides, or more. Amplification primers that hybridize to the junction sequence, to the deleted sequence, and to the flanking non-deleted regions have a variety of uses, as detailed below.

The nucleic acid compositions of the subject invention encode all or a part of the deletion markers. Fragments may be obtained of the DNA sequence by chemically synthesizing oligonucleotides in accordance with conventional methods, by restriction enzyme digestion, by PCR amplification, etc. For the most part, DNA fragments will be at least about 25 nt in length, usually at least about 30 nt, more usually at least about 50 nt. For use in amplification reactions, such as PCR, a pair of primers will be used. The exact composition of the primer sequences is not critical to the invention, but for most applications the primers will hybridize to the subject sequence under stringent conditions, as known in the art. It is preferable to chose a pair of primers that will generate an amplification product of at least about 50 nt, preferably at least about 100 nt. Algorithms for the selection of primer sequences are generally known, and are available in commercial software packages. Amplification primers hybridize to complementary strands of DNA, and will prime towards each other.

Usually, the DNA will be obtained substantially free of other nucleic acid sequences that do not include a deletion marker sequence or fragment thereof, generally being at least about 50%, usually at least about 90% pure and are typically "recombinant", i.e. flanked by one or more nucleotides with which it is not normally associated on a naturally occurring chromosome.

For screening purposes, hybridization probes of one or more of the deletion sequences may be used in separate reactions or spatially separated on a solid phase matrix, or labeled such that they can be distinguished from each other. Assays may utilize nucleic acids that hybridize to one or more of the described deletions.

An array may include all or a subset of the deletion markers listed in Table 1. Usually such an array will include at least 2 different deletion marker sequences, i.e. deletions located at unique positions within the locus, and may include all of the provided deletion markers. Arrays of interest may further comprise other genetic sequences, particularly other sequences of interest for tuberculosis screening. The oligonucleotide sequence on the array will usually be at least about 12 nt in length, may be the length of the provided deletion marker sequences, or may extend into the flanking regions to generate fragments of 100 to 200 nt in length. For examples of arrays, see Ramsay (1998) *Nat. Biotech.* 16:40–44; Hacia et al. (1996) *Nature Genetics* 14:441–447; Lockhart et al. (1996) *Nature Biotechnol.* 14:1675–1680; and De Risi et al. (1996) *Nature Genetics* 14:457–460.

Nucleic acids may be naturally occurring, e.g. DNA or RNA, or may be synthetic analogs, as known in the art. Such analogs may be preferred for use as probes because of superior stability under assay conditions. Modifications in the native structure, including alterations in the backbone, sugars or heterocyclic bases, have been shown to increase intracellular stability and binding affinity. Among useful changes in the backbone chemistry are phosphorothioates; phosphorodithioates, where both of the non-bridging oxygens are substituted with sulfur; phosphoroamidites; alkyl phosphotriesters and boranophosphates. Achiral phosphate derivatives include 3'-O'-5'-S-phosphorothioate, 3'-S-5'-O-phosphorothioate, 3'-$CH_2$-5'-O-phosphonate and 3'-NH-5'-O-phosphoroamidate. Peptide nucleic acids replace the entire ribose phosphodiester backbone with a peptide linkage.

Sugar modifications are also used to enhance stability and affinity. The α-anomer of deoxyribose may be used, where the base is inverted with respect to the natural b-anomer. The 2'-OH of the ribose sugar may be altered to form 2'-O-methyl or 2'-O-allyl sugars, which provide resistance to degradation without comprising affinity.

Modification of the heterocyclic bases must maintain proper base pairing. Some useful substitutions include deoxyuridine for deoxythymidine; 5-methyl-2'-deoxycytidine and 5-bromo-2'-deoxycytidine for deoxycytidine. 5-propynyl-2'-deoxyuridine and 5-propynyl-2'-deoxycytidine have been shown to increase affinity and biological activity when substituted for deoxythymidine and deoxycytidine, respectively.

Polypeptide Compositions

The specific deletion markers in Table 1 correspond to open reading frames of the *M. tb.* genome, and therefore encode a polypeptide. The subject markers may be employed for synthesis of a complete protein, or polypeptide fragments thereof, particularly fragments corresponding to functional domains; binding sites; etc.; and including fusions of the subject polypeptides to other proteins or parts thereof. For expression, an expression cassette may be employed, providing for a transcriptional and translational initiation region, which may be inducible or constitutive, where the coding region is operably linked under the transcriptional control of the transcriptional initiation region, and a transcriptional and translational termination region. Various transcriptional initiation regions may be employed that are functional in the expression host.

The polypeptides may be expressed in prokaryotes or eukaryotes in accordance with conventional ways, depending upon the purpose for expression. For large scale production of the protein, a unicellular organism, such as *E. coli, B. subtilis, S. cerevisiae*, or cells of a higher organism such as vertebrates, particularly mammals, e.g. COS 7 cells, may be used as the expression host cells. Small peptides can also be synthesized in the laboratory.

With the availability of the polypeptides in large amounts, by employing an expression host, the polypeptides may be isolated and purified in accordance with conventional ways. A lysate may be prepared of the expression host and the lysate purified using HPLC, exclusion chromatography, gel electrophoresis, affinity chromatography, or other purification technique. The purified polypeptide will generally be at least about 80% pure, preferably at least about 90% pure, and may be up to and including 100% pure. Pure is intended to mean free of other proteins, as well as cellular debris.

The polypeptide is used for the production of antibodies, where short fragments provide for antibodies specific for the particular polypeptide, and larger fragments or the entire protein allow for the production of antibodies over the surface of the polypeptide. Antibodies may be raised to isolated peptides corresponding to particular domains, or to the native protein.

Antibodies are prepared in accordance with conventional ways, where the expressed polypeptide or protein is used as an immunogen, by itself or conjugated to known immunogenic carriers, e.g. KLH, pre-S HBsAg, other viral or eukaryotic proteins, or the like. Various adjuvants may be employed, with a series of injections, as appropriate. For monoclonal antibodies, after one or more booster injections, the spleen is isolated, the lymphocytes immortalized by cell fusion, and then screened for high affinity antibody binding. The immortalized cells, i.e. hybridomas, producing the desired antibodies may then be expanded. For further description, see *Monoclonal Antibodies: A Laboratory Manual*, Harlow and Lane eds., Cold Spring Harbor Laboratories, Cold Spring Harbor, N.Y., 1988. If desired, the mRNA encoding the heavy and light chains may be isolated and mutagenized by cloning in *E. coli*, and the heavy and light chains mixed to further enhance the affinity of the antibody. Alternatives to in vivo immunization as a method of raising antibodies include binding to phage "display" libraries, usually in conjunction with in vitro affinity maturation.

The antibody may be produced as a single chain, instead of the normal multimeric structure. Single chain antibodies are described in Jost et al. (1994) *J.B.C.* 269:26267–73, and others. DNA sequences encoding the variable region of the heavy chain and the variable region of the light chain are ligated to a spacer encoding at least about 4 amino acids of small neutral amino acids, including glycine and/or serine. The protein encoded by this fusion allows assembly of a functional variable region that retains the specificity and affinity of the original antibody.

Use of Deletion Markers in Identification of Mycobacteria

The deletions provided in Table 1 are useful for the identification of a mycobacterium as (a) variants of *M. tb.* (b) isolates of BCG (c) *M. bovis* strains or (d) carrying the identified mycobacterial bacteriophage, depending on the specific marker that is chosen. Such screening is particularly useful in determining whether a particular infection or isolate is pathogenic. The term mycobacteria may refer to any member of the family Mycobacteriacaeae, including *M. tuberculosis, M. avium* complex, *M. kansasii, M. scrofulaceum, M. bovis* and *M. leprae.*

Means of detecting deletions are known in the art. Deletions may be identified through the absence or presence of the sequences in mRNA or genomic DNA, through analysis of junctional regions that flank the deletion, or detection of the gene product, or, particularly relating to the tuberculin skin test, by identification of antibodies that react with the encoded gene product.

While deletions can be easily determined by the absence of hybridization, in many cases it is desirable to have a positive signal, in order to minimize artifactual negative readings. In such cases the deletions may be detected by designing a primer that flanks the junction formed by the deletion. Where the deletion is present, a novel sequence is formed between the flanking regions, which can be detected by hybridization. Preferably such a primer will be sufficiently short that it will only hybridize to the junction, and will fail to form stable hybrids with either of the separate parts of the junction.

Diagnosis is performed by protein, DNA or RNA sequence and/or hybridization analysis of any convenient sample, e.g. cultured mycobacteria, biopsy material, blood sample, etc. Screening may also be based on the functional or antigenic characteristics of the protein. Immunoassays designed to detect the encoded proteins from deleted sequences may be used in screening.

A number of methods are available for analyzing nucleic acids for the presence of a specific sequence. Where large amounts of DNA are available, genomic DNA is used directly. Alternatively, the region of interest is cloned into a suitable vector and grown in sufficient quantity for analysis. The nucleic acid may be amplified by conventional techniques, such as the polymerase chain reaction (PCR), to provide sufficient amounts for analysis. The use of the polymerase chain reaction is described in Saiki, et al. (1985) *Science* 239:487, and a review of current techniques may be found in Sambrook, et al. *Molecular Cloning: A Laboratory Manual*, CSH Press 1989, pp.14.2–14.33. Amplification may also be used to determine whether a polymorphism is present, by using a primer that is specific for the polymorphism. Alternatively, various methods are known in the art that utilize oligonucleotide ligation, for examples see Riley et al. (1990) *N.A.R.* 18:2887–2890; and Delahunty et al. (1996) *Am. J. Hum. Genet.* 58:1239–1246.

A detectable label may be included in an amplification reaction. Suitable labels include fluorochromes, e.g. fluorescein isothiocyanate (FITC), rhodamine, Texas Red, phycoerythrin, allophycocyanin, 6-carboxyfluorescein (6-FAM), 2',7'-dimethoxy-4',5'-dichloro-6-carboxyfluorescein (JOE), 6-carboxy-X-rhodamine (ROX), 6-carboxy-2',4',7',4,7-hexachlorofluorescein (HEX), 5-carboxyfluorescein (5-FAM) or N,N,N',N'-tetramethyl-6-carboxyrhodamine (TAMRA), radioactive labels, e.g. $^{32}P$, $^{35}S$, $^{3}H$; etc. The label may be a two stage system, where the amplified DNA is conjugated to biotin, haptens, etc. having a high affinity binding partner, e.g. avidin, specific antibodies, etc., where the binding partner is conjugated to a detectable label. The label may be conjugated to one or both of the primers. Alternatively, the pool of nucleotides used in the amplification is labeled, so as to incorporate the label into the amplification product.

The sample nucleic acid, e.g. amplified or cloned fragment, is analyzed by one of a number of methods known in the art. The nucleic acid may be sequenced by dideoxy or other methods, and the sequence of bases compared to the deleted sequence. Hybridization with the variant sequence may also be used to determine its presence, by Southern blots, dot blots, etc. The hybridization pattern of a control and variant sequence to an array of oligonucleotide probes immobilized on a solid support, as described in U.S. Pat. No. 5,445,934, or in WO95/35505, may also be used as a means of detecting the presence of variable sequences. Single strand conformational polymorphism (SSCP) analysis, denaturing gradient gel electrophoresis (DGGE), mismatch cleavage detection, and heteroduplex analysis in gel matrices are used to detect conformational changes created by DNA sequence variation as alterations in electrophoretic mobility. Alternatively, where a polymorphism creates or destroys a recognition site for a restriction endonuclease (restriction fragment length polymorphism, RFLP), the sample is digested with that endonuclease, and the products size fractionated to determine whether the fragment was digested. Fractionation is performed by gel or capillary electrophoresis, particularly acrylamide or agarose gels.

The hybridization pattern of a control and variant sequence to an array of oligonucleotide probes immobilized on a solid support, as described in U.S. Pat. No. 5,445,934, or in WO95/35505, may be used as a means of detecting the presence or absence of deleted sequences. In one embodiment of the invention, an array of oligonucleotides is provided, where discrete positions on the array are complementary to at least a portion of *M. tb.* genomic DNA, usually comprising at least a portion from the identified open reading frames. Such an array may comprise a series of oligonucleotides, each of which can specifically hybridize to a nucleic acid, e.g. mRNA, cDNA, genomic DNA, etc.

Deletions may also be detected by amplification. In an embodiment of the invention, sequences are amplified that include a deletion junction, i.e. where the amplification primers hybridize to a junction sequence. In a nucleic acid sample where the marker sequence is deleted, a junction will be formed, and the primer will hybridize, thereby allowing amplification of a detectable sequence. In a nucleic acid sample where the marker sequence is present, the primer will not hybridize, and no amplification will take place. Alternatively, amplification primers may be chosen such that amplification of the target sequence will only take place where the marker sequence is present. The amplification products may be separated by size using any convenient method, as known in the art, including gel electrophoresis, chromatography, capillary electrophoresis, density gradient fractionation, etc.

In addition to the detection of deletions by the detection of junctions sequences, or detection of the marker sequences themselves, one may determine the presence or absence of the encoded protein product. The specific deletions in Table 1 correspond to open reading frames of the *M. tb.* genome, and therefore encode polypeptides. Polypeptides are detected by means known in the art, including determining the presence of the specific polypeptide in a sample through biochemical, functional or immunological characterization. The detection of antibodies in patient serum that react with a polypeptide is of particular interest.

Immunization with BCG typically leads to a positive response against tuberculin antigens in a skin test. In people who have been immunized, which includes a significant proportion of the world population, it is therefore difficult to determine whether a positive test is the result of an immune reaction to the BCG vaccine, or to an ongoing *M. tb.* infection. The subject invention has provided a number of open reading frame sequences that are present in *M. tb.* isolates, but are absent in BCG. As a primary or a secondary screening method, one may test for immunoreactivity of the patient with the polypeptides encoded by such deletion markers. Diagnosis may be performed by a number of methods. The different methods all determine the presence of an immune response to the polypeptide in a patient, where a positive response is indicative of an *M. tb.* infection. The immune response may be determined by determination of antibody binding, or by the presence of a response to intradermal challenge with the polypeptide.

In one method, a dose of the deletion marker polypeptide, formulated as a cocktail of proteins or as individual protein species, in a suitable medium is injected subcutaneously into the patient. The dose will usually be at least about 0.05 $\mu$g of protein, and usually not more than about 5 $\mu$g of protein. A control comprising medium alone, or an unrelated protein will be injected nearby at the same time. The site of injection is examined after a period of time for the presence of a wheal. The wheal at the site of polypeptide injection is compared to that at the site of the control injection, usually by measuring the size of the wheal. The skin test readings may be assessed by a variety of objective grading systems. A positive result for the presence of an allergic condition will show an increased diameter at the site of polypeptide injection as compared to the control, usually at least about 50% increase in size, more usually at least 100% increase in size.

An alternative method for diagnosis depends on the in vitro detection of binding between antibodies in a patient sample and the subject polypeptides, either as a cocktail or as individual protein species, where the presence of specific binding is indicative of an infection. Measuring the concentration of polypeptide specific antibodies in a sample or fraction thereof may be accomplished by a variety of specific assays. In general, the assay will measure the reactivity between a patient sample, usually blood derived, generally in the form of plasma or serum. The patient sample may be used directly, or diluted as appropriate, usually about 1:10 and usually not more than about 1:10,000. Immunoassays may be performed in any physiological buffer, e.g. PBS, normal saline, HBSS, dPBS, etc.

In a preferred embodiment, a conventional sandwich type assay is used. A sandwich assay is performed by first attaching the polypeptide to an insoluble surface or support. The polypeptide may be bound to the surface by any convenient means, depending upon the nature of the surface, either directly or through specific antibodies. The particular manner of binding is not crucial so long as it is compatible with the reagents and overall methods of the invention. They may be bound to the plates covalently or non-covalently, preferably non-covalently. Samples, fractions or aliquots thereof are then added to separately assayable supports (for example, separate wells of a microtiter plate) containing support-bound polypeptide. Preferably, a series of standards, containing known concentrations of antibodies is assayed in parallel with the samples or aliquots thereof to serve as controls.

Immune specific receptors may be labeled to facilitate direct, or indirect quantification of binding. Examples of labels which permit direct measurement of second receptor binding include radiolabels, such as $^{3}$H or $^{125}$I, fluorescers, dyes, beads, chemilumninescers, colloidal particles, and the like. Examples of labels which permit indirect measurement of binding include enzymes where the substrate may provide for a colored or fluorescent product. In a preferred embodiment, the second receptors are antibodies labeled with a covalently bound enzyme capable of providing a detectable product signal after addition of suitable substrate. Examples of suitable enzymes for use in conjugates include horseradish peroxidase, alkaline phosphatase, malate dehydrogenase and the like. Where not commercially available, such antibody-enzyme conjugates are readily produced by techniques known to those skilled in the art.

In some cases, a competitive assay will be used. In addition to the patient sample, a competitor to the antibody is added to the reaction mix. The competitor and the antibody compete for binding to the polypeptide. Usually, the competitor molecule will be labeled and detected as previously described, where the amount of competitor binding will be proportional to the amount of Immune present. The concentration of competitor molecule will be from about 10 times the maximum anticipated Immune concentration to about equal concentration in order to make the most sensitive and linear range of detection.

Alternatively, antibodies may be used for direct determination of the presence of the deletion marker polypeptide. Antibodies specific for the subject deletion markers as previously described may be used in screening immunoassays. Samples, as used herein, include microbial cultures, biological fluids such as tracheal lavage, blood, etc. Also included in the term are derivatives and fractions of such fluids. Diagnosis may be performed by a number of methods. The different methods all determine the absence or presence of polypeptides encoded by the subject deletion markers. For example, detection may utilize staining of mycobacterial cells or histological sections, performed in accordance with conventional methods. The antibodies of interest are added to the cell sample, and incubated for a period of time sufficient to allow binding to the epitope, usually at least about 10 minutes. The antibody may be labeled with radioisotopes, enzymes, fluorescers, chemiluminescers, or other labels for direct detection. Alternatively, a second stage antibody or reagent is used to amplify the signal. Such reagents are well known in the art. For example, the primary antibody may be conjugated to biotin, with horseradish peroxidase-conjugated avidin added as a second stage reagent. Final detection uses a substrate that undergoes a color change in the presence of the peroxidase. The absence or presence of antibody binding may be determined by various methods, including microscopy, radiography, scintillation counting, etc.

An alternative method for diagnosis depends on the in vitro detection of binding between antibodies and the subject polypeptides in solution, e.g. a cell lysate. Measuring the concentration of binding in a sample or fraction thereof may be accomplished by a variety of specific assays. A conventional sandwich type assay may be used. For example, a sandwich assay may first attach specific antibodies to an insoluble surface or support. The particular manner of binding is not crucial so long as it is compatible with the reagents and overall methods of the invention. They may be bound to the plates covalently or non-covalently, preferably non-covalently. The insoluble supports may be any compositions to which polypeptides can be bound, which is readily separated from soluble material, and which is otherwise compatible with the overall method. The surface of such supports may be solid or porous and of any convenient shape. Examples of suitable insoluble supports to which the receptor is bound include beads, e.g. magnetic beads, membranes and microtiter plates. These are typically made of glass, plastic (e.g. polystyrene), polysaccharides, nylon or nitrocellulose. Microtiter plates are especially convenient because a large number of assays can be carried out simultaneously, using small amounts of reagents and samples.

Samples are then added to separately assayable supports (for example, separate wells of a microtiter plate) containing antibodies. Preferably, a series of standards, containing known concentrations of the polypeptides is assayed in parallel with the samples or aliquots thereof to serve as controls. Preferably, each sample and standard will be added to multiple wells so that mean values can be obtained for each. The incubation time should be sufficient for binding, generally, from about 0.1 to 3 hr is sufficient. After incubation, the insoluble support is generally washed of non-bound components. Generally, a dilute non-ionic detergent medium at an appropriate pH, generally 7–8, is used as a wash medium. From one to six washes may be employed, with sufficient volume to thoroughly wash non-specifically bound proteins present in the sample.

After washing, a solution containing a second antibody is applied. The antibody will bind with sufficient specificity such that it can be distinguished from other components present. The second antibodies may be labeled to facilitate direct, or indirect quantification of binding. Examples of labels that permit direct measurement of second receptor binding include radiolabels, such as $^{3}H$ or $^{125}I$, fluorescers, dyes, beads, chemilumninescers, colloidal particles, and the like. Examples of labels which permit indirect measurement of binding include enzymes where the substrate may provide for a colored or fluorescent product. In a preferred embodiment, the antibodies are labeled with a covalently bound enzyme capable of providing a detectable product signal after addition of suitable substrate. Examples of suitable enzymes for use in conjugates include horseradish peroxidase, alkaline phosphatase, malate dehydrogenase and the like. Where not commercially available, such antibody-enzyme conjugates are readily produced by techniques known to those skilled in the art. The incubation time should be sufficient for the labeled ligand to bind available molecules. Generally, from about 0.1 to 3 hr is sufficient, usually 1 hr sufficing.

After the second binding step, the insoluble support is again washed free of non-specifically bound material. The signal produced by the bound conjugate is detected by conventional means. Where an enzyme conjugate is used, an appropriate enzyme substrate is provided so a detectable product is formed.

Other immunoassays are known in the art and may find use as diagnostics. Ouchterlony plates provide a simple determination of antibody binding. Western blots may be performed on protein gels or protein spots on filters, using a detection system specific for the polypeptide, conveniently using a labeling method as described for the sandwich assay.

Recombinant Mycobacterium

Mycobacterium, particularly those of the *M. tuberculosis* complex, are genetically engineered to contain specific deletions or insertions corresponding to the identified genetic markers. In particular, attenuated BCG strains are modified to introduce deleted genes encoding sequences important in the establishment of effective immunity. Alternatively, *M. bovis* or *M. tuberculosis* are modified by homologous recombination to create specific deletions in sequences that determine virulence, i.e. the bacteria are attenuated through recombinant techniques.

In order to stably introduce sequences into BCG, the *M. tb.* open reading frame corresponding to one of the deletions in Table 1 is inserted into a vector that is maintained in *M. bovis* strains. Preferably, the native 5' and 3' flanking sequences are included, in order to provide for suitable regulation of transcription and translation. However, in special circumstances, exogenous promoters and other regulatory regions may be included. Vectors and methods of transfection for BCG are known in the art. For example, U.S. Pat. No. 5,776,465, herein incorporated by reference, describes the introduction of exogenous genes into BCG.

In one embodiment of the invention, the complete deleted region is replaced in BCG. The junctions of the deletion are determined as compared to a wild type *M. tb.* or *M. bovis* sequence, for example as set forth in the experimental section. The deleted region is cloned by any convenient method, as known in the art, e.g. PCR amplification of the region, restriction endonuclease digestion, chemical synthesis, etc. Preferably the cloned region will further comprise flanking sequences of a length sufficient to induce homologous recombination, usually at least about 25 nt, more usually at least about 100 nt, or greater. Suitable vectors and methods are known in the art, for an example, see Norman et al. (1995) *Mol. Microbiol.* 16:755–760.

In an alternative embodiment, one or more of the deletions provided in Table 1 are introduced into a strain of *M. tuberculosis* or *M. bovis*. Preferably such a strain is reduced in virulence, e.g. H37Ra, etc. Methods of homologous recombination in order to effect deletions in mycobacteria are known in the art, for example, see Norman et al., supra.; Ganjam et al. (1991) *P.N.A.S.* 88:5433–5437; and Aldovini et al. (1993) *J. Bacteriol.* 175:7282–7289. Deletions may comprise an open reading frame identified in Table 1, or may extend to the full deletion, i.e. extending into flanking regions, and may include multiple open reading frames.

The ability of the genetically altered mycobacterium to cause disease may be tested in one or more experimental models. For example, *M. tb.* is known to infect a variety of animals, and cells in culture. In one assay, mammalian macrophages, preferably human macrophages, are infected. In a comparison of virulent, avirulent and attenuated strains of the *M. tuberculosis* complex, alveolar or peripheral blood monocytes are infected at a 1:1 ratio (Silver et al. (1998) *Infect Immun* 66(3):1190–1199; Paul et al. (1996) *J Infect Dis* 174(1):105–112.) The percentages of cells infected by the strains and the initial numbers of intracellular organisms are equivalent, as were levels of monocyte viability up to 7 days following infection. However, intracellular growth reflects virulence, over a period of one or more weeks. Mycobacterial growth may be evaluated by acid-fast staining, electron microscopy, and colony-forming units (cfu) assays. Monocyte production of tumor necrosis factor alpha may also be monitored as a marker for virulence.

Other assays for virulence utilize animal models. The *M. tb.* complex bacteria are able to infect a wide variety of animal hosts. One model of particular interest is cavitary tuberculosis produced in rabbits by aerosolized virulent tubercle bacilli (Converse et al. (1996) *Infect Immun* 64(11) :4776–4787). In liquefied caseum, the tubercle bacilli grow extracellularly for the first time since the onset of the disease and can reach such large numbers that mutants with antimicrobial resistance may develop. From a cavity, the bacilli enter the bronchial tree and spread to other parts of the lung and also to other people. Of the commonly used laboratory animals, the rabbit is the only one in which cavitary tuberculosis can be readily produced.

Vaccines may be formulated according to methods known in the art. Vaccines of the modified bacteria are administered to a host which may be exposed to virulent tuberculosis. In many countries where tuberculosis is endemic, vaccination may be performed at birth, with additional vaccinations as necessary. The compounds of the present invention are administered at a dosage that provides effective immunity while minimizing any side-effects. It is contemplated that the composition will be obtained and used under the guidance of a physician.

Conventional vaccine strains of BCG may be formulated in a combination vaccine with polypeptides identified in the present invention and produced as previously described, in order to improve the efficacy of the vaccine.

Various methods for administration may be employed. The formulation may be injected intramuscularly, intravascularly, subcutaneously, etc. The dosage will be conventional. The bacteria can be formulated into pharmaceutical compositions by combination with appropriate, pharmaceutically acceptable carriers or diluents, and may be formulated into preparations in semi-solid or liquid forms, such as solutions, injections, etc. The following methods and excipients are merely exemplary and are in no way limiting.

The modified bacteria can be formulated into preparations for injections by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives. Unit dosage forms for injection or intravenous administration may comprise the bacteria of the present invention in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of vaccine, calculated in an amount sufficient to produce the desired effect in association with a pharmaceutically acceptable diluent, carrier or vehicle. The specifications for the unit dosage forms of the present invention depend on the particular bacteria employed and the effect to be achieved, and the pharmacodynamics associated with each complex in the host.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

Experimental

Methods:

The technical methods used begin with extraction of whole genomic DNA from bacteria grown in culture.

Day 1

Inoculate culture medium of choice (LJ/7H9) and incubate at 35° C. until abundant growth. Dispense 500 μl 1× TE into each tube. (If DNA is in liquid medium, no TE needed.) Transfer loopful (sediment) of cells into microcentrifuge tube containing 500 μl of 1*TE. If taking DNA from liquid medium, let cells collect in bottom of flask. Pipette cells (about 1 ml) into tube. Heat 20 min at 80° C. to kill cells, centrifuge, resuspend in 500 μl of 1*TE. Add 50 μl of 10 mg/ml lysozyme, vortex, incubate overnight at 37° C.

Day2

Add 70 μl of 10% SDS and 10 μl proteinase K, vortex and incubate 20 min. at 65° C. Add 100 μl of 5M NaCl. Add 100 μl of CTAB/NaCl solution, prewarmed at 65° C. Vortex until liquid content white ("milky"). Incubate 10 min at 65° C. Outside of hood, prepare new microcentrifuge tubes labeled with culture # on top, and culture #, tube #, date on side. Add 550 μl isopropanol to each and cap. Back in the hood, add 750 μl of chloroform/isoamyl alcohol, vortex for 10 sec. Centrifuge at room temp for 5 min. at 12,000 g. Transfer aqueous supernatant in 180 μl amounts to new tube using pipetter, being careful to leave behind solids and non-aqueous liquid. Place 30 min at −20 C. Spin 15 min at room temp in a microcentrifuge at 12,000 g. Discard supernatant; leave about 20 μl above pellet. Add 1 ml cold 70% ethanol and turn tube a few times upside down. Spin 5 min at room temp in a microcentrifuge. Discard supernatant; leave about 20 μl above the pellet. Spin 1 min in a microcentrifuge and discard cautiously the last 20 μl supernatant just above the pellet using a pipetter (P-20). Be sure that all traces of ethanol are removed. Allow pellet to dry at room temp for 10 min or speed vac 2–3 min. (Place open tubes in speed vac, close lid, start rotor, turn on vacuum. After 3 min. push red button, turn off vacuum, turn off rotor. Check if pellets are dry by flicking tube to see if pellet comes away from side of tube.) Redissolve the pellet in 20–50 μl of ddH2O. Small pellets get 20, regular sized get 30 and very large get 50. DNA can be stored at 4° C. for further use.

DNA array: was made by spotting DNA fragments onto glass microscope slides which were pretreated with poly-L-lysine. Spotting onto the array was accomplished by a robotic arrayer. The DNA was cross-linked to the glass by ultraviolet irradiation, and the free poly-L-lysine groups were blocked by treatment with 0.05% succinic anhydride, 50% 1-methyl-2-pyrrolidinone and 50% borate buffer.

The majority of spots on the array were PCR-derived products, produced by selecting over 9000 primer pairs designed to amplify the predicted open reading frames of the sequences strain H37Rv (ftp.sanger.ac.uk/pub/TB.seq). Some internal standards and negative control spots including plasmid vectors and non-*M. tb.* DNA were also on the array.

Therefore, with the preparation for an array that contained the whole genome of *Mycobacterium tuberculosis*, we compared BCG-Connaught to *Mycobacterium tuberculosis*, using the array for competitive hybridization. The protocol follows:

DNA labeling protocol. Add 4 $\mu$g DNA in 20 $\mu$l $H_2O$, 2 ml dN10N6 and 36 $\mu$l $H_2O$. 2 ml DNA spike for each DNA sample, for total of 60 $\mu$l. Boil 3 minutes to denature DNA, then snap cool on ice water bath. Add 1 $\mu$l dNTP (5 mM ACG), 10 $\mu$l 10 buffer, 4 $\mu$l Klenow, 22 $\mu$l $H_2O$ to each tube. Add 3 $\mu$l of Cy3 or Cy5 dUTP, for total of 100 $\mu$l. Incubate 3 hours at 37 C. Add 11 $\mu$l 3M NaAc, 250 $\mu$l 100% EtOH to precipitate, store O/N at −20 C. Centrifuge genomic samples 30 minutes at 13K to pellet precipitate. Discard supernatant, add 70% EtOH, spin 15 minutes, discard sup and speed-vac to dry. This provides DNA for two experiments.

DNA hybridization to microarray, protocol. Resuspend the labeled DNA in 11 $\mu$l $dH_2O$ (for 2 arrays). Run out 1 $\mu$l DNA on a 1.5% agarose gel to document sample to be hybridized. Of the remaining 10 $\mu$l of solution, half will be used for this hyb, and half will be left for later date. Take 5 $\mu$l of solution Cy3 and add to same amount of Cy5 solution, for total volume 10 $\mu$l mixed labeled DNA. Add 1 $\mu$l tRNA, 2.75 $\mu$l 20×SSC, 0.4 $\mu$l SDS, for total volume 14.1 $\mu$l. Place on slide at array site, cover with 22 mm coverslip, put slide glass over and squeeze onto rubber devices, then hybridize 4 hours at 65 C. After 4 hours, remove array slides from devices, leave coverslip on, and dip in slide tray into wash buffer consisting of 1×SSC with 0.05% SDS for about 2 minutes. Cover slip should fall off into bath. After 2 minutes in wash buffer, dip once into a bath with 0.06×SSC, then rinse again in 0.06×SSC in separate bath. Dry slides in centrifuge about 600 rpm. They are now ready for scanning.

Fluorescence scanning and data acquisition. Fluorescence scanning was set for 20 microns/pixel and two readings were taken per pixel. Data for channel 1 was set to collect fluorescence from Cy3 with excitation at 520 nm and emission at 550–600 nm. Channel 2 collected signals excited at 647 nm and emitted at 660–705 nm, appropriate for Cy5. No neutral density filters were applied to the signal from either channel, and the photomultiplier tube gain was set to 5. Fine adjustments were then made to the photomultiplier gain so that signals collected from the two spots containing genomic DNA were equivalent.

To analyze the signal from each spot on the array, a 14×14 grid of boxes was applied to the data collected from the array such that signals from within each box were integrated and a value was assigned to the corresponding spot. A background value was obtained for each spot by integrating the signals measured 2 pixels outside the perimeter of the corresponding box. The signal and background values for each spot were imported into a spreadsheet program for further analysis. The background values were subtracted from the signals and a factor of 1.025 was applied to each value in channel 2 to normalize the data with respect to the signals from the genomic DNA spots.

Because the two samples are labeled with different fluorescent dyes, it is possible to determine that a spot of DNA on the array has hybridized to *Mycobacterium tuberculosis* (green dye) and not to BCG (red dye), thus demonstrating a likely deletion from the BCG genome.

However, because the array now contains spots representing 4000 spots, one may expect up to 100 spots with hybridization two standard deviations above or below the mean. Consequently, we have devised a screening protocol, where we look for mismatched hybridization in two consecutive genes on the genome. Therefore, we are essentially looking only for deletions of multiple genes at this point.

To confirm that a gene or group of genes is deleted, we perform Southern hybridization, employing a separate probe from the DNA on the array. Digestions of different mycobacterium DNAs are run on an agarose gel, and transferred to membranes. The membranes can be repeatedly used for probing for different DNA sequences. For the purposes of this project, we include DNA from the reference strain of *Mycobacterium tuberculosis* (H37Rv), from other laboratory strains, such as H37Ra, the O strain, from clinical isolates, from the reference strain of *Mycobacterium bovis*, and from different strains of *Mycobacterium bovis* BCG.

Once a deletion is confirmed by Southern hybridization, we then set out to characterize the exact genomic location. This is done by using polymerase chain reaction, with primers designed to be close to the edges of the deletion, see Talbot (1997) *J Clin Micro*. 35: 566–9

Primers have been chosen to amplify across the deleted region. Only in the absence of this region does one obtain an amplicon. PCR products were examined by electrophoresis (1.5% agarose) and ethidium bromide staining.

Once a short amplicon is obtained, this amplicon is then sequenced. A search of the genome database is performed to determine whether the sequence is exactly identical to one part of the *Mycobacterium tuberculosis* genome, and that the next part of the amplicon is exactly identical to another part of the *Mycobacterium tuberculosis* genome. This permits precise identification of the site of deletion.

Below follows an example of the kind of report obtained:

rd6 bridging PCR, blast search of sequence emb|Z79701|MTCY277 *Mycobacterium tuberculosis* cosmid Y277

Length=38,908

Plus Strand HSPs:

Score=643 (177.7 bits), Expect=1.6e−54, Sum P(2)= 1.6e−54

Identities=129/131 (98%), Positives=129/131 (98%), Strand=Plus/Plus

```
Query:     12  ANTAGTAATGTGCGAGCTGAGCGATGTCGCCGCTCCCAAAAATTACCAATGGTTNGGTCA      71  (SEQ ID NO:130)
               | |||||||||||||||||||||||||||||||||||||||||||||||||||| |||||
Sbjct:  24874  AGTAGTAATGTGCGAGCTGAGCGATGTCGCCGCTCCCAAAAATTACCAATGGTTTGGTCA          (SEQ ID NO:131)

Query:     72  TGACGCCTTCCTAACCAGAATTGTGAATTCATACAAGCCGTAGTCGTGCAGAAGCGCAAC
               ||||||||||||||||||||||||||||||||||||||||||||||||||||||||||||
Sbjct:  24844  TGACGCCTTCCTAACCAGAATTGTGAATTCATACAAGCCGTAGTCGTGCAGAAGCGCAAC

Query:    132  ACTCTTGGAGT                                                142
               |||||||||||
Sbjct:  24904  ACTCTTGGAGT                                              24914
```

Score=224 (61.9 bits), Expect=1.6e−54, Sum P(2)=1.6e−54
Identities=46/49 (93%), Positives=46/49 (93%), Strand=Plus/Plus

```
Query:    141 GTGGCCTACAACGGNGCTCTCCGNGGCGCGGGCGTACCGGATATCTTAG    189 (SEQ ID NO:132)
              | |||||||||||| |||||||| |||||||||||||||||||||||||
Sbjct:  37645 GCGGCCTACAACGGCGCTCTCCGCGGCGCGGGCGTACCGGATATCTTAG  37693 (SEQ ID NO:133)
```

This process is repeated with each suggested deletion, beginning with the three previously described deletions to serve as controls. Sixteen deletions have been identified by these methods, and are listed in Table 1.

It is to be understood that this invention is not limited to the particular methodology, protocols, formulations and reagents described, as such may, of course, vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "and", and "the" include plural referents unless the context clearly dictates otherwise. Thus, for example, reference to "a complex" includes a plurality of such complexes and reference to "the formulation" includes reference to one or more formulations and equivalents thereof known to those skilled in the art, and so forth.

Unless defined otherwise, all technical and scientific terms used herein have the same meaning as commonly understood to one of ordinary skill in the art to which this invention belongs. Although any methods, devices and material similar or equivalent to those described herein can be used in the practice or testing of the invention, the preferred methods, devices and material are now described.

All publications mentioned herein are incorporated herein by reference to the purpose of describing and disclosing, for example, the cell line, constructs, and methodologies that are described in the publications which might be used in connection with the presently described invention. The publications discussed above and throughout the text are provided solely for their disclosure prior to the filing date of the present application. Nothing herein is to be construed as an admission that the inventor are not entitled to antedate such disclosure by virtue of prior invention.

What is claimed is:

1. A method of distinguishing whether a patient has been exposed to a virulent strain of the *M. tuberculosis* complex, the method comprising:

contacting said patient or a sample obtained therefrom with a polypeptide encoded by a nucleotide sequence comprising the open reading frame Rv2654c (SEQ ID NO: 94) or a polypeptide encoded by a nucleotide fragment of at least 25 contiguous nucleotides of SEQ ID NO: 94; and determining the presence of an immune reaction to said polypeptide, wherein a positive response is indicative of exposure to a virulent strain of the *M. tuberculosis* complex.

2. The method of claim 1, wherein said contacting step comprises sub-cutaneous injection of said polypeptide.

3. The method of claim 1, wherein said contacting step is performed in vitro and said sample comprises a blood sample or derivative thereof.

4. The method according to claim 2, wherein said polypeptide is injected at a dose of from 0.05 $\mu$g to 5 $\mu$g.

5. The method according to claim 4, wherein the site of injection is examined for the presence of a wheal, indicative of said positive response.

6. The method according to claim 1, wherein said determining step comprises:

detecting binding of an antibody to said polypeptide, said binding being an indication that said subject is infected by *Mycobacterium tuberculosis* or is diseased with *Mycobacterium tuberculosis*.

7. The method of claim 1, wherein said polypeptide is a fusion protein comprising the polypeptide sequence encoded by SEQ ID NO: 94 or comprising the polypeptide sequence encoded by a nucleotide fragment of at least 25 nucleotides of SEQ ID NO: 94.

8. A method of distinguishing whether a patient has been exposed to a virulent strain of the *M. tuberculosis* complex, the method comprising:

contacting said patient or a sample obtained therefrom with a polypeptide or polypeptide fragment encoded by a nucleotide sequence set forth in the open reading frame Rv2654c (SEQ ID NO:94); and determining the presence of an immune reaction to said polypeptide, wherein a positive response is indicative of exposure to a virulent strain of the *M. tuberculosis* complex.

* * * * *